US012735687B2

(12) United States Patent
Angel et al.

(10) Patent No.: US 12,735,687 B2
(45) Date of Patent: Sep. 15, 2026

(54) ENGINEERED GENE-EDITING PROTEINS

(71) Applicant: Factor Bioscience Inc., Cambridge, MA (US)

(72) Inventors: Matthew Angel, Cambridge, MA (US); Franklin Kostas, Cambridge, MA (US); Mitchell Kopacz, Cambridge, MA (US); Christopher Rohde, Cambridge, MA (US)

(73) Assignee: Factor Bioscience Inc., Cambridge, MA (US)

( * ) Notice: Subject to any disclaimer, the term of this patent is extended or adjusted under 35 U.S.C. 154(b) by 775 days.

(21) Appl. No.: 18/045,829

(22) Filed: Oct. 11, 2022

(65) Prior Publication Data

US 2023/0193231 A1 Jun. 22, 2023

Related U.S. Application Data

(63) Continuation of application No. PCT/US2021/031956, filed on May 12, 2021.

(60) Provisional application No. 63/180,390, filed on Apr. 27, 2021, provisional application No. 63/023,678, filed on May 12, 2020.

(51) Int. Cl.
*C12N 9/22* (2006.01)
*A61F 7/00* (2006.01)
*C12N 5/071* (2010.01)

(52) U.S. Cl.
CPC ............ *C12N 9/22* (2013.01); *C12N 5/0629* (2013.01); *A61F 7/00* (2013.01)

(58) Field of Classification Search
None
See application file for complete search history.

(56) References Cited

U.S. PATENT DOCUMENTS 5,674,844 A 10/1997 Kuberasampath et al.
5,711,964 A 1/1998 Dattagupta et al.
5,733,878 A 3/1998 Kuberasampath et al.
5,849,686 A 12/1998 Kuberasampath et al.
5,891,468 A 4/1999 Martin et al.
6,316,260 B1 11/2001 Freisleben et al.
6,407,060 B1 6/2002 Charette et al.
6,413,544 B1 7/2002 Smyth-Templeton et al.
6,506,729 B1 1/2003 Rueger et al.
6,770,291 B2 8/2004 Smyth-Templeton et al.
6,800,603 B2 10/2004 Rueger et al.
6,861,404 B1 3/2005 Cohen et al.
6,949,505 B1 9/2005 Rueger et al.
7,390,780 B2 6/2008 Huang et al.
8,772,009 B2 7/2014 Doyon
10,501,404 B1 12/2019 Angel et al.
11,241,505 B2 2/2022 Angel et al.
2012/0060230 A1 3/2012 Collingwood et al.
2012/0270273 A1* 10/2012 Zhang .................. C07K 14/195 536/23.4
2013/0149780 A1 6/2013 Zhang et al.
2018/0177893 A1* 6/2018 Angel ...................... A61P 9/00
2018/0256748 A1 9/2018 Angel et al.
2019/0338273 A1 11/2019 Duchateau et al.
2019/0359959 A1 11/2019 Jaenisch et al.
2019/0390174 A1 12/2019 Angel et al.

FOREIGN PATENT DOCUMENTS

WO WO-2012015938 A2 * 2/2012 ......... C07K 14/4702
WO WO-2012138927 A2 10/2012
WO WO-2014145599 A2 9/2014
WO WO-2018007263 A1 * 1/2018 ............. A61P 37/04
WO WO-2021231549 A2 11/2021

OTHER PUBLICATIONS

Hoynes-O'Connor, et al. De novo design of heat-repressible RNA thermosensors in *E. coli*. Nucleic Acids Research. 2015; 43(12): 6166-79. (Year: 2015).*
Wennborg, et al. A human RNase E-like activity that cleaves RNA sequences involved in mRNA stability control. Proceedings of National Academy of Sciences. 1995; 92: 7322-26. (Year: 1995).*
Galloway and Cowling. mRNA cap regulation in mammalian cell function and fate. Biochimica et Biophysica Acta: Gene Regulatory Mechanisms. 2019:270-79. (Year: 2019).*
Yanik, et al. In vivo genome editing as a potential treatment strategy for inherited retinal dystrophies. Progress in Retinal and Eye Research. 2017:1-18. (Year: 2017).*
Plensdorf, et al. Pigmentation Disorders: Diagnosis and Management. American Family Physician. 2017; 96(12):797-804. (Year: 2017).*
Sundar, et al. Cryocompression for enhanced limb hypothermia in preventing paclitaxel-induced peripheral neuropathy. Journal of Clinical Oncology. Meeting Abstract (2018 ASCO Annual Meeting). 2018; 36:1-2. (Year: 2018).*
Berge, Stephen M. et al. Pharmaceutical Salts. Journal of Pharmaceutical Sciences 66(1):1-19 (1977).
EP2021803274.6 Partial European Search Report dated Jun. 5, 2024.
Gennaro, Alfonso R. Remington: Practice of the Science and Pharmacy, 19th Edition. Mack Publishing Company (1995).
PCT/US2021/031956 International Preliminary Report on Patentability dated Nov. 15, 2022.
PCT/US2021/031956 International Search Report and Written Opinion dated Nov. 26, 2021.
PCT/US2021/031956 Invitation to Pay Additional Fees dated Sep. 9, 2021.

(Continued)

*Primary Examiner* — Allison M Fox
*Assistant Examiner* — Gina Pronzati
(74) *Attorney, Agent, or Firm* — Wilson Sonsini Goodrich & Rosati

(57) ABSTRACT

The present invention relates in part to nucleic acids encoding gene editing proteins, including novel engineered variants.

22 Claims, 21 Drawing Sheets

Specification includes a Sequence Listing.

(56) References Cited

OTHER PUBLICATIONS

Stahl, P Heinrich, and Camille G. Wermuth. Handbook of Pharmaceutical Salts: Properties, Selection, and Use. Verlag Helvetica Chimica Acta and Wiley-VCH (2002).
Third Party Observation dated Jan. 20, 2022 for International Application No. PCT/US2021/031956.
Wah, David A. et al. Structure of Fokl has implications for DNA cleavage. Proceedings of the National Academy of Sciences 95(18):10564-10569 (1998).
Yang, Zhang. et al. Fast and sensitive detection of indels induced by precise gene targeting. Nucleic acids research 43(9):e59, 1-8 (2015).
EP21803274.6 Extended European Search Report dated Aug. 30, 2024.

* cited by examiner

FIG. 1

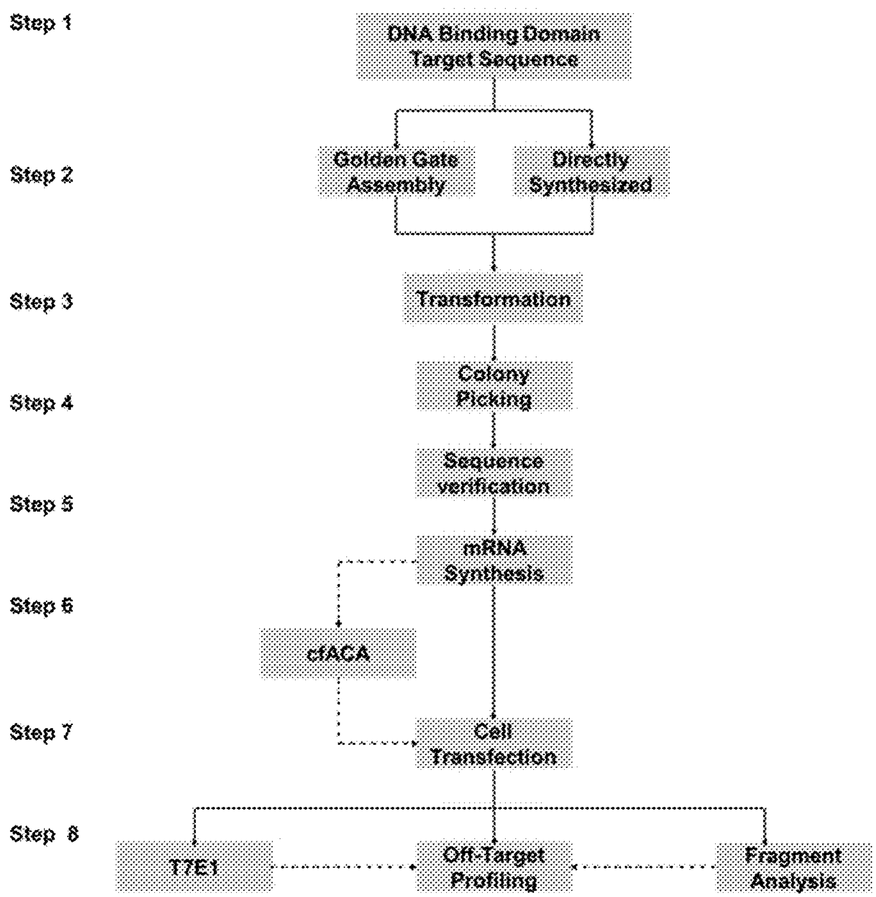

Kits Used by step

| Step | Kit |
|---|---|
| 1 | - |
| 2 | Golden Gate Assembly- NEB Enzymes |
| | Second Party Gene Synthesis |
| 3 | NEB Stable Competent E. coli (High Efficiency) (Cat. No. C3040H) |
| 4 | - |
| 5 | GeneWiz Plasmid Sequencing |
| 6 | NEB T7 RNA Synthesis (Cat. No. E2040) |
| Optional 6.5 | Cell-Free Amplicon Cutting Assay utalizing Promega Rabbit Reticulocyte Lysate (Cat. No. L4960) |
| 7 | Synthetic mRNA is transfected using the ThermoFisher Neon Transfection System, ThermoFisher Lipofectamine 3000, or ToRNAdoTM.. Cells will be later extracted using a Promega Maxwell® RSC Cultured Cells DNA Kit (cat. No. AS1620), Qiagen QIAamp DNA Micro or Mini Kit (cat. No. 56304 or 51306), or Zymo Quick-DNA Miniprep Kit (cat. No. D3024). |
| 8 | T7E1 Mismatch assay- KapaBiosystems HiFi HotStart PCR Kit (cat. No KK2502) followed by NEB T7 Endonuclease I (Cat. No. M0302L) |
| | Novel Off-Target Assay |
| | Fragment Analysis by GeneWiz |

FIG. 3C

| Col7A1E73 Spacing Chart | | | | | |
|---|---|---|---|---|---|
| | NS R1 20mer | NSR2 20mer | NSR3 18mer | NSR4 18mer | NSR5 16mer |
| NSL1 20mer | 18 | 16 | 31 | 4 | 6 |
| NSL2 20mer | 20 | 18 | 33 | 6 | 8 |
| NSL3 18mer | 5 | 3 | 18 | -8 | -5 |
| NSL4 19mer | 32 | 30 | 45 | 18 | 20 |
| NSL5 18mer | 0 | 24 | 39 | 12 | 14 |
| NSL6 18mer | 28 | 26 | 41 | 14 | 16 |
| NSL7 18mer | 20 | 18 | 33 | 6 | 8 |

FIG. 7A

| Alias | Sequence | SEQ ID No. |
|---|---|---|
| NS_Mod_1 | AHDG | SEQ ID NO: 43 |
| NS_Mod_2 | GAHD | SEQ ID NO: 42 |
| NS_Mod_3 | GTHG | SEQ ID NO: 62 |
| NS_Mod_4 | GSGS | SEQ ID NO: 63 |
| NS_Mod_5 | NHGG | SEQ ID NO: 60 |
| NS_Mod_6 | GSGG | SEQ ID NO: 64 |
| NS_Mod_7 | RDHG | SEQ ID NO: 55 |
| NS_Mod_8 | IVHG | SEQ ID NO: 52 |
| NS_Mod_9 | VHGA | SEQ ID NO: 51 |
| NS_Mod_10 | GHGP | SEQ ID NO: 46 |
| NS_Mod_11 | RHGD | SEQ ID NO: 54 |
| NS_Mod_12 | THGG | SEQ ID NO: 61 |
| NS_Mod_13 | GGHD | SEQ ID NO: 41 |
| NS_Mod_14 | PHGG | SEQ ID NO: 47 |
| NS_Mod_15 | LHGA | SEQ ID NO: 50 |
| NS_Mod_16 | GGGG | SEQ ID NO: 65 |
| NS_Mod_17 | GRGG | SEQ ID NO: 66 |
| NS_Mod_18 | RHGE | SEQ ID NO: 56 |
| NS_Mod_19 | AHGA | SEQ ID NO: 49 |
| NS_Mod_20 | HRGE | SEQ ID NO: 57 |
| NS_Mod_21 | PHDG | SEQ ID NO: 44 |
| NS_Mod_22 | GPHD | SEQ ID NO: 45 |
| NS_Mod_23 | GKGG | SEQ ID NO: 67 |
| NS_Mod_24 | PHGP | SEQ ID NO: 48 |
| NS_Mod_25 | IHGM | SEQ ID NO: 53 |
| NS_Mod_26 | GPYE | SEQ ID NO: 59 |

SEQUENCE LISTING

```
Sequence total quantity: 89
SEQ ID NO: 1            moltype = AA  length = 7
FEATURE                 Location/Qualifiers
REGION                  1..7
                        note = Synthetic Sequence
source                  1..7
                        mol_type = protein
                        organism = synthetic construct
SEQUENCE: 1
GGRPALE                                                                  7

SEQ ID NO: 2            moltype = AA  length = 7
FEATURE                 Location/Qualifiers
REGION                  1..7
                        note = Synthetic Sequence
source                  1..7
                        mol_type = protein
                        organism = synthetic construct
SEQUENCE: 2
GGKQALE                                                                  7

SEQ ID NO: 3            moltype = AA  length = 21
FEATURE                 Location/Qualifiers
REGION                  1..21
                        note = Synthetic Sequence
source                  1..21
                        mol_type = protein
                        organism = synthetic construct
SEQUENCE: 3
GGKQALETVQ RLLPVLCQDH G                                                  21

SEQ ID NO: 4            moltype = AA  length = 21
FEATURE                 Location/Qualifiers
REGION                  1..21
                        note = Synthetic Sequence
source                  1..21
                        mol_type = protein
                        organism = synthetic construct
SEQUENCE: 4
GGKQALETVQ RLLPVLCQAH G                                                  21

SEQ ID NO: 5            moltype = AA  length = 20
FEATURE                 Location/Qualifiers
REGION                  1..20
                        note = Synthetic Sequence
source                  1..20
                        mol_type = protein
                        organism = synthetic construct
SEQUENCE: 5
GKQALETVQR LLPVLCQDHG                                                    20

SEQ ID NO: 6            moltype = AA  length = 20
FEATURE                 Location/Qualifiers
REGION                  1..20
                        note = Synthetic Sequence
source                  1..20
                        mol_type = protein
                        organism = synthetic construct
SEQUENCE: 6
GKQALETVQR LLPVLCQAHG                                                    20

SEQ ID NO: 7            moltype = AA  length = 19
FEATURE                 Location/Qualifiers
REGION                  1..19
                        note = Synthetic Sequence
source                  1..19
                        mol_type = protein
                        organism = synthetic construct
SEQUENCE: 7
GGKQALETVQ RLLPVLCQD                                                     19

SEQ ID NO: 8            moltype = AA  length = 19
FEATURE                 Location/Qualifiers
REGION                  1..19
                        note = Synthetic Sequence
source                  1..19
                        mol_type = protein
                        organism = synthetic construct
```

-continued

```
SEQUENCE: 8
GGKQALETVQ RLLPVLCQA                                          19

SEQ ID NO: 9             moltype = AA  length = 18
FEATURE                  Location/Qualifiers
REGION                   1..18
                         note = Synthetic Sequence
source                   1..18
                         mol_type = protein
                         organism = synthetic construct
SEQUENCE: 9
GKQALETVQR LLPVLCQD                                           18

SEQ ID NO: 10            moltype = AA  length = 18
FEATURE                  Location/Qualifiers
REGION                   1..18
                         note = Synthetic Sequence
source                   1..18
                         mol_type = protein
                         organism = synthetic construct
SEQUENCE: 10
GKQALETVQR LLPVLCQA                                           18

SEQ ID NO: 11            moltype = AA  length = 15
FEATURE                  Location/Qualifiers
REGION                   1..15
                         note = Synthetic Sequence
SITE                     4
                         note = MISC_FEATURE - X at this position in the sequence is
                          referred to as "v" in theSpecification for this sequence,
                          and v is Q, D or E.
SITE                     11
                         note = MISC_FEATURE - X at this position for this sequence
                          is referred to as "w" in theSpecification for this
                          sequence, and w is S or N.
SITE                     12
                         note = MISC_FEATURE - X at this position for this sequence
                          is referred to as "x" in theSpecification for this
                          sequence, and x is I, H, N, or I.
SITE                     13
                         note = MISC_FEATURE - X at this position for this sequence
                          is referred to as "y" in theSpecification for this
                          sequence, and y is D, A, I, N, H, K, S, orG.
SITE                     14
                         note = MISC_FEATURE - X at this position for this sequence
                          is referred to as "z" in theSpecification for this
                          sequence, and z can be any naturallyoccurring amino acid.
SITE                     15
                         note = MISC_FEATURE - Xaa can be any naturally occurring
                          amino acid.
source                   1..15
                         mol_type = protein
                         organism = synthetic construct
SEQUENCE: 11
LTPXQVVAIA XXXXX                                              15

SEQ ID NO: 12            moltype = AA  length = 14
FEATURE                  Location/Qualifiers
REGION                   1..14
                         note = Synthetic Sequence
SITE                     4
                         note = MISC_FEATURE - X at this position for this sequence
                          is referred to as "v" in theSpecification for this
                          sequence, and v is Q, D or E.
SITE                     11
                         note = MISC_FEATURE - X at this position for this sequence
                          is referred to as "w" in theSpecification for this
                          sequence, and w is S or N.
SITE                     12
                         note = MISC_FEATURE - X at this position for this sequence
                          is referred to as "x" in theSpecification for this
                          sequence, and x is I, H, N, or I.
SITE                     13
                         note = MISC_FEATURE - X at this position for this sequence
                          is referred to as "y" in theSpecification for this
                          sequence, and y is D, A, I, N, H, K, S, orG.
SITE                     14
                         note = MISC_FEATURE - Xaa can be any naturally occurring
                          amino acid.
```

-continued

```
source                1..14
                      mol_type = protein
                      organism = synthetic construct
SEQUENCE: 12
LTPXQVVAIA XXXX                                                            14

SEQ ID NO: 13         moltype = AA  length = 16
FEATURE               Location/Qualifiers
REGION                1..16
                      note = Synthetic Sequence
SITE                  4
                      note = MISC_FEATURE - X at this position for this sequence
                       is referred to as "v" in theSpecification for this
                       sequence, and v is D or E.
SITE                  11
                      note = MISC_FEATURE - X at this position for this sequence
                       is referred to as "w" in theSpecification for this
                       sequence, and w is S or N.
SITE                  12
                      note = MISC_FEATURE - X at this position for this sequence
                       is referred to as "x" in theSpecification for this
                       sequence, and x is N, H, or I.
SITE                  13
                      note = MISC_FEATURE - X at this position for this sequence
                       is referred to as "y" in theSpecification for this
                       sequence, and y can be any naturallyoccurring amino acid.
SITE                  14
                      note = MISC_FEATURE - Xaa can be any naturally occurring
                       amino acid.
source                1..16
                      mol_type = protein
                      organism = synthetic construct
SEQUENCE: 13
LTPXQVVAIA XXXXHG                                                          16

SEQ ID NO: 14         moltype = AA  length = 16
FEATURE               Location/Qualifiers
REGION                1..16
                      note = Synthetic Sequence
SITE                  4
                      note = MISC_FEATURE - X at this position for this sequence
                       is referred to as "v" in theSpecification for this
                       sequence, and v is D or E.
SITE                  11
                      note = MISC_FEATURE - X at this position for this sequence
                       is referred to as "w" in theSpecification for this
                       sequence, and w is S or N.
SITE                  12
                      note = MISC_FEATURE - X at this position for this sequence
                       is referred to as "x" in theSpecification for this
                       sequence, and x is N, H or I.
SITE                  13
                      note = MISC_FEATURE - X at this position for this sequence
                       is referred to as "y" in theSpecification for this
                       sequence, and y is D, A, I, N, H, K, S, orG.
SITE                  14
                      note = MISC_FEATURE - Xaa can be any naturally occurring
                       amino acid.
source                1..16
                      mol_type = protein
                      organism = synthetic construct
SEQUENCE: 14
LTPXQVVAIA XXXXHG                                                          16

SEQ ID NO: 15         moltype = AA  length = 16
FEATURE               Location/Qualifiers
REGION                1..16
                      note = Synthetic Sequence
SITE                  4
                      note = MISC_FEATURE - X at this position for this sequence
                       is referred to as "v" in theSpecification for this
                       sequence, and v is D or E.
SITE                  11
                      note = MISC_FEATURE - X at this position for this sequence
                       is referred to as "w" in theSpecification for this
                       sequence, and w is S or N.
SITE                  12
                      note = MISC_FEATURE - X at this position for this sequence
                       is referred to as "x" in theSpecification for this
```

-continued

```
                         sequence, and x is any amino acid otherthan N, H and I.
SITE                    13
                        note = MISC_FEATURE - Xaa can be any naturally occurring
                         amino acid.
SITE                    14
                        note = MISC_FEATURE - Xaa can be any naturally occurring
                         amino acid.
source                  1..16
                        mol_type = protein
                        organism = synthetic construct
SEQUENCE: 15
LTPXQVVAIA XXXXHG                                                             16

SEQ ID NO: 16           moltype = AA  length = 16
FEATURE                 Location/Qualifiers
REGION                  1..16
                        note = Synthetic Sequence
SITE                    4
                        note = MISC_FEATURE - X at this position for this sequence
                         is referred to as "v" in theSpecification for this
                         sequence, and v is D or E.
SITE                    12
                        note = MISC_FEATURE - X at this position for this sequence
                         is referred to as "w" in theSpecification for this
                         sequence, and w is S or N.
SITE                    13
                        note = MISC_FEATURE - X at this position for this sequence
                         is referred to as "y" in theSpecification for this
                         sequence, and y is any amino acid otherthan G.
SITE                    14
                        note = MISC_FEATURE - Xaa can be any naturally occurring
                         amino acid.
source                  1..16
                        mol_type = protein
                        organism = synthetic construct
SEQUENCE: 16
LTPXQVVAIA IXXXHG                                                             16

SEQ ID NO: 17           moltype = AA  length = 16
FEATURE                 Location/Qualifiers
REGION                  1..16
                        note = Synthetic Sequence
SITE                    4
                        note = MISC_FEATURE - X at this position for this sequence
                         is referred to as "v" in theSpecification for this
                         sequence, and v is D or E.
SITE                    11
                        note = MISC_FEATURE - X at this position for this sequence
                         is referred to as "w" in theSpecification for this
                         sequence, and w is S or N.
SITE                    12
                        note = MISC_FEATURE - X at this position for this sequence
                         is referred to as "x" in theSpecification for this
                         sequence, and x is S, T or Q.
SITE                    13
                        note = MISC_FEATURE - Xaa can be any naturally occurring
                         amino acid.
SITE                    14
                        note = MISC_FEATURE - Xaa can be any naturally occurring
                         amino acid.
source                  1..16
                        mol_type = protein
                        organism = synthetic construct
SEQUENCE: 17
LTPXQVVAIA XXXXHG                                                             16

SEQ ID NO: 18           moltype = AA  length = 16
FEATURE                 Location/Qualifiers
REGION                  1..16
                        note = Synthetic Sequence
SITE                    4
                        note = MISC_FEATURE - X at this position for this sequence
                         is referred to as "v" in theSpecification for this
                         sequence, and v is D or E.
SITE                    11
                        note = MISC_FEATURE - X at this position for this sequence
                         is referred to as "w" in theSpecification for this
                         sequence, and w is S or N.
SITE                    12
```

-continued

```
                        note = MISC_FEATURE - X at this position for this sequence
                         is referred to as "x" in theSpecification for this
                         sequence, and x is S, T or Q.
SITE                    13
                        note = MISC_FEATURE - X at this position for this sequence
                         is referred to as "y" in theSpecification for this
                         sequence, and y is D, A, I, N, H, K, S, orG.
SITE                    14
                        note = MISC_FEATURE - Xaa can be any naturally occurring
                         amino acid.
source                  1..16
                        mol_type = protein
                        organism = synthetic construct
SEQUENCE: 18
LTPXQVVAIA XXXXHG                                                            16

SEQ ID NO: 19           moltype = AA  length = 12
FEATURE                 Location/Qualifiers
REGION                  1..12
                        note = Synthetic Sequence
SITE                    4
                        note = MISC_FEATURE - X at this position for this sequence
                         is referred to as "v" in theSpecification for this
                         sequence, and v is D or E.
SITE                    11
                        note = MISC_FEATURE - X at this position for this sequence
                         is referred to as "w" in theSpecification for this
                         sequence, and w is S or N.
SITE                    12
                        note = MISC_FEATURE - X at this position for this sequence
                         is referred to as "x" in theSpecification for this
                         sequence, and x is S, T or Q.
source                  1..12
                        mol_type = protein
                        organism = synthetic construct
SEQUENCE: 19
LTPXQVVAIA XX                                                                12

SEQ ID NO: 20           moltype = AA  length = 13
FEATURE                 Location/Qualifiers
REGION                  1..13
                        note = Synthetic Sequence
SITE                    4
                        note = MISC_FEATURE - X at this position for this sequence
                         is referred to as "v" in theSpecification for this
                         sequence, and v is D or E.
SITE                    11
                        note = MISC_FEATURE - X at this position for this sequence
                         is referred to as "w" in theSpecification for this
                         sequence, and w is S or N.
SITE                    12
                        note = MISC_FEATURE - X at this position for this sequence
                         is referred to as "x" in theSpecification for this
                         sequence, and x is S, T or Q.
SITE                    13
                        note = MISC_FEATURE - X at this position for this sequence
                         is referred to as "y" in theSpecification for this
                         sequence, and y is D, A, I, N, H, K, S, orG.
source                  1..13
                        mol_type = protein
                        organism = synthetic construct
SEQUENCE: 20
LTPXQVVAIA XXX                                                               13

SEQ ID NO: 21           moltype = AA  length = 18
FEATURE                 Location/Qualifiers
REGION                  1..18
                        note = Synthetic Sequence
SITE                    4
                        note = MISC_FEATURE - X at this position for this sequence
                         is referred to as "v" in theSpecification for this
                         sequence, and v is Q, D or E.
SITE                    11
                        note = MISC_FEATURE - X at this position for this sequence
                         is referred to as "w" in theSpecification for this
                         sequence, and w is S or N.
SITE                    12
                        note = MISC_FEATURE - X at this position for this sequence
                         is referred to as "x" in theSpecification for this
```

-continued

```
                        sequence, and x is N, H or I.
SITE                    13
                        note = MISC_FEATURE - Xaa can be any naturally occurring
                         amino acid.
SITE                    14
                        note = MISC_FEATURE - Xaa can be any naturally occurring
                         amino acid.
source                  1..18
                        mol_type = protein
                        organism = synthetic construct
SEQUENCE: 21
LTPXQVVAIA XXXXGHGG                                              18

SEQ ID NO: 22           moltype = AA  length = 18
FEATURE                 Location/Qualifiers
REGION                  1..18
                        note = Synthetic Sequence
SITE                    4
                        note = MISC_FEATURE - X at this position for this sequence
                         is referred to as "v" in theSpecification for this
                         sequence, and v is Q, D or E.
SITE                    11
                        note = MISC_FEATURE - X at this position for this sequence
                         is referred to as "w" in theSpecification for this
                         sequence, and w is S or N.
SITE                    12
                        note = MISC_FEATURE - X at this position for this sequence
                         is referred to as "x" in theSpecification for this
                         sequence, and x is N, H, or I.
SITE                    13
                        note = MISC_FEATURE - X at this position for this sequence
                         is referred to as "y" in theSpecification for this
                         sequence, and y is D, A, I, N, H, K, S, orG.
SITE                    14
                        note = MISC_FEATURE - Xaa can be any naturally occurring
                         amino acid.
source                  1..18
                        mol_type = protein
                        organism = synthetic construct
SEQUENCE: 22
LTPXQVVAIA XXXXGHGG                                              18

SEQ ID NO: 23           moltype = AA  length = 18
FEATURE                 Location/Qualifiers
REGION                  1..18
                        note = Synthetic Sequence
SITE                    4
                        note = MISC_FEATURE - X at this position for this sequence
                         is referred to as "v" in theSpecification for this
                         sequence, and v is Q, D or E.
SITE                    11
                        note = MISC_FEATURE - X at this position for this sequence
                         is referred to as "w" in theSpecification for this
                         sequence, and w is S or N.
SITE                    12
                        note = MISC_FEATURE - X at this position for this sequence
                         is referred to as "x" in theSpecification for this
                         sequence, and x is any amino acid otherthan N, H and I.
SITE                    13
                        note = MISC_FEATURE - Xaa can be any naturally occurring
                         amino acid.
SITE                    14
                        note = MISC_FEATURE - Xaa can be any naturally occurring
                         amino acid.
source                  1..18
                        mol_type = protein
                        organism = synthetic construct
SEQUENCE: 23
LTPXQVVAIA XXXXGHGG                                              18

SEQ ID NO: 24           moltype = AA  length = 18
FEATURE                 Location/Qualifiers
REGION                  1..18
                        note = Synthetic Sequence
SITE                    4
                        note = MISC_FEATURE - X at this position for this sequence
                         is referred to as "v" in theSpecification for this
                         sequence, and v is Q, D or E.
SITE                    11
```

```
                         note = MISC_FEATURE - X at this position for this sequence
                          is referred to as "w" in theSpecification for this
                          sequence, and w is S or N.
SITE                     13
                         note = MISC_FEATURE - X at this position for this sequence
                          is referred to as "y" in theSpecification for this
                          sequence, and y is any amino acid otherthan G.
SITE                     14
                         note = MISC_FEATURE - Xaa can be any naturally occurring
                          amino acid.
source                   1..18
                         mol_type = protein
                         organism = synthetic construct
SEQUENCE: 24
LTPXQVVAIA XIXXGHGG                                                    18

SEQ ID NO: 25            moltype = AA  length = 18
FEATURE                  Location/Qualifiers
REGION                   1..18
                         note = Synthetic Sequence
SITE                     4
                         note = MISC_FEATURE - X at this position for this sequence
                          is referred to as "v" in theSpecification for this
                          sequence, and v is Q, D or E.
SITE                     11
                         note = MISC_FEATURE - X at this position for this sequence
                          is referred to as "w" in theSpecification for this
                          sequence, and w is S or N.
SITE                     14
                         note = MISC_FEATURE - Xaa can be any naturally occurring
                          amino acid.
source                   1..18
                         mol_type = protein
                         organism = synthetic construct
SEQUENCE: 25
LTPXQVVAIA XIAXGHGG                                                    18

SEQ ID NO: 26            moltype = AA  length = 18
FEATURE                  Location/Qualifiers
REGION                   1..18
                         note = Synthetic Sequence
SITE                     4
                         note = MISC_FEATURE - X at this position for this sequence
                          is referred to as "v" in theSpecification for this
                          sequence, and v is Q, D or E.
SITE                     11
                         note = MISC_FEATURE - X at this position for this sequence
                          is referred to as "w" in theSpecification for this
                          sequence, and w is S or N.
SITE                     12
                         note = MISC_FEATURE - X at this position for this sequence
                          is referred to as "x" in theSpecification for this
                          sequence, and x is S, T or Q.
SITE                     13
                         note = MISC_FEATURE - Xaa can be any naturally occurring
                          amino acid.
SITE                     14
                         note = MISC_FEATURE - Xaa can be any naturally occurring
                          amino acid.
source                   1..18
                         mol_type = protein
                         organism = synthetic construct
SEQUENCE: 26
LTPXQVVAIA XXXXGHGG                                                    18

SEQ ID NO: 27            moltype = AA  length = 18
FEATURE                  Location/Qualifiers
REGION                   1..18
                         note = Synthetic Sequence
SITE                     4
                         note = MISC_FEATURE - X at this position for this sequence
                          is referred to as "v" in theSpecification for this
                          sequence, and v is Q, D or E.
SITE                     11
                         note = MISC_FEATURE - X at this position for this sequence
                          is referred to as "w" in theSpecification for this
                          sequence, and w is S or N.
SITE                     12
                         note = MISC_FEATURE - X at this position for this sequence
```

```
                          is referred to as "x" in theSpecification for this
                          sequence, and x is S, T, or Q.
SITE                     13
                         note = MISC_FEATURE - X at this position for this sequence
                          is referred to as "y" in theSpecification for this
                          sequence, and y is D, A, I, N, H, K, S, orG.
SITE                     14
                         note = MISC_FEATURE - Xaa can be any naturally occurring
                          amino acid.
source                   1..18
                         mol_type = protein
                         organism = synthetic construct
SEQUENCE: 27
LTPXQVVAIA XXXXGHGG                                                        18

SEQ ID NO: 28            moltype = AA  length = 13
FEATURE                  Location/Qualifiers
REGION                   1..13
                         note = Synthetic Sequence
SITE                     4
                         note = MISC_FEATURE - X at this position for this sequence
                          is referred to as "v" in theSpecification for this
                          sequence, and v is Q, D or E.
SITE                     11
                         note = MISC_FEATURE - X at this position for this sequence
                          is referred to as "w" in theSpecification for this
                          sequence, and w is S or N.
SITE                     12
                         note = MISC_FEATURE - X at this position for this sequence
                          is referred to as "x" in theSpecification for this
                          sequence, and x is S, T or Q.
SITE                     13
                         note = MISC_FEATURE - X at this position for this sequence
                          is referred to as "y" in theSpecification for this
                          sequence, and y is D, A, I, N, H, K, S, orG.
source                   1..13
                         mol_type = protein
                         organism = synthetic construct
SEQUENCE: 28
LTPXQVVAIA XXX                                                             13

SEQ ID NO: 29            moltype = AA  length = 14
FEATURE                  Location/Qualifiers
REGION                   1..14
                         note = Synthetic Sequence
source                   1..14
                         mol_type = protein
                         organism = synthetic construct
SEQUENCE: 29
IVGVGKQWSG ARAL                                                            14

SEQ ID NO: 30            moltype = AA  length = 14
FEATURE                  Location/Qualifiers
REGION                   1..14
                         note = Synthetic Sequence
source                   1..14
                         mol_type = protein
                         organism = synthetic construct
SEQUENCE: 30
IVGVGKQKRG ARAL                                                            14

SEQ ID NO: 31            moltype = AA  length = 18
FEATURE                  Location/Qualifiers
REGION                   1..18
                         note = Synthetic Sequence
source                   1..18
                         mol_type = protein
                         organism = synthetic construct
SEQUENCE: 31
IVGVGGSKRG AGSGARAL                                                        18

SEQ ID NO: 32            moltype = AA  length = 8
FEATURE                  Location/Qualifiers
REGION                   1..8
                         note = Synthetic Sequence
source                   1..8
                         mol_type = protein
                         organism = synthetic construct
SEQUENCE: 32
```

-continued

```
GSKRGAGS                                                        8

SEQ ID NO: 33          moltype = AA  length = 37
FEATURE                Location/Qualifiers
REGION                 1..37
                       note = Synthetic Sequence
source                 1..37
                       mol_type = protein
                       organism = synthetic construct
SEQUENCE: 33
LTPEQVVAIA SRVDGGKQAL ETVQRLLPVL CQAGHGG                        37

SEQ ID NO: 34          moltype = DNA  length = 20
FEATURE                Location/Qualifiers
misc_feature           1..20
                       note = Synthetic Sequence
source                 1..20
                       mol_type = other DNA
                       organism = synthetic construct
SEQUENCE: 34
tgtacagcca ccagcattct                                           20

SEQ ID NO: 35          moltype = DNA  length = 20
FEATURE                Location/Qualifiers
misc_feature           1..20
                       note = Synthetic Sequence
source                 1..20
                       mol_type = other DNA
                       organism = synthetic construct
SEQUENCE: 35
tccaggaaag ccgatggggc                                           20

SEQ ID NO: 36          moltype = DNA  length = 20
FEATURE                Location/Qualifiers
misc_feature           1..20
                       note = Synthetic Sequence
source                 1..20
                       mol_type = other DNA
                       organism = synthetic construct
SEQUENCE: 36
gtacagccac cagcattctc                                           20

SEQ ID NO: 37          moltype = DNA  length = 20
FEATURE                Location/Qualifiers
misc_feature           1..20
                       note = Synthetic Sequence
source                 1..20
                       mol_type = other DNA
                       organism = synthetic construct
SEQUENCE: 37
ctccaggaaa gccgatgggg                                           20

SEQ ID NO: 38          moltype = AA  length = 4
FEATURE                Location/Qualifiers
REGION                 1..4
                       note = Synthetic Sequence
source                 1..4
                       mol_type = protein
                       organism = synthetic construct
SEQUENCE: 38
GHGG                                                            4

SEQ ID NO: 39          moltype = AA  length = 4
FEATURE                Location/Qualifiers
REGION                 1..4
                       note = Synthetic Sequence
source                 1..4
                       mol_type = protein
                       organism = synthetic construct
SEQUENCE: 39
HGSG                                                            4

SEQ ID NO: 40          moltype = AA  length = 4
FEATURE                Location/Qualifiers
REGION                 1..4
                       note = Synthetic Sequence
source                 1..4
                       mol_type = protein
                       organism = synthetic construct
```

-continued

```
SEQUENCE: 40
HGGG                                                                    4

SEQ ID NO: 41          moltype = AA  length = 4
FEATURE                Location/Qualifiers
REGION                 1..4
                       note = Synthetic Sequence
source                 1..4
                       mol_type = protein
                       organism = synthetic construct
SEQUENCE: 41
GGHD                                                                    4

SEQ ID NO: 42          moltype = AA  length = 4
FEATURE                Location/Qualifiers
REGION                 1..4
                       note = Synthetic Sequence
source                 1..4
                       mol_type = protein
                       organism = synthetic construct
SEQUENCE: 42
GAHD                                                                    4

SEQ ID NO: 43          moltype = AA  length = 4
FEATURE                Location/Qualifiers
REGION                 1..4
                       note = Synthetic Sequence
source                 1..4
                       mol_type = protein
                       organism = synthetic construct
SEQUENCE: 43
AHDG                                                                    4

SEQ ID NO: 44          moltype = AA  length = 4
FEATURE                Location/Qualifiers
REGION                 1..4
                       note = Synthetic Sequence
source                 1..4
                       mol_type = protein
                       organism = synthetic construct
SEQUENCE: 44
PHDG                                                                    4

SEQ ID NO: 45          moltype = AA  length = 4
FEATURE                Location/Qualifiers
REGION                 1..4
                       note = Synthetic Sequence
source                 1..4
                       mol_type = protein
                       organism = synthetic construct
SEQUENCE: 45
GPHD                                                                    4

SEQ ID NO: 46          moltype = AA  length = 4
FEATURE                Location/Qualifiers
REGION                 1..4
                       note = Synthetic Sequence
source                 1..4
                       mol_type = protein
                       organism = synthetic construct
SEQUENCE: 46
GHGP                                                                    4

SEQ ID NO: 47          moltype = AA  length = 4
FEATURE                Location/Qualifiers
REGION                 1..4
                       note = Synthetic Sequence
source                 1..4
                       mol_type = protein
                       organism = synthetic construct
SEQUENCE: 47
PHGG                                                                    4

SEQ ID NO: 48          moltype = AA  length = 4
FEATURE                Location/Qualifiers
REGION                 1..4
                       note = Synthetic Sequence
source                 1..4
                       mol_type = protein
```

```
                        organism = synthetic construct
SEQUENCE: 48
PHGP                                                                          4

SEQ ID NO: 49           moltype = AA  length = 4
FEATURE                 Location/Qualifiers
REGION                  1..4
                        note = Synthetic Sequence
source                  1..4
                        mol_type = protein
                        organism = synthetic construct
SEQUENCE: 49
AHGA                                                                          4

SEQ ID NO: 50           moltype = AA  length = 4
FEATURE                 Location/Qualifiers
REGION                  1..4
                        note = Synthetic Sequence
source                  1..4
                        mol_type = protein
                        organism = synthetic construct
SEQUENCE: 50
LHGA                                                                          4

SEQ ID NO: 51           moltype = AA  length = 4
FEATURE                 Location/Qualifiers
REGION                  1..4
                        note = Synthetic Sequence
source                  1..4
                        mol_type = protein
                        organism = synthetic construct
SEQUENCE: 51
VHGA                                                                          4

SEQ ID NO: 52           moltype = AA  length = 4
FEATURE                 Location/Qualifiers
REGION                  1..4
                        note = Synthetic Sequence
source                  1..4
                        mol_type = protein
                        organism = synthetic construct
SEQUENCE: 52
IVHG                                                                          4

SEQ ID NO: 53           moltype = AA  length = 4
FEATURE                 Location/Qualifiers
REGION                  1..4
                        note = Synthetic Sequence
source                  1..4
                        mol_type = protein
                        organism = synthetic construct
SEQUENCE: 53
IHGM                                                                          4

SEQ ID NO: 54           moltype = AA  length = 4
FEATURE                 Location/Qualifiers
REGION                  1..4
                        note = Synthetic Sequence
source                  1..4
                        mol_type = protein
                        organism = synthetic construct
SEQUENCE: 54
RHGD                                                                          4

SEQ ID NO: 55           moltype = AA  length = 4
FEATURE                 Location/Qualifiers
REGION                  1..4
                        note = Synthetic Sequence
source                  1..4
                        mol_type = protein
                        organism = synthetic construct
SEQUENCE: 55
RDHG                                                                          4

SEQ ID NO: 56           moltype = AA  length = 4
FEATURE                 Location/Qualifiers
REGION                  1..4
                        note = Synthetic Sequence
source                  1..4
```

-continued

```
                        mol_type = protein
                        organism = synthetic construct
SEQUENCE: 56
RHGE                                                                        4

SEQ ID NO: 57           moltype = AA  length = 4
FEATURE                 Location/Qualifiers
REGION                  1..4
                        note = Synthetic Sequence
source                  1..4
                        mol_type = protein
                        organism = synthetic construct
SEQUENCE: 57
HRGE                                                                        4

SEQ ID NO: 58           moltype = AA  length = 4
FEATURE                 Location/Qualifiers
REGION                  1..4
                        note = Synthetic Sequence
source                  1..4
                        mol_type = protein
                        organism = synthetic construct
SEQUENCE: 58
HRGD                                                                        4

SEQ ID NO: 59           moltype = AA  length = 4
FEATURE                 Location/Qualifiers
REGION                  1..4
                        note = Synthetic Sequence
source                  1..4
                        mol_type = protein
                        organism = synthetic construct
SEQUENCE: 59
GPYE                                                                        4

SEQ ID NO: 60           moltype = AA  length = 4
FEATURE                 Location/Qualifiers
REGION                  1..4
                        note = Synthetic Sequence
source                  1..4
                        mol_type = protein
                        organism = synthetic construct
SEQUENCE: 60
NHGG                                                                        4

SEQ ID NO: 61           moltype = AA  length = 4
FEATURE                 Location/Qualifiers
REGION                  1..4
                        note = Synthetic Sequence
source                  1..4
                        mol_type = protein
                        organism = synthetic construct
SEQUENCE: 61
THGG                                                                        4

SEQ ID NO: 62           moltype = AA  length = 4
FEATURE                 Location/Qualifiers
REGION                  1..4
                        note = Synthetic Sequence
source                  1..4
                        mol_type = protein
                        organism = synthetic construct
SEQUENCE: 62
GTHG                                                                        4

SEQ ID NO: 63           moltype = AA  length = 4
FEATURE                 Location/Qualifiers
REGION                  1..4
                        note = Synthetic Sequence
source                  1..4
                        mol_type = protein
                        organism = synthetic construct
SEQUENCE: 63
GSGS                                                                        4

SEQ ID NO: 64           moltype = AA  length = 4
FEATURE                 Location/Qualifiers
REGION                  1..4
                        note = Synthetic Sequence
```

-continued

```
source                  1..4
                        mol_type = protein
                        organism = synthetic construct
SEQUENCE: 64
GSGG                                                                        4

SEQ ID NO: 65           moltype = AA  length = 4
FEATURE                 Location/Qualifiers
REGION                  1..4
                        note = Synthetic Sequence
source                  1..4
                        mol_type = protein
                        organism = synthetic construct
SEQUENCE: 65
GGGG                                                                        4

SEQ ID NO: 66           moltype = AA  length = 4
FEATURE                 Location/Qualifiers
REGION                  1..4
                        note = Synthetic Sequence
source                  1..4
                        mol_type = protein
                        organism = synthetic construct
SEQUENCE: 66
GRGG                                                                        4

SEQ ID NO: 67           moltype = AA  length = 4
FEATURE                 Location/Qualifiers
REGION                  1..4
                        note = Synthetic Sequence
source                  1..4
                        mol_type = protein
                        organism = synthetic construct
SEQUENCE: 67
GKGG                                                                        4

SEQ ID NO: 68           moltype = AA  length = 195
FEATURE                 Location/Qualifiers
REGION                  1..195
                        note = Synthetic Sequence
source                  1..195
                        mol_type = protein
                        organism = synthetic construct
SEQUENCE: 68
VLEKSDIEKF KNQLRTELTN IDHSYLKGID IASKKKTSNV ENTEFEAIST KIFTDELGFS  60
GKHLGGSNKP DGLLWDDDCA IILDSKAYSE GFPLTASHTD AMGRYLRQFT ERKEEIKPTW  120
WDIAPEHLDN TYFAYVSGSF SGNYKEQLQK FRQDTNHLGG ALEFVKLLLL ANNYKTQKMS  180
KKEVKKSILD YNISY                                                   195

SEQ ID NO: 69           moltype = AA  length = 195
FEATURE                 Location/Qualifiers
REGION                  1..195
                        note = Synthetic Sequence
source                  1..195
                        mol_type = protein
                        organism = synthetic construct
SEQUENCE: 69
VLEKSDIEKF KNQLRTELTN IDHSYLKGID IASKKKTSNV ENTEFEAIST KIFTDELGFS  60
GEHLGGSNKP DGLLWDDDCA IILDSKAYSE GFPLTASHTD AMGRYLRQFT ERKEEIKPTW  120
WDIAPEHLDN TYFAYVSGSF SGNYKEQLQK FRQDTNHLGG ALEFVKLLLL ANNYKTQKMS  180
KKEVKKSILD YNISY                                                   195

SEQ ID NO: 70           moltype = AA  length = 195
FEATURE                 Location/Qualifiers
REGION                  1..195
                        note = Synthetic Sequence
source                  1..195
                        mol_type = protein
                        organism = synthetic construct
SEQUENCE: 70
VLEKSDIEKF KNQLRTELTN IDHSYLKGID IASKPKTSNV ENTEFEAIST KIFTDELGFS  60
GKHLGGSNKP DGLLWDDDCA IILDSKAYSE GFPLTASHTD AMGRYLRQFT ERKEEIKPTW  120
WDIAPEHLDN TYFAYVSGSF SGNYKEQLQK FRQDTNHLGG ALEFVKLLLL ANNYKTQKMS  180
KKEVKKSILD YNISY                                                   195

SEQ ID NO: 71           moltype = AA  length = 195
FEATURE                 Location/Qualifiers
REGION                  1..195
                        note = Synthetic Sequence
```

```
source                  1..195
                        mol_type = protein
                        organism = synthetic construct
SEQUENCE: 71
VLEKSDIEKF KNQLRTELTN IDHSYLKGID IASKPKTSNV ENTEFEAIST KIFTDELGFS  60
GEHLGGSNKP DGLLWDDDCA IILDSKAYSE GFPLTASHTD AMGRYLRQFT ERKEEIKPTW  120
WDIAPEHLDN TYFAYVSGSF SGNYKEQLQK FRQDTNHLGG ALEFVKLLLL ANNYKTQKMS  180
KKEVKKSILD YNISY                                                  195

SEQ ID NO: 72           moltype = AA  length = 191
FEATURE                 Location/Qualifiers
REGION                  1..191
                        note = Synthetic Sequence
source                  1..191
                        mol_type = protein
                        organism = synthetic construct
SEQUENCE: 72
VLEKSDIEKF KNQLRTELTN IDHSYLKGID IASKPVENTE FEAISTKIFT DELGFSGEHL  60
GGSNKPDGLL WDDDCAIILD SKAYSEGFPL TASHTDAMGR YLRQFTERKE EIKPTWWDIA  120
PEHLDNTYFA YVSGSFSGNY KEQLQKFRQD TNHLGGALEF VKLLLLANNY KTQKMSKKEV  180
KKSILDYNIS Y                                                      191

SEQ ID NO: 73           moltype = AA  length = 195
FEATURE                 Location/Qualifiers
REGION                  1..195
                        note = Synthetic Sequence
source                  1..195
                        mol_type = protein
                        organism = synthetic construct
SEQUENCE: 73
VLEKSDIEKF KNQLRTELTN IDHSYLKGID IASKKKTSNV ENTEFEAIST KIFTDELGFS  60
GKHLGGSNKP DGLLWDDDCA IILDSKAYSE GFPLTASHTD AMGRYLRQFT ERKEEIKPTW  120
WDIAPEHLDN TYFAYVSGSF SGDYKEQLQK FRQDTNHLGG ALEFVKLLLL ANNYKTQKMS  180
KKEVKKSILD YNISY                                                  195

SEQ ID NO: 74           moltype = AA  length = 195
FEATURE                 Location/Qualifiers
REGION                  1..195
                        note = Synthetic Sequence
source                  1..195
                        mol_type = protein
                        organism = synthetic construct
SEQUENCE: 74
VLEKSDIEKF KNQLRTELTN IDHSYLKGID IASKKKTSNV ENTEFEAIST KIFTDELGFS  60
GKHLGGSNKP DGLLWDDDCA IILDSKAYSE GFPLTASHTD AMGRYLRQFT ERKEEIKPTW  120
WDIAPEHLDN TYFAYVSGSF SGDYKEQLQK FRQNTNHLGG ALEFVKLLLL ANNYKTQKMS  180
KKEVKKSILD YNISY                                                  195

SEQ ID NO: 75           moltype = AA  length = 196
FEATURE                 Location/Qualifiers
REGION                  1..196
                        note = Synthetic Sequence
source                  1..196
                        mol_type = protein
                        organism = synthetic construct
SEQUENCE: 75
QLVKSELEEK KSELRHKLKY VPHEYIELIE IARNSTQDRI LEMKVMEFFM KVYGYRGKHL  60
GGSRKPDGAI YTVGSPIDYG VIVDTKAYSG GYNLPIGQAD EMQRYVEENQ TRNKHINPNE  120
WWKVYPSSVT EFKFLFVSGH FKGNYKAQLT RLNHITNCNG AVLSVEELLI GGEMIKAGTL  180
TLEEVRRKFN NGEINF                                                 196

SEQ ID NO: 76           moltype = AA  length = 7
FEATURE                 Location/Qualifiers
REGION                  1..7
                        note = Synthetic Sequence
source                  1..7
                        mol_type = protein
                        organism = synthetic construct
SEQUENCE: 76
PKKKRKV                                                           7

SEQ ID NO: 77           moltype = AA  length = 16
FEATURE                 Location/Qualifiers
REGION                  1..16
                        note = Synthetic Sequence
source                  1..16
                        mol_type = protein
                        organism = synthetic construct
SEQUENCE: 77
```

-continued

```
LGRVIPRKIA SRASLM                                                 16

SEQ ID NO: 78           moltype = AA  length = 11
FEATURE                 Location/Qualifiers
REGION                  1..11
                        note = Synthetic Sequence
SITE                    4
                        note = MISC_FEATURE - Xaa can be any naturally occurring
                         amino acid.
source                  1..11
                        mol_type = protein
                        organism = synthetic construct
SEQUENCE: 78
LTPXQVVAIA S                                                      11

SEQ ID NO: 79           moltype = DNA  length = 27
FEATURE                 Location/Qualifiers
misc_feature            1..27
                        note = Synthetic Sequence
source                  1..27
                        mol_type = other DNA
                        organism = synthetic construct
SEQUENCE: 79
cttttccttc tccttctggg gcctgtg                                     27

SEQ ID NO: 80           moltype = DNA  length = 35
FEATURE                 Location/Qualifiers
misc_feature            1..35
                        note = Synthetic Sequence
source                  1..35
                        mol_type = other DNA
                        organism = synthetic construct
SEQUENCE: 80
ctggctactg gccttatctc acaggtaaaa ctgac                            35

SEQ ID NO: 81           moltype = DNA  length = 27
FEATURE                 Location/Qualifiers
misc_feature            1..27
                        note = Synthetic Sequence
source                  1..27
                        mol_type = other DNA
                        organism = synthetic construct
SEQUENCE: 81
cttttccttc tccttctggg gcctgtg                                     27

SEQ ID NO: 82           moltype = DNA  length = 35
FEATURE                 Location/Qualifiers
misc_feature            1..35
                        note = Synthetic Sequence
source                  1..35
                        mol_type = other DNA
                        organism = synthetic construct
SEQUENCE: 82
ctggctactg gccttatctc acaggtaaaa ctgac                            35

SEQ ID NO: 83           moltype = DNA  length = 21
FEATURE                 Location/Qualifiers
misc_feature            1..21
                        note = Synthetic Sequence
source                  1..21
                        mol_type = other DNA
                        organism = synthetic construct
SEQUENCE: 83
gctttgatac ttagccacac c                                           21

SEQ ID NO: 84           moltype = DNA  length = 27
FEATURE                 Location/Qualifiers
misc_feature            1..27
                        note = Synthetic Sequence
source                  1..27
                        mol_type = other DNA
                        organism = synthetic construct
SEQUENCE: 84
cttttccttc tccttctggg gcctgtg                                     27

SEQ ID NO: 85           moltype = DNA  length = 21
FEATURE                 Location/Qualifiers
misc_feature            1..21
                        note = Synthetic Sequence
```

-continued

```
source                 1..21
                       mol_type = other DNA
                       organism = synthetic construct
SEQUENCE: 85
tacacggcgg acttcaatgg t                                       21

SEQ ID NO: 86          moltype = DNA  length = 35
FEATURE                Location/Qualifiers
misc_feature           1..35
                       note = Synthetic Sequence
source                 1..35
                       mol_type = other DNA
                       organism = synthetic construct
SEQUENCE: 86
ctggctactg gccttatctc acaggtaaaa ctgac                        35

SEQ ID NO: 87          moltype = AA  length = 4
FEATURE                Location/Qualifiers
REGION                 1..4
                       note = Synthetic Sequence
source                 1..4
                       mol_type = protein
                       organism = synthetic construct
SEQUENCE: 87
KQWS                                                          4

SEQ ID NO: 88          moltype = AA  length = 215
FEATURE                Location/Qualifiers
REGION                 1..215
                       note = Synthetic Sequence
source                 1..215
                       mol_type = protein
                       organism = synthetic construct
SEQUENCE: 88
YQLKDHILQF VIPNRGVTKQ LVKSELKEKK SELRHKLKYV PHEYIELIEI ARNSTQDRIL  60
EMKVMEFFMK VYGYRGKHLG GSRKPDGAIY TVGSPIDYGV IVDTKAYSGG YNLPIGQADE  120
MQRYVEENQT RNKHINPNEW WKVYPSSVTE FKFLFVSGHF KGNYKAQLTR LNHITNCNGA  180
VLSVEELLIG GEMIKAGTLT LEEVRRKFNN GEINF                         215

SEQ ID NO: 89          moltype = AA  length = 213
FEATURE                Location/Qualifiers
REGION                 1..213
                       note = Synthetic Sequence
source                 1..213
                       mol_type = protein
                       organism = synthetic construct
SEQUENCE: 89
LTLNDKLFDF EIPVQKDVVL EKSDIEKFKN QLRTELTNID HSYLKGIDIA SKKKTSNVEN  60
TEFKAISTKI FTDELGFSGK HLGGSNKPDG LLWDDDCAII LDSKAYSEGF PLTASHTDAM  120
GRYLRQFTER KEEIKPTWWD IAPEHLDNTY FAYVSGSPSG NYKEQLQKFR QDTNHLGGAL  180
EFVKLLLLAN NYKTQKMSKK EVKKSILDYN ISY                           213
```

ENGINEERED GENE-EDITING PROTEINS

PRIORITY

The present application claims priority to U.S. Provisional Application No. 63/023,678, filed on May 12, 2020 and U.S. Provisional Application No. 63/180,390, filed on Apr. 27, 2021, the contents of which are herein incorporated by reference in their entireties.

FIELD

The present invention relates to compositions and methods involving gene-editing proteins.

DESCRIPTION OF THE TEXT FILE SUBMITTED ELECTRONICALLY

The instant application contains a Sequence Listing which has been submitted in ASCII format via EFS-Web and is hereby incorporated by reference in its entirety. Said ASCII copy, created on May 10, 2021, is named FAB-013PC_ST25.txt and is 49,152 bytes in size.

BACKGROUND

Fusion proteins of one or more of naturally occurring proteins containing DNA-binding domains that can recognize specific DNA sequences, such as, zinc fingers (ZFs) and transcription activator-like effectors (TALEs) with cleavage domains of FokI endonuclease have been used in gene editing.

However, current methods for gene editing cells are inefficient and carry a risk of uncontrolled mutagenesis. Further the literature has reported instances of limitations to this technology, such as a lack of acceptable targets, inefficient delivery, inefficient expression of the gene-editing protein/proteins, inefficient gene editing by the expressed gene-editing protein/proteins, due in part to poor binding of DNA-binding domains, excessive off-target effects, due in part to non-directed dimerization of the FokI cleavage domain and poor specificity of DNA-binding domains, and other factors.

Improved gene-editing constructs and method of using the same are desired.

SUMMARY

Accordingly, the present disclosure relates to, in aspects, improved gene-editing proteins and methods of use. For instance, in aspects, there is provided engineered DNA-binding domains and engineered nuclease domains (comprising catalytic domains), or both. Further, in aspects, there is provided methods of selective activation of gene-editing proteins, e.g. via conditional gene-editing, e.g. by modulating temperature of a cell being gene-edited and/or methylation status of the target nucleic acid sequence.

In one aspect, the invention relates to a method for gene-editing a cell, comprising (a) providing a nucleic acid encoding a gene-editing protein, the gene-editing protein comprising: (i) a DNA-binding domain comprising a plurality of repeat sequences and at least one of the repeat sequences comprising a repeat variable di-residue (RVD) at residue 12 or 13 which targets the DNA-binding domain to a target DNA molecule; and (ii) the nuclease domain comprising a catalytic domain of a nuclease, wherein the nucleic acid molecule is a synthetic RNA molecule; and (b) contacting the cell with the one or more synthetic RNA molecules to yield a nick or double-strand break in a target DNA molecule in the cell, wherein the contacting occurs at about 30° C. to about 35° C., e.g., without limitation about 33° C.

In another aspect, the invention relates to a method for making a targeted composition for gene-editing, comprising: (a) selecting a DNA target sequence, the DNA target sequence being substantially unmethylated; and (b) constructing a nucleic acid encoding a gene-editing protein, the gene-editing protein being designed to specifically target the substantially unmethylated DNA target sequence and comprising: (i) a DNA-binding domain comprising a plurality of repeat sequences and at least one of the repeat sequences comprises the amino acid sequence: LTPvQVVAIAwxyzα (SEQ ID NO: 11) and is between 36 and 39 amino acids long, wherein: v is Q, D or E, w is S or N, x is I, H, N, or I, y is D, A, I, N, H, K, S, G or null, z is GGRPALE (SEQ ID NO: 1), GGKQALE (SEQ ID NO: 2), GGKQALETVQRLLPVLCQDHG (SEQ ID NO: 3), GGKQALETVQRLLPVLCQAHG (SEQ ID NO: 4), GKQALETVQRLLPVLCQDHG (SEQ ID NO: 5), GKQALETVQRLLPVLCQAHG (SEQ ID NO: 6), GGKQALETVQRLLPVLCQD (SEQ ID NO: 7) or GGKQALETVQRLLPVLCQA (SEQ ID NO: 8), α is four consecutive amino acids; (ii) the nuclease domain comprising a catalytic domain of a nuclease, wherein the nucleic acid molecule is a synthetic RNA molecule.

In another aspect, the invention relates to a method for gene-editing a cell, comprising (a) providing a nucleic acid encoding a gene-editing protein, the gene-editing protein comprising: (i) a DNA-binding domain comprising a plurality of repeat sequences and at least one of the repeat sequences comprises the amino acid sequence: LTPvQVVAIAwxyzα (SEQ ID NO: 11) and is between 36 and 39 amino acids long, wherein: v is Q, D or E, w is S or N, x is I, H, N, or I, y is D, A, I, N, H, K, S, G or null, z is GGRPALE (SEQ ID NO: 1), GGKQALE (SEQ ID NO: 2), GGKQALETVQRLLPVLCQDHG (SEQ ID NO: 3), GGKQALETVQRLLPVLCQAHG (SEQ ID NO: 4), GKQALETVQRLLPVLCQDHG (SEQ ID NO: 5), GKQALETVQRLLPVLCQAHG (SEQ ID NO: 6), GGKQALETVQRLLPVLCQD (SEQ ID NO: 7) or GGKQALETVQRLLPVLCQA (SEQ ID NO: 8), α is four consecutive amino acids; (ii) the nuclease domain comprising a catalytic domain of a nuclease, wherein the nucleic acid molecule is a synthetic RNA molecule; and (b) contacting the cell with the one or more synthetic RNA molecules yield a nick or double-strand break in a target DNA molecule in the cell; and (c) contacting the cell with a demethylating agent.

In another aspect, the invention relates to a composition comprising a nucleic acid encoding a gene-editing protein, the gene-editing protein comprising: (a) the DNA-binding domain comprising a plurality of repeat sequences and at least one of the repeat sequences comprises a repeat variable di-residue (RVD) at residue 12 or 13; and (b) the nuclease domain comprising a catalytic domain, the catalytic domain comprising a hybrid of the catalytic domains of FokI and StsI, comprising the α1, α2, α3, α4, α5, α6, β1, β2, β2, β2, β2, and β6 domains of FokI with at least one of the domains of FokI being substituted in whole or in part with the α1, α2, α3, α4, α5, α6, β1, β2, β2, β2, β2, and β6 domains of StsI and optionally comprising at least one mutation.

In another aspect, the invention relates to a composition comprising a nucleic acid encoding a gene-editing protein, the gene-editing protein comprising: (a) the DNA-binding domain comprising a plurality of repeat sequences and at least one of the repeat sequences comprises the amino acid sequence: LTPvQVVAIAwxyzα (SEQ ID NO: 11) and is between 36 and 39 amino acids long, wherein: v is Q, D or E, w is S or N, x is I, H, N, or I, y is D, A, I, N, H, K, S, G or null, z is GGRPALE (SEQ ID NO: 1), GGKQALE (SEQ ID NO: 2), GGKQALETVQRLLPVLCQDHG (SEQ ID NO: 3), GGKQALETVQRLLPVLCQAHG (SEQ ID NO: 4), GKQALETVQRLLPVLCQDHG (SEQ ID NO: 5), GKQALETVQRLLPVLCQAHG (SEQ ID NO: 6), GGKQALETVQRLLPVLCQD (SEQ ID NO: 7) or GGKQALETVQRLLPVLCQA (SEQ ID NO: 8), α is four consecutive amino acids, with the proviso that α is not GHGG (SEQ ID NO: 38), HGSG (SEQ ID NO: 39), and HGGG (SEQ ID NO: 40); and (b) the nuclease domain comprising a catalytic domain of a nuclease.

In another aspect, the invention relates to a composition comprising a nucleic acid encoding a gene-editing protein, the gene-editing protein comprising: (a) the DNA-binding domain comprises a plurality of repeat sequences and at least one of the repeat sequences comprises the amino acid sequence of between 36 and 39 amino acids long, of which the four most C-terminal amino acids are selected from GGHD (SEQ ID NO: 41), GAHD (SEQ ID NO: 42), AHDG (SEQ ID NO: 43), PHDG (SEQ ID NO: 44), GPHD (SEQ ID NO: 45), GHGP (SEQ ID NO: 46), PHGG (SEQ ID NO: 47), PHGP (SEQ ID NO: 48), AHGA (SEQ ID NO: 49), LHGA (SEQ ID NO: 50), VHGA (SEQ ID NO: 51), IVHG (SEQ ID NO: 52), IHGM (SEQ ID NO: 53), RHGD (SEQ ID NO: 54), RDHG (SEQ ID NO: 55), RHGE (SEQ ID NO: 56), HRGE (SEQ ID NO: 57), HRGD (SEQ ID NO: 58), GPYE (SEQ ID NO: 59), NHGG (SEQ ID NO: 60), THGG (SEQ ID NO: 61), GTHG (SEQ ID NO: 62), GSGS (SEQ ID NO: 63), GSGG (SEQ ID NO: 64), GGGG (SEQ ID NO: 65), GRGG (SEQ ID NO: 66), and GKGG (SEQ ID NO: 67); and (b) the nuclease domain comprises a catalytic domain of a nuclease.

In embodiments, the composition further comprises one or more of the linear DNA templates described herein.

In another aspect, the invention relates to a method of treating a disease or disorder comprising (a) contacting a cell or tissue with one or more cooling elements to locally reduce temperature; and (b) administering a nucleic acid encoding a gene-editing protein, the gene-editing protein comprising: (i) a DNA-binding domain comprising a plurality of repeat sequences and at least one of the repeat sequences comprises a repeat variable di-residue (RVD) at residue 12 or 13 which targets the DNA-binding domain to a target DNA molecule; and (ii) a nuclease domain comprising a catalytic domain of a nuclease, wherein the nucleic acid molecule is a synthetic RNA molecule. In embodiments, the method further comprises administering one or more of the linear DNA templates described herein.

In another aspect, the invention relates to a method of treating a disease or disorder comprising (a) providing a nucleic acid encoding a gene-editing protein, the gene-editing protein comprising: (i) a DNA-binding domain comprising a plurality of repeat sequences and at least one of the repeat sequences comprises a repeat variable di-residue (RVD) at residue 12 or 13 which targets the DNA-binding domain to a target DNA molecule; and (ii) a nuclease domain comprising a catalytic domain of a nuclease, wherein the nucleic acid molecule is a synthetic RNA molecule; (b) transfecting the cell with the one or more synthetic RNA molecules to yield a nick or double-strand break in a target DNA molecule in the cell, wherein the transfecting occurs at about 30° C. to about 35° C., e.g., without limitation about 33° C.; and (c) administering the transfected cell to a subject in need thereof.

In aspects, the present invention relates to a cell comprising any of the disclosed compositions.

BRIEF DESCRIPTION OF THE DRAWINGS

FIG. 1 is a flow Chart showing the creation and testing process for the NoveSlice gene-editing protein.

FIG. 3C depicts the spacing between the two DNA binding sites of a variety of NoveSlice gene-editing protein dimers, with the target splice acceptor being COL7A1E73. NS denotes a NoveSlice gene-editing protein.

FIG. 7A depicts the amino acid sequences of modified linkers created in the second last synthetic DNA Binding Domain (sDBD) positions of NoveSlice gene-editing proteins (NS).

DETAILED DESCRIPTION

Figure 2:
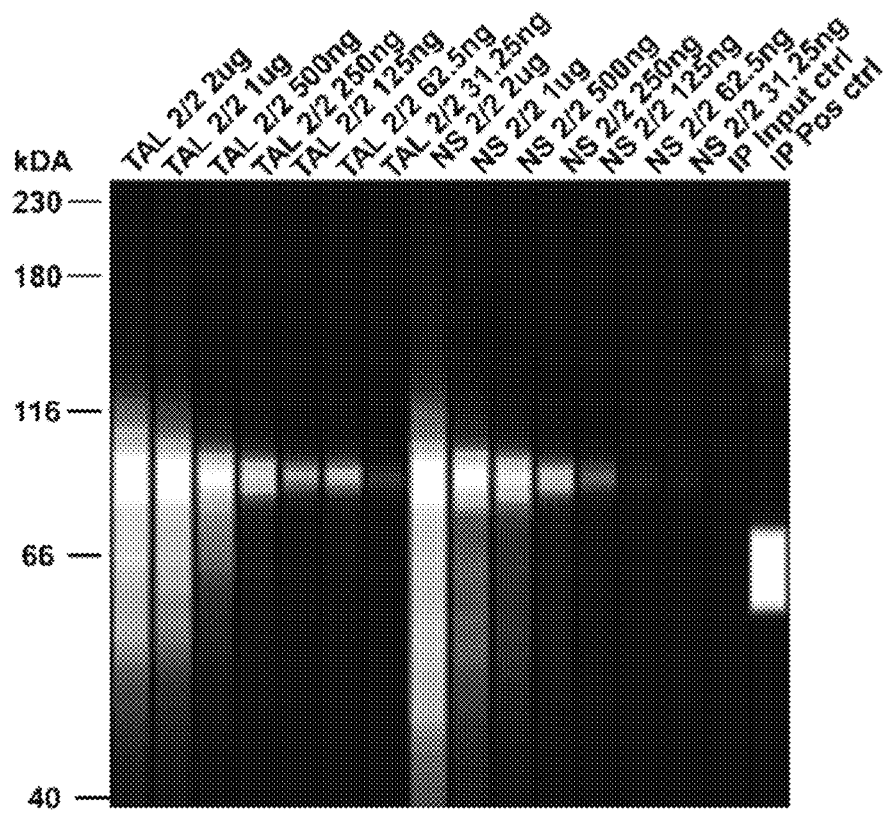
FIG. 2 depicts that both TALEN and NoveSlice gene-editing proteins can be expressed and detected using the same FLAG-tag. NS denotes a NoveSlice gene-editing protein.

In aspects, the present invention relates to novel gene-editing proteins having uniquely engineered DNA-binding domains, engineered nuclease domains (comprising catalytic domains), or both. In aspects, the present invention relates to methods for providing conditional gene-editing, e.g. by modulating temperature of a cell being gene-edited and/or methylation status of the target nucleic acid sequence.

The DNA sequence of a cell can be altered by contacting the cell with a gene-editing protein or by inducing the cell to express a gene-editing protein. However, previously disclosed gene-editing proteins suffer from low binding efficiency and excessive off-target activity, which can introduce undesired mutations in the DNA of the cell, severely limiting their use in therapeutic applications, in which the introduction of undesired mutations in a patient's cells could lead to the development of cancer.

In some embodiments, that present gene-editing proteins exhibit substantially lower off-target activity than previously disclosed gene-editing proteins, while maintaining a high level of on-target activity. In some embodiments, other novel engineered proteins exhibit high on-target activity, low off-target activity, small size, solubility, and other desirable characteristics.

Conditional Activity: Temperature Dependence

In one aspect, the invention relates to a method for gene-editing a cell, comprising (a) providing a nucleic acid encoding a gene-editing protein, the gene-editing protein comprising: (i) a DNA-binding domain comprising a plurality of repeat sequences and at least one of the repeat sequences comprising a repeat variable di-residue (RVD) at residue 12 or 13 which targets the DNA-binding domain to a target DNA molecule; and (ii) a nuclease domain comprising a catalytic domain of a nuclease, wherein the nucleic acid molecule is a synthetic RNA molecule; and (b) contacting the cell with the one or more synthetic RNA molecules to yield a nick or double-strand break in a target DNA molecule in the cell, wherein the contacting occurs at about 30° C. to about 35° C., e.g., without limitation about 33° C.

In some embodiments, the RVD recognizes one base pair in the nucleic acid molecule. In some embodiments, the RVD recognizes a C residue in the nucleic acid molecule and is selected from HD, N(null), HA, ND, and HI. In some embodiments, the RVD recognizes a G residue in the nucleic acid molecule and is selected from NN, NH, NK, HN, and NA. In some embodiments, the RVD recognizes an A residue in the nucleic acid molecule and is selected from NI and NS. In some embodiments, the RVD recognizes a T residue in the nucleic acid molecule and is selected from NG, HG, H(null), and IG.

In some embodiments, the RVD recognizing a C residue in the nucleic acid molecule is HD. In some embodiments, the RVD recognizing a C residue in the nucleic acid molecule is N(null). In some embodiments, the RVD recognizing a C residue in the nucleic acid molecule is HA. In some embodiments, the RVD recognizing a C residue in the nucleic acid molecule is ND. In some embodiments, the RVD recognizing a C residue in the nucleic acid molecule is HI. In some embodiments, the RVD recognizing a G residue in the nucleic acid molecule is NN. In some embodiments, the RVD recognizing a G residue in the nucleic acid molecule is NH. In some embodiments, the RVD recognizing a G residue in the nucleic acid molecule is NK. In some embodiments, the RVD recognizing a G residue in the nucleic acid molecule is HN. In some embodiments, the RVD recognizing a G residue in the nucleic acid molecule is NA. In some embodiments, the RVD recognizing an A residue in the nucleic acid molecule is NI. In some embodiments, the RVD recognizing an A residue in the nucleic acid molecule is NS. In some embodiments, the RVD recognizing a T residue in the nucleic acid molecule is NG. In some embodiments, the RVD recognizing a T residue in the nucleic acid molecule is HG. In some embodiments, the RVD recognizing a T residue in the nucleic acid molecule is H(null). In some embodiments, the RVD recognizing a T residue in the nucleic acid molecule is IG.

In embodiments, the contacting comprises the cell uptaking the one or more synthetic RNA molecules. In embodiments, the contacting comprises transfection. In some embodiments, the transfection comprises contacting a cell with a molecule, wherein the molecule is internalized by the cell. In some embodiments, the transfection comprises the use of a transfection reagent. In some embodiments, the transfection reagent is a substance or mixture of substances that associates with a molecule and facilitates the delivery of the molecule to and/or internalization of the molecule by a cell. In some embodiments, the transfection reagent is a cationic lipid, a charged polymer or a cell-penetrating peptide.

In some embodiments, the transfection comprises the use of a complexation medium. In some embodiments, the complexation medium is a medium to which a transfection reagent and a molecule to be transfected are added and in which the transfection reagent associates with the molecule to be transfected. In some embodiments, the transfection comprises a transfection medium. In some embodiments, the transfection medium is Dulbecco's Modified Eagle's Medium (DMEM) or DMEM/F12.

In embodiments, the contacting occurs at about 30° C. In some embodiments, the contacting occurs at about 31° C. In some embodiments, the contacting occurs at about 32° C. In some embodiments, the contacting occurs at about 33° C. In some embodiments, the contacting occurs at about 34° C. In some embodiments, the contacting occurs at about 35° C. In embodiments, the gene-editing protein is functionally temperature-switchable. In embodiments, the method further comprises the step of (c) culturing the contacted cell at about 30° C. to about 35° C. In embodiments, the method further comprises the step of (c) culturing the contacted cell at about 30° C. In embodiments, the method further comprises the step of (c) culturing the contacted cell at about 31° C. In embodiments, the method further comprises the step of (c) culturing the contacted cell at about 32° C. In embodiments, the method further comprises the step of (c) culturing the contacted cell at about 33° C. In embodiments, the method further comprises the step of (c) culturing the contacted cell at about 34° C. In embodiments, the method further comprises the step of (c) culturing the contacted cell at about 35° C.

In embodiments, the method allows for conditional gene-editing. In embodiments, the method allows for localized gene-editing.

In embodiments, the method is conducted in vitro. In embodiments, the method is conducted ex vivo.

In embodiments, the method further comprises the step of (c) administering the contacted cell to a subject in need thereof. In embodiments, the cell is formulated for therapeutic use. In embodiments, the cell is suitable for administration to a human subject. In embodiments, the method is conducted in vivo.

In embodiments, the method comprises reducing the body temperature of a subject, optionally via whole-body hypothermia. In embodiments, the body temperature of the subject is reduced by between about 0.5° C. to about 1° C. In embodiments, the body temperature of the subject is reduced by between about 1° C. to about 1.5° C. In embodiments, the body temperature of the subject is reduced by between about 1.5° C. to about 2° C. In embodiments, the body temperature of the subject is reduced by between about 2° C. to about 2.5° C. In embodiments, the body temperature of the subject is reduced by between about 2.5° C. to about 3° C. In embodiments, the body temperature of the subject is reduced by between about 3° C. to about 3.5° C. In embodiments, the body temperature of the subject is reduced by between about 3.5° C. to about 4° C. In embodiments, the body temperature of the subject is reduced by between about 4° C. to about 4.5° C. In embodiments, the body temperature of the subject is reduced by between about 4.5° C. to about 5° C. In embodiments, the body temperature of the subject is reduced by between about 5° C. to about 5.5° C. In embodiments, the body temperature of the subject is reduced by between about 5.5° C. to about 6° C. In embodiments, the body temperature of the subject is reduced by between about 6° C. to about 6.5° C. In embodiments, the body temperature of the subject is reduced by between about 6.5° C. to about 7° C. In embodiments, the body temperature of the subject is reduced by between about 7° C. to about 7.5° C. In embodiments, the body temperature of the subject is reduced by between about 7.5° C. to about 8° C. In embodiments, the body temperature of the subject is reduced by between about 8° C. to about 8.5° C. In embodiments, the body temperature of the subject is reduced by between about 8.5° C. to about 9° C. In embodiments, the body temperature of the subject is reduced by between about 9° C. to about 9.5° C. In embodiments, the body temperature of the subject is reduced by between about 9.5° C. to about 10° C. In embodiments, the body temperature of the subject is reduced by between about 10° C. to about 10.5° C. In embodiments, the body temperature of the subject is reduced by between about 10.5° C. to about 11° C. In embodiments, the body temperature of the subject is reduced by between about 11° C. to about 11.5° C.

In some embodiments, the reducing the body temperature of the subject is performed for a specific amount of time. In some embodiments, the specific amount of time is between about 15 minutes to about 30 minutes. In some embodiments, the specific amount of time is between about 30 minutes to about 45 minutes. In some embodiments, the specific amount of time is between about 45 minutes to about 60 minutes. In some embodiments, the specific amount of time is between about 1 hour to about 1.5 hours. In some embodiments, the specific amount of time is between about 1.5 hours to about 2 hours. In some embodiments, the specific amount of time is between about 2 hours to about 2.5 hours. In some embodiments, the specific amount of time is between about 2.5 hours to about 3 hours. In some embodiments, the specific amount of time is between about 3 hours to about 3.5 hours. In some embodiments, the specific amount of time is between about 3.5 hours to about 4 hours. In some embodiments, the specific amount of time is between about 4 hours to about 4.5 hours. In some embodiments, the specific amount of time is between about 4.5 hours to about 5 hours. In some embodiments, the specific amount of time is between about 5 hours to about 5.5 hours. In some embodiments, the specific amount of time is between about 5.5 hours to about 6 hours. In some embodiments, the specific amount of time is between about 6 hours to about 6.5 hours.

In embodiments, the method comprises applying one or more cooling elements to a cell or tissue in vivo to reduce temperature, the cooling element optionally being a cryo-compression device. In embodiments, the temperature is reduced by between about 0.5° C. to about 1° C. In embodiments, the temperature is reduced by between about 1° C. to about 1.5° C. In embodiments, the temperature is reduced by between about 1.5° C. to about 2° C. In embodiments, the temperature is reduced by between about 2° C. to about 2.5° C. In embodiments, the temperature is reduced by between about 2.5° C. to about 3° C. In embodiments, the temperature is reduced by between about 3° C. to about 3.5° C. In embodiments, the temperature is reduced by between about 3.5° C. to about 4° C. In embodiments, the temperature is reduced by between about 4° C. to about 4.5° C. In embodiments, the temperature is reduced by between about 4.5° C. to about 5° C. In embodiments, the temperature is reduced by between about 5° C. to about 5.5° C. In embodiments, the temperature is reduced by between about 5.5° C. to about 6° C. In embodiments, the temperature is reduced by between about 6° C. to about 6.5° C. In embodiments, the temperature is reduced by between about 6.5° C. to about 7° C. In embodiments, the temperature is reduced by between about 7° C. to about 7.5° C. In embodiments, the temperature is reduced by between about 7.5° C. to about 8° C. In embodiments, the temperature is reduced by between about 8° C. to about 8.5° C. In embodiments, the temperature is reduced by between about 8.5° C. to about 9° C. In embodiments, the temperature is reduced by between about 9° C. to about 9.5° C. In embodiments, the temperature is reduced by between about 9.5° C. to about 10° C. In embodiments, the temperature is reduced by between about 10° C. to about 10.5° C. In embodiments, the temperature is reduced by between about 10.5° C. to about 11° C. In embodiments, the temperature is reduced by between about 11° C. to about 11.5° C.

In some embodiments, the applying one or more cooling elements to a cell or tissue in vivo to reduce temperature is performed for a specific amount of time. In some embodiments, the specific amount of time is between about 15 minutes to about 30 minutes. In some embodiments, the specific amount of time is between about 30 minutes to about 45 minutes. In some embodiments, the specific amount of time is between about 45 minutes to about 60 minutes. In some embodiments, the specific amount of time is between about 1 hour to about 1.5 hours. In some embodiments, the specific amount of time is between about 1.5 hours to about 2 hours. In some embodiments, the specific amount of time is between about 2 hours to about 2.5 hours. In some embodiments, the specific amount of time is between about 2.5 hours to about 3 hours. In some embodiments, the specific amount of time is between about 3 hours to about 3.5 hours. In some embodiments, the specific amount of time is between about 3.5 hours to about 4 hours. In some embodiments, the specific amount of time is between about 4 hours to about 4.5 hours. In some embodiments, the specific amount of time is between about 4.5 hours to about 5 hours. In some embodiments, the specific amount of time is between about 5 hours to about 5.5 hours. In some embodiments, the specific amount of time is between about 5.5 hours to about 6 hours. In some embodiments, the specific amount of time is between about 6 hours to about 6.5 hours.

In embodiments, the cell or tissue is of the integumentary system. In embodiments, the cell or tissue is a skin cell. In embodiments, the cell is of the integumentary system. In embodiments, the cell is a skin cell. In embodiments, the skin cell is a fibroblast, a keratinocyte, a melanocyte, or an adipocyte. In some embodiments, the synthetic RNA molecule is a nucleic acid drug. In some embodiments, the nucleic acid drug may alter, modify and/or change the appearance of a member of the integumentary system of a subject such as, but not limited, to skin, hair and nails. Such alteration, modification and/or change may be in the context of treatment methods and/or therapeutic uses as described herein including, by way of non-limiting example, dermatological treatments and cosmetics procedures.

In various embodiments, the agents of the present invention are used in methods the effect the integumentary system of a human. The present compositions and methods may be used to alter a biological and/or physiological process to, for example, reduce skin sagging, increase skin thickness, increase skin volume, reduce the number of wrinkles, the length of wrinkles and/or the depth of wrinkles, increase skin tightness, firmness, tone and/or elasticity, increase skin hydration and ability to retain moisture, water flow and osmotic balance, increase the levels of skin lipids; increase the extracellular matrix and/or adhesion and communication polypeptides; increase skin energy production; utilization and conservation; improve oxygen utilization; improve skin cell life; improve skin cell immunity defense, heat shock stress response, antioxidant defense capacity to neutralize free radicals, and/or toxic defense; improve the protection and recovery from ultraviolet rays; improve skin cell communication and skin cell innervations; improve cell cohesion/adhesion; improve calcium mineral and other mineral metabolism; improve cell turnover; and improve cell circadian rhythms.

Further still, in some embodiments, the present compositions may be used in the treatment, control, or prevention of a disease, disorder and/or condition and/or may alter, modify or change the appearance of a member of the integumentary system of a subject suffering from a disease, disorder and/or condition such as, but not limited to, acne vulgaris, acne aestivalis, acne conglobata, acne cosmetic, acne fulminans, acne keloidalis nuchae, acne mechanica, acne medicamentosa, acne miliaris necrotica, acne necrotica, acne rosacea, actinic keratosis, acne vulgaris, acne aestivalis, acne conglobata, acne cosmetic, acne fulminans, acne keloidalis nuchae, acne mechanica, acne medicamentosa, acne miliaris necrotica, acne necrotica, acne rosacea, acute urticaria, allergic contact dermatitis, alopecia areata, angioedema, athlete's foot, atopic dermatitis, autoeczematization, baby acne, balding, bastomycosis, blackheads, birthmarks and other skin pigmentation problems, boils, bruises, bug bites and stings, burns, cellulitis, chiggers, chloracne, cholinergic or stress uricara, chronic urticara, cold type urticara, confluent and reticulated papillomatosis, corns, cysts, dandruff, dermatitis herpetiformis, dermatographism, dyshidrotic eczema, diaper rash, dry skin, dyshidrosis, ectodermal dysplasia such as, hyprohidrotic ectodermal dysplasia and X-linked hyprohidrotic ectodermal dysplasia, eczema, epidermaodysplasia verruciformis, erythema nodosum, excoriated acne, exercise-induced anaphylasis folliculitis, excess skin oil, folliculitis, freckles, frostbite, fungal nails, hair density, hair growth rate, halogen acne, hair loss, heat rash, hematoma, herpes simplex infections (e.g. non-genital), hidradenitis suppurativa, hives, hyperhidrosis, hyperpigmentation, hypohidrotic ectodermal dysplasia, hypopigmentation, impetigo, ingrown hair, heat type urticara, ingrown toenail, infantile acne or neonatal acne, itch, irritant contact dermatitis, jock itch, keloid, keratosis pilaris, lichen planus, lichen sclerosus, lupus miliaris disseminatus faciei, melasma, moles, molluscum contagiosum, nail growth rate, nail health, neurodermatitis, nummular eczema, occupational acne, oil acne, onychomycosis, physical urticara, pilonidal cyst, *Pityriasis rosea*, *Pityriasis versicolor*, poison ivy, pomade acne, pseudofolliculitis barbae or acne keloidalis nuchae, psoriasis, psoriatic arthritis, pressure or delayed pressuez urticara, puncture wounds such as cuts and scrapes, rash, rare or water type urticara, rhinoplasty, ringworm, rosacea, rothmund-thomson syndrome, sagging of the skin, scabis, scars, seborrhea, seborrheic dermatitis, shingles, skin cancer, skin tag, solar type urticara, spider bite, stretch marks, sunburn, tar acne, tropical acne, thinning of skin, thrush, tinea versicolor, transient acantholytic dermatosis, tycoon's cap or acne necrotica miliaris, uneven skin tone, varicose veins, venous eczema, vibratory angioedema, vitiligo, warts, Weber-Christian disease, wrinkles, x-linked hypohidrotic ectodermal dysplasia, xerotic eczema, yeast infection and general signs of aging.

Other embodiments are directed to a method for delivering a nucleic acid to a cell in vivo comprising applying a nucleic acid to a tissue containing a cell in vivo. In one embodiment, the method further comprises applying a transient electric field in the vicinity of the cell. In another embodiment, the method results in the cell in vivo internalizing the nucleic acid. In yet another embodiment, the nucleic acid comprises synthetic RNA. In a further embodiment, the method further results in the cell internalizing a therapeutically or cosmetically effective amount of the nucleic acid. In one embodiment, the cell is a skin cell. In another embodiment, the cell is a muscle cell. In yet another embodiment, the cell is a dermal fibroblast. In a further embodiment, the cell is a keratinocyte. In a still further embodiment, the cell is a myoblast. In some embodiments, the nucleic acid comprises a protein of interest. In one embodiment, the protein of interest is a fluorescent protein. In another embodiment, the protein of interest is an extracellular-matrix protein. In yet another embodiment, the protein of interest is a member of the group: elastin, collagen, laminin, fibronectin, vitronectin, lysyl oxidase, elastin binding protein, a growth factor, fibroblast growth factor, transforming growth factor beta, granulocyte colony-stimulating factor, a matrix metalloproteinase, an actin, fibrillin, microfibril-associated glycoprotein, a lysyl-oxidase-like protein, platelet-derived growth factor, a lipase, an uncoupling protein, thermogenin, filaggrin, a fibroblast growth factor, an antibody, and a protein involved with pigment production. In some embodiments, the method further comprises delivering the nucleic acid to the epidermis. In other embodiments, the method further comprises delivering the nucleic acid to the dermis. In still other embodiments, the method further comprises delivering the nucleic acid below the dermis. In one embodiment, the delivering is by injection. In another embodiment, the delivering is by injection using a micro-needle array. In yet another embodiment, the delivering is by topical administration. In a further embodiment, the delivering comprises disruption or removal of a part of the tissue. In a still further embodiment, the delivering comprises disruption or removal of the stratum corneum. In some embodiments, the nucleic acid is present in solution. In one embodiment, the solution comprises a growth factor. In another embodiment, the growth factor is a member of the group: a fibroblast growth factor and a transforming growth factor. In yet another embodiment, the growth factor is a member of the group: basis fibroblast growth factor and transforming growth factor beta. In other embodiments, the solution comprises cholesterol.

In another embodiment, the method further comprises contacting the cell with one or more nucleic acid molecules. In yet another embodiment, at least one of the one or more nucleic acid molecules encodes a protein of interest. In a further embodiment, the method results in the cell expressing the protein of interest. In a still further embodiment, the method results in the cell expressing a therapeutically or cosmetically effective amount of the protein of interest.

In another embodiment, the cell is contacted with a nucleic acid molecule. In yet another embodiment, the method results in the cell internalizing the nucleic acid molecule. In a further embodiment, the method results in the cell internalizing a therapeutically or cosmetically effective amount of the nucleic acid molecule. In one embodiment, the nucleic acid encodes a protein of interest. In one embodiment, the nucleic acid molecule comprises a member of the group: a dsDNA molecule, a ssDNA molecule, a RNA molecule, a dsRNA molecule, a ssRNA molecule, a plasmid, an oligonucleotide, a synthetic RNA molecule, a miRNA molecule, an mRNA molecule, and an siRNA molecule. In various embodiments, the RNA comprises one or more non-canonical nucleotides.

In some embodiments, the present invention relates to one or more administration techniques described in U.S. Pat. Nos. 5,711,964; 5,891,468; 6,316,260; 6,413,544; 6,770,291; and 7,390,780, the entire contents of which are hereby incorporated by reference in their entireties.

In embodiments, the synthetic RNA molecule is mRNA.

In embodiments, the DNA-binding domain comprises about 15, or about, 16, or about 17, or about 18, or about 18.5 repeat sequences.

Conditional Activity: Methylation Status

In one aspect, the invention relates to a method for making a targeted composition for gene-editing, comprising: (a) selecting a DNA target sequence, the DNA target sequence being substantially unmethylated; and (b) constructing a nucleic acid encoding a gene-editing protein, the gene-editing protein being designed to specifically target the substantially unmethylated DNA target sequence and comprising: (i) a DNA-binding domain comprising a plurality of repeat sequences and at least one of the repeat sequences comprises the amino acid sequence: LTPvQVVAIAwxyzα (SEQ ID NO: 11) and is between 36 and 39 amino acids long, wherein: v is Q, D or E, w is S or N, x is I, H, N, or I, y is D, A, I, N, H, K, S, G or null, z is GGRPALE (SEQ ID NO: 1), GGKQALE (SEQ ID NO: 2), GGKQALETVQRLLPVLCQDHG (SEQ ID NO: 3), GGKQALETVQRLLPVLCQAHG (SEQ ID NO: 4), GKQALETVQRLLPVLCQDHG (SEQ ID NO: 5), GKQALETVQRLLPVLCQAHG (SEQ ID NO: 6), GGKQALETVQRLLPVLCQD (SEQ ID NO: 7) or GGKQALETVQRLLPVLCQA (SEQ ID NO: 8), α is four consecutive amino acids; (ii) a nuclease domain comprising a catalytic domain of a nuclease, wherein the nucleic acid molecule is a synthetic RNA molecule.

In another aspect, the invention relates to a method for gene-editing a cell, comprising (a) providing a nucleic acid encoding a gene-editing protein, the gene-editing protein comprising: (i) a DNA-binding domain comprising a plurality of repeat sequences and at least one of the repeat sequences comprises the amino acid sequence: LTPvQVVAIAwxyzα (SEQ ID NO: 11) and is between 36 and 39 amino acids long, wherein: v is Q, D or E, w is S or N, x is I, H, N, or I, y is D, A, I, N, H, K, S, G or null, z is GGRPALE (SEQ ID NO: 1), GGKQALE (SEQ ID NO: 2), GGKQALETVQRLLPVLCQDHG (SEQ ID NO: 3), GGKQALETVQRLLPVLCQAHG (SEQ ID NO: 4), GKQALETVQRLLPVLCQDHG (SEQ ID NO: 5), GKQALETVQRLLPVLCQAHG (SEQ ID NO: 6), GGKQALETVQRLLPVLCQD (SEQ ID NO: 7) or GGKQALETVQRLLPVLCQA (SEQ ID NO: 8), α is four consecutive amino acids; (ii) a nuclease domain comprising a catalytic domain of a nuclease, wherein the nucleic acid molecule is a synthetic RNA molecule; and (b) contacting the cell with the one or more synthetic RNA molecules yield a nick or double-strand break in a target DNA molecule in the cell; and (c) contacting the cell with a demethylating agent.

In some embodiments, z is GGRPALE (SEQ ID NO: 1) and α is null. In some embodiments, z is GGKQALE (SEQ ID NO: 2) and α is null. In some embodiments, z is GGKQALETVQRLLPVLCQDHG (SEQ ID NO: 3) and α is null. In some embodiments, z is GGKQALETVQRLLPVLCQAHG (SEQ ID NO: 4) and α is null. In some embodiments, z is GKQALETVQRLLPVLCQDHG (SEQ ID NO: 5) and α is null. In some embodiments, z is GKQALETVQRLLPVLCQAHG (SEQ ID NO: 6) and α is null. In some embodiments, z is GGKQALETVQRLLPVLCQD (SEQ ID NO: 7) and α is null. In some embodiments, z is GGKQALETVQRLLPVLCQA (SEQ ID NO: 8) and α is null.

In some embodiments, z is GGRPALE (SEQ ID NO: 1). In some embodiments, z is GGKQALE (SEQ ID NO: 2). In some embodiments, z is GGKQALETVQRLLPVLCQDHG (SEQ ID NO: 3). In some embodiments, z is GGKQALETVQRLLPVLCQAHG (SEQ ID NO: 4). In some embodiments, z is GKQALETVQRLLPVLCQDHG (SEQ ID NO: 5). In some embodiments, z is GKQALETVQRLLPVLCQAHG (SEQ ID NO: 6). In some embodiments, z is GGKQALETVQRLLPVLCQD (SEQ ID NO: 7). In some embodiments, z is GGKQALETVQRLLPVLCQA (SEQ ID NO: 8).

In embodiments, the demethylating agent is selected from 5-azacitidine and 5-aza-2'-deoxycitidine (decitabine).

In embodiments, the method allows for conditional gene-editing. In embodiments, the method allows for localized gene-editing. In embodiments, the method further comprises administering one or more of the linear DNA templates described herein.

In embodiments, the method is conducted in vitro. In embodiments, the method is conducted ex vivo.

In embodiments, the method further comprises the step of (c) administering the contacted cell to a subject in need thereof. In embodiments, the cell is formulated for therapeutic use. In embodiments, the cell is suitable for administration to a human subject. In embodiments, the method is conducted in vivo.

In embodiments, the identity of x and y are based on the substantially unmethylated DNA target sequence.

In embodiments, x and y: recognize a C residue in the nucleic acid molecule and are selected from HD, N(null), HA, ND, and HI; recognize a G residue in the nucleic acid molecule and are selected from NN, NH, NK, HN, and NA; recognize an A residue in the nucleic acid molecule and are selected from NI and NS; or recognize a T residue in the nucleic acid molecule and are selected from NG, HG, H(null), and IG.

In some embodiments, the RVD recognizing a C residue in the nucleic acid molecule is HD. In some embodiments, the RVD recognizing a C residue in the nucleic acid molecule is N(null). In some embodiments, the RVD recognizing a C residue in the nucleic acid molecule is HA. In some embodiments, the RVD recognizing a C residue in the nucleic acid molecule is ND. In some embodiments, the RVD recognizing a C residue in the nucleic acid molecule is HI. In some embodiments, the RVD recognizing a G residue in the nucleic acid molecule is NN. In some embodiments, the RVD recognizing a G residue in the nucleic acid molecule is NH. In some embodiments, the RVD recognizing a G residue in the nucleic acid molecule is NK. In some embodiments, the RVD recognizing a G residue in the nucleic acid molecule is HN. In some embodiments, the RVD recognizing a G residue in the nucleic acid molecule is NA. In some embodiments, the RVD recognizing an A residue in the nucleic acid molecule is NI. In some embodiments, the RVD recognizing an A residue in the nucleic acid molecule is NS. In some embodiments, the RVD recognizing a T residue in the nucleic acid molecule is NG. In some embodiments, the RVD recognizing a T residue in the nucleic acid molecule is HG. In some embodiments, the RVD recognizing a T residue in the nucleic acid molecule is H(null). In some embodiments, the RVD recognizing a T residue in the nucleic acid molecule is IG.

In embodiments, a comprises at least one glycine (G) residue. In embodiments, a comprises at least one histidine (H) residue. In embodiments, a comprises at least one histidine (H) residue at any one of positions 33, 34, or 35. In embodiments, a comprises at least one aspartic acid (D) residue. In embodiments, a comprises at least one, or two, or three of a glycine (G) residue, a histidine (H) residue, and an aspartic acid (D) residue.

In embodiments, a comprises one or more hydrophilic residues, optionally selected from: a polar and positively charged hydrophilic amino acid, optionally selected from arginine (R) and lysine (K); a polar and neutral of charge hydrophilic amino acid, optionally selected from asparagine (N), glutamine (Q), serine (S), threonine (T), proline (P), and cysteine (C); a polar and negatively charged hydrophilic amino acid, optionally selected from aspartate (D) and glutamate (E), and an aromatic, polar and positively charged hydrophilic amino acid, optionally selected from histidine (H).

In some embodiments, a comprises one or more polar and positively charged hydrophilic amino acids selected from arginine (R) and lysine (K). In some embodiments, a comprises one or more polar and neutral of charge hydrophilic amino acids selected from asparagine (N), glutamine (Q), serine (S), threonine (T), proline (P), and cysteine (C). In some embodiments, a comprises one or more polar and negatively charged hydrophilic amino acids selected from aspartate (D) and glutamate (E). In some embodiments, a comprises one or more aromatic, polar and positively charged hydrophilic amino acids selected from histidine (H).

In embodiments, a comprises one or more hydrophobic residues, optionally selected from: a hydrophobic, aliphatic amino acid, optionally selected from glycine (G), alanine (A), leucine (L), isoleucine (I), methionine (M), and valine (V), and a hydrophobic, aromatic amino acid, optionally selected from phenylalanine (F), tryptophan (W), and tyrosine (Y). In some embodiments, a comprises one or more hydrophobic, aliphatic amino acids selected from glycine (G), alanine (A), leucine (L), isoleucine (I), methionine (M), and valine (V). In some embodiments, a comprises one or more aromatic amino acids selected from phenylalanine (F), tryptophan (W), and tyrosine (Y).

In embodiments, α is selected from GHGG (SEQ ID NO: 38), HGSG (SEQ ID NO: 39), HGGG (SEQ ID NO: 40), GGHD (SEQ ID NO: 41), GAHD (SEQ ID NO: 42), AHDG (SEQ ID NO: 43), PHDG (SEQ ID NO: 44), GPHD (SEQ ID NO: 45), GHGP (SEQ ID NO: 46), PHGG (SEQ ID NO: 47), PHGP (SEQ ID NO: 48), AHGA (SEQ ID NO: 49), LHGA (SEQ ID NO: 50), VHGA (SEQ ID NO: 51), IVHG (SEQ ID NO: 52), IHGM (SEQ ID NO: 53), RHGD (SEQ ID NO: 54), RDHG (SEQ ID NO: 55), RHGE (SEQ ID NO: 56), HRGE (SEQ ID NO: 57), HRGD (SEQ ID NO: 58), GPYE (SEQ ID NO: 59), NHGG (SEQ ID NO: 60), THGG (SEQ ID NO: 61), GTHG (SEQ ID NO: 62), GSGS (SEQ ID NO: 63), GSGG (SEQ ID NO: 64), GGGG (SEQ ID NO: 65), GRGG (SEQ ID NO: 66), and GKGG (SEQ ID NO: 67).

In embodiments, the synthetic RNA molecule is mRNA.

In embodiments, the DNA-binding domain comprises about 15, or about, 16, or about 17, or about 18, or about 18.5 repeat sequences.

In aspects, the present invention relates to a cell comprising any of the disclosed compositions.

In some embodiments, the gene-editing protein is tested for activity using a cell-free Amplicon-Cutting assay (cfACA) wherein, the gene-editing protein is translated from mRNA. In some embodiments, the gene-editing protein is tested for activity under conditions, wherein dCTP is replaced by 5m-dCTP to create an amplicon that mimics hypermethylated DNA in the target region and outside the target region. In some embodiments, the gene-editing protein is tested for activity under conditions, wherein 100% 5m-dCTP mimics hypermethylated target DNA and 0% 5m-dCTP mimics unmethylated target DNA. In some embodiments, the gene-editing proteins do not cleave hypermethylated sites, but only cleaved unmethylated sites, indicating that such activity does not result in off-target cutting.

Novel Engineered Nuclease Domains (Comprising Catalytic Domains)

In embodiments, any of the following nuclease domains find use in the present application: StsI, StsI-HA, StsI-HA2, StsI-UHA, StsI-UHA2, StsI-HF, and StsI-UHF. See Table 1. In some embodiments, StsI-HA, StsI-HA2 (high activity), StsI-UHA, and StsI-UHA2 (ultra-high activity) exhibit higher on-target activity than both wild-type StsI and wild-type FokI, due in part to specific amino-acid substitutions within the N-terminal region at the 34 and 61 positions, while StsI-HF (high fidelity) and StsI-UHF (ultra-high fidelity) exhibit lower off-target activity than both wild-type StsI and wild-type FokI, due in part to specific amino-acid substitutions within the C-terminal region at the 141 and 152 positions. Certain embodiments are therefore directed to a protein that comprises a nuclease domain. In one embodiment, the nuclease domain comprises one or more of: the cleavage domain of FokI endonuclease, the cleavage domain of StsI endonuclease, StsI-HA, StsI-HA2, StsI-UHA, StsI-UHA2, StsI-HF, and StsI-UHF or a biologically active fragment or variant thereof.

TABLE 1

| | |
|---|---|
| StsI endo-nuclease cleavage domain | Val Leu Glu Lys Ser Asp Ile Glu Lys Phe Lys Asn Gln Leu Arg Thr Glu Leu Thr Asn Ile Asp His Ser Tyr Leu Lys Gly Ile Asp Ile Ala Ser Lys Lys Lys Thr Ser Asn Val Glu Asn Thr Glu Phe Glu Ala Ile Ser Thr Lys Ile Phe Thr Asp Glu Leu Gly Phe Ser Gly Lys His Leu Gly Gly Ser Asn Lys Pro Asp Gly Leu Leu Trp Asp Asp Asp Cys Ala Ile Ile Leu Asp Ser Lys Ala Tyr Ser Glu Gly Phe Pro Leu Thr Ala Ser His Thr Asp Ala Met Gly Arg Tyr Leu Arg Gln Phe Thr Glu Arg Lys Glu Glu Ile Lys Pro Thr Trp Trp Asp Ile Ala Pro Glu His Leu Asp Asn Thr Tyr Phe Ala Tyr Val Ser Gly Ser Phe Ser Gly Asn Tyr Lys Glu Gln Leu Gln Lys Phe Arg Gln Asp Thr Asn His Leu Gly Gly Ala Leu Glu Phe Val Lys Leu Leu Leu Leu Ala Asn Asn Tyr Lys Thr Gln Lys Met Ser Lys Lys Glu Val Lys Lys Ser Ile Leu Asp Tyr Asn Ile Ser Tyr (SEQ ID NO: 68) |
| StsI-HA (high activity) | Val Leu Glu Lys Ser Asp Ile Glu Lys Phe Lys Asn Gln Leu Arg Thr Glu Leu Thr Asn Ile Asp His Ser Tyr Leu Lys Gly Ile Asp Ile Ala Ser Lys Lys Lys Thr Ser Asn Val Glu Asn Thr Glu Phe Glu Ala Ile Ser Thr Lys Ile Phe Thr Asp Glu Leu Gly Phe Ser Gly Glu His Leu Gly Gly Ser Asn Lys Pro Asp Gly Leu Leu Trp Asp Asp Asp Cys Ala Ile Ile Leu Asp Ser Lys Ala Tyr Ser Glu Gly Phe Pro Leu Thr Ala Ser His Thr Asp Ala Met Gly Arg Tyr Leu Arg Gln Phe Thr Glu Arg Lys Glu Glu Ile Lys Pro Thr Trp Trp Asp Ile Ala Pro Glu His Leu Asp Asn Thr Tyr Phe Ala Tyr Val Ser Gly Ser Phe Ser Gly Asn Tyr Lys Glu Gln Leu Gln Lys Phe Arg Gln Asp Thr Asn His Leu Gly Gly Ala Leu Glu Phe Val Lys Leu Leu Leu Leu Ala Asn Asn Tyr Lys Thr Gln Lys Met Ser Lys Lys Glu Val Lys Lys Ser Ile Leu Asp Tyr Asn Ile Ser Tyr (SEQ ID NO: 69) |
| StsI-HA2 (high activity) | Val Leu Glu Lys Ser Asp Ile Glu Lys Phe Lys Asn Gln Leu Arg Thr Glu Leu Thr Asn Ile Asp His Ser Tyr Leu Lys Gly Ile Asp Ile Ala Ser Lys Pro Lys Thr Ser Asn Val Glu Asn Thr Glu Phe Glu Ala Ile Ser Thr Lys Ile Phe Thr Asp Glu Leu Gly Phe Ser Gly Lys His Leu Gly Gly Ser Asn Lys Pro Asp Gly Leu Leu Trp Asp Asp Asp Cys Ala Ile Ile Leu Asp Ser Lys Ala Tyr Ser Glu Gly Phe Pro Leu Thr Ala Ser His Thr Asp Ala Met Gly Arg Tyr Leu Arg Gln Phe Thr Glu Arg Lys Glu Glu Ile Lys Pro Thr Trp Trp Asp Ile Ala Pro Glu His Leu Asp Asn Thr Tyr Phe Ala Tyr Val Ser Gly Ser Phe Ser Gly Asn Tyr Lys Glu Gln Leu Gln Lys Phe Arg Gln Asp Thr Asn His Leu Gly Gly Ala Leu Glu Phe Val Lys Leu Leu Leu Leu Ala Asn Asn Tyr Lys Thr Gln Lys Met Ser Lys Lys Glu Val Lys Lys Ser Ile Leu Asp Tyr Asn Ile Ser Tyr (SEQ ID NO: 70) |
| StsI-UHA (ultra-high activity) | Val Leu Glu Lys Ser Asp Ile Glu Lys Phe Lys Asn Gln Leu Arg Thr Glu Leu Thr Asn Ile Asp His Ser Tyr Leu Lys Gly Ile Asp Ile Ala Ser Lys Pro Lys Thr Ser Asn Val Glu Asn Thr Glu Phe Glu Ala Ile Ser Thr Lys Ile Phe Thr Asp Glu Leu Gly Phe Ser Gly Glu His Leu Gly Gly Ser Asn Lys Pro Asp Gly Leu Leu Trp Asp Asp Asp Cys Ala Ile Ile Leu Asp Ser Lys Ala Tyr Ser Glu Gly Phe Pro Leu Thr Ala Ser His Thr Asp Ala Met Gly Arg Tyr Leu Arg Gln Phe Thr Glu Arg Lys Glu Glu Ile Lys Pro Thr Trp Trp Asp Ile Ala Pro Glu His Leu Asp Asn Thr Tyr Phe Ala Tyr Val Ser Gly Ser Phe Ser Gly Asn Tyr Lys Glu Gln Leu Gln Lys Phe Arg Gln Asp Thr Asn His Leu Gly Gly Ala Leu Glu Phe Val Lys Leu Leu Leu Leu Ala Asn Asn Tyr Lys Thr Gln Lys Met Ser Lys Lys Glu Val Lys Lys Ser Ile Leu Asp Tyr Asn Ile Ser Tyr (SEQ ID NO: 71) |
| StsI-UHA2 (ultra-high activity) | Val Leu Glu Lys Ser Asp Ile Glu Lys Phe Lys Asn Gln Leu Arg Thr Glu Leu Thr Asn Ile Asp His Ser Tyr Leu Lys Gly Ile Asp Ile Ala Ser Lys Pro Val Glu Asn Thr Glu Phe Glu Ala Ile Ser Thr Lys Ile Phe Thr Asp Glu Leu Gly Phe Ser Gly Glu His Leu Gly Gly Ser Asn Lys Pro Asp Gly Leu Leu Trp Asp Asp Asp Cys Ala Ile Ile Leu Asp Ser Lys Ala Tyr Ser Glu Gly Phe Pro Leu Thr Ala Ser His Thr Asp Ala Met Gly Arg Tyr Leu Arg Gln Phe Thr Glu Arg Lys Glu Glu Ile Lys Pro Thr Trp Trp Asp Ile Ala Pro Glu His Leu Asp Asn Thr Tyr Phe Ala Tyr Val Ser Gly Ser Phe Ser Gly Asn Tyr Lys Glu Gln Leu Gln Lys Phe Arg Gln Asp Thr Asn His Leu Gly Gly Ala Leu Glu Phe Val Lys Leu Leu Leu Leu Ala Asn Asn Tyr Lys Thr Gln Lys Met Ser Lys Lys Glu Val Lys Lys Ser Ile Leu Asp Tyr Asn Ile Ser Tyr (SEQ ID NO: 72) |
| StsI-HF (high fidelity) | Val Leu Glu Lys Ser Asp Ile Glu Lys Phe Lys Asn Gln Leu Arg Thr Glu Leu Thr Asn Ile Asp His Ser Tyr Leu Lys Gly Ile Asp Ile Ala Ser Lys Lys Lys Thr Ser Asn Val Glu Asn Thr Glu Phe Glu Ala Ile Ser Thr Lys Ile Phe Thr Asp Glu Leu Gly Phe Ser Gly Lys His Leu Gly Gly Ser Asn Lys Pro Asp Gly Leu Leu Trp Asp Asp Asp Cys Ala Ile Ile Leu Asp Ser Lys Ala Tyr Ser Glu Gly Phe Pro Leu Thr Ala Ser His Thr Asp Ala Met Gly Arg Tyr Leu Arg Gln Phe Thr Glu Arg Lys Glu Glu Ile Lys Pro Thr Trp Trp Asp Ile Ala Pro Glu His Leu Asp Asn Thr Tyr Phe Ala Tyr Val Ser Gly Ser Phe Ser Gly Asp Tyr Lys Glu Gln Leu Gln Lys Phe Arg Gln Asp Thr Asn His Leu Gly Gly Ala Leu Glu Phe Val Lys Leu Leu Leu Leu Ala Asn Asn Tyr Lys Thr Gln Lys Met Ser Lys Lys Glu Val Lys Lys Ser Ile Leu Asp Tyr Asn Ile Ser Tyr (SEQ ID NO: 73) |

TABLE 1-continued

| | |
|---|---|
| Stsl-UHF<br>(ultra<br>high<br>fidelity) | Val Leu Glu Lys Ser Asp Ile Glu Lys Phe Lys Asn Gln Leu Arg Thr Glu Leu Thr Asn Ile Asp His<br>Ser Tyr Leu Lys Gly Ile Asp Ile Ala Ser Lys Lys Lys Thr Ser Asn Val Glu Asn Thr Glu Phe Glu<br>Ala Ile Ser Thr Lys Ile Phe Thr Asp Glu Leu Gly Phe Ser Gly Lys His Leu Gly Gly Ser Asn Lys<br>Pro Asp Gly Leu Leu Trp Asp Asp Asp Cys Ala Ile Ile Leu Asp Ser Lys Ala Tyr Ser Glu Gly Phe<br>Pro Leu Thr Ala Ser His Thr Asp Ala Met Gly Arg Tyr Leu Arg Gln Phe Thr Glu Arg Lys Glu Glu<br>Ile Lys Pro Thr Trp Trp Asp Ile Ala Pro Glu His Leu Asp Asn Thr Tyr Phe Ala Tyr Val Ser Gly<br>Ser Phe Ser Gly Asp Tyr Lys Glu Gln Leu Gln Lys Phe Arg Gln Asn Thr Asn His Leu Gly Gly<br>Ala Leu Glu Phe Val Lys Leu Leu Leu Leu Ala Asn Asn Tyr Lys Thr Gln Lys Met Ser Lys Lys<br>Glu Val Lys Lys Ser Ile Leu Asp Tyr Asn Ile Ser Tyr (SEQ ID NO: 74) |
| FokI<br>endo-<br>nuclease | Gln Leu Val Lys Ser Glu Leu Glu Glu Lys Lys Ser Glu Leu Arg His Lys Leu Lys Tyr Val Pro His<br>Glu Tyr Ile Glu Leu Ile Glu Ile Ala Arg Asn Ser Thr Gln Asp Arg Ile Leu Glu Met Lys Val Met<br>Glu Phe Phe Met Lys Val Tyr Gly Tyr Arg Gly Lys His Leu Gly Gly Ser Arg Lys Pro Asp Gly Ala<br>Ile Tyr Thr Val Gly Ser Pro Ile Asp Tyr Gly Val Ile Val Asp Thr Lys Ala Tyr Ser Gly Gly Tyr<br>Asn Leu Pro Ile Gly Gln Ala Asp Glu Met Gln Arg Tyr Val Glu Glu Asn Gln Thr Arg Asn Lys His<br>Ile Asn Pro Asn Glu Trp Trp Lys Val Tyr Pro Ser Ser Val Thr Glu Phe Lys Phe Leu Phe Val Ser<br>Gly His Phe Lys Gly Asn Tyr Lys Ala Gln Leu Thr Arg Leu Asn His Ile Thr Asn Cys Asn Gly Ala<br>Val Leu Ser Val Glu Glu Leu Leu Ile Gly Gly Glu Met Ile Lys Ala Gly Thr Leu Thr Leu Glu Glu<br>Val Arg Arg Lys Phe Asn Asn Gly Glu Ile Asn Phe (SEQ ID NO: 75) |

In one embodiment, the nuclease domain comprises a hybrid or chimera of two of the cleavage domain of FokI endonuclease, the cleavage domain of StsI endonuclease, StsI-HA, StsI-HA2, StsI-UHA, StsI-UHA2, StsI-HF, and StsI-UHF or a biologically active fragment or variant thereof.

In another aspect, the invention relates to a composition comprising a nucleic acid encoding a gene-editing protein, the gene-editing protein comprising: (a) the DNA-binding domain comprising a plurality of repeat sequences and at least one of the repeat sequences comprises a repeat variable di-residue (RVD) at residue 12 or 13; and (b) the nuclease domain comprising a catalytic domain, the catalytic domain comprising a hybrid of the catalytic domains of FokI and StsI, comprising the α1, α2, α3, α4, α5, α6, β1, β2, β3, β4, β5, and β6 domains of FokI with at least one of the domains of FokI being substituted in whole or in part with the α1, α2, α3, α4, α5, α6, β1, β2, β3, β4, β5, and β6 domains of StsI and optionally comprising at least one mutation.

In embodiments, the catalytic domain comprises: α1, α2, α3, and α6 of FokI, α1, α2, α3, of FokI and α6 of StsI, α1 and α2 of FokI and α3 and α6 of StsI, α1 of FokI and α2, α3 and α6 of StsI, α1 of StsI and α2, α3 and α6 of FokI, α1 and α2 of StsI and α3 and α6 of FokI, α1, α2, α3, of StsI and α6 of FokI, or α1, α2, α3, and α6 of StsI. In embodiments, the catalytic domain comprises: α4 and α6 of FokI, α4 of FokI and α6 of StsI, α4 of StsI and α6 of FokI, or α4 and α6 of StsI.

In some embodiments, the catalytic domain comprises α1, α2, α3, and α6 of FokI. In some embodiments, the catalytic domain comprises α1, α2, α3, of FokI and α6 of StsI. In some embodiments, the catalytic domain comprises α1 and α2 of FokI and α3 and α6 of StsI. In some embodiments, the catalytic domain comprises α1 of FokI and α2, α3 and α6 of StsI. In some embodiments, the catalytic domain comprises α1 of StsI and α2, α3 and α6 of FokI. In some embodiments, the catalytic domain comprises α1 and α2 of StsI and α3 and α6 of FokI. In some embodiments, the catalytic domain comprises α1, α2, α3, of StsI and α6 of FokI. In some embodiments, the catalytic domain comprises α1, α2, α3, and α6 of StsI. In some embodiments, the catalytic domain comprises α4 and α6 of FokI. In some embodiments, the catalytic domain comprises α4 of FokI and α6 of StsI. In some embodiments, the catalytic domain comprises α4 of StsI and α6 of FokI. In some embodiments, the catalytic domain comprises α4 and α6 of StsI. See e.g., Wah et al. Structure of FokI has implications for DNA cleavage *PNAS* (1998) 95(18): 10564-10569; the contents of which are hereby incorporated by reference.

In some embodiments, the catalytic domain comprises β1, β2, β3, and β6 of FokI. In some embodiments, the catalytic domain comprises β1, β2, β3, of FokI and β6 of StsI. In some embodiments, the catalytic domain comprises β1 and β2 of FokI and β3 and β6 of StsI. In some embodiments, the catalytic domain comprises β1 of FokI and β2, 63 and β6 of StsI. In some embodiments, the catalytic domain comprises β1 of StsI and β2, 63 and β6 of FokI. In some embodiments, the catalytic domain comprises β1 and β2 of StsI and β3 and β6 of FokI. In some embodiments, the catalytic domain comprises β1, β2, β3, of StsI and β6 of FokI. In some embodiments, the catalytic domain comprises β1, β2, β3, and β6 of StsI. In some embodiments, the catalytic domain comprises β4 and β6 of FokI. In some embodiments, the catalytic domain comprises β4 of FokI and β6 of StsI. In some embodiments, the catalytic domain comprises β4 of StsI and β6 of FokI. In some embodiments, the catalytic domain comprises β4 and β6 of StsI.

Figure 6:
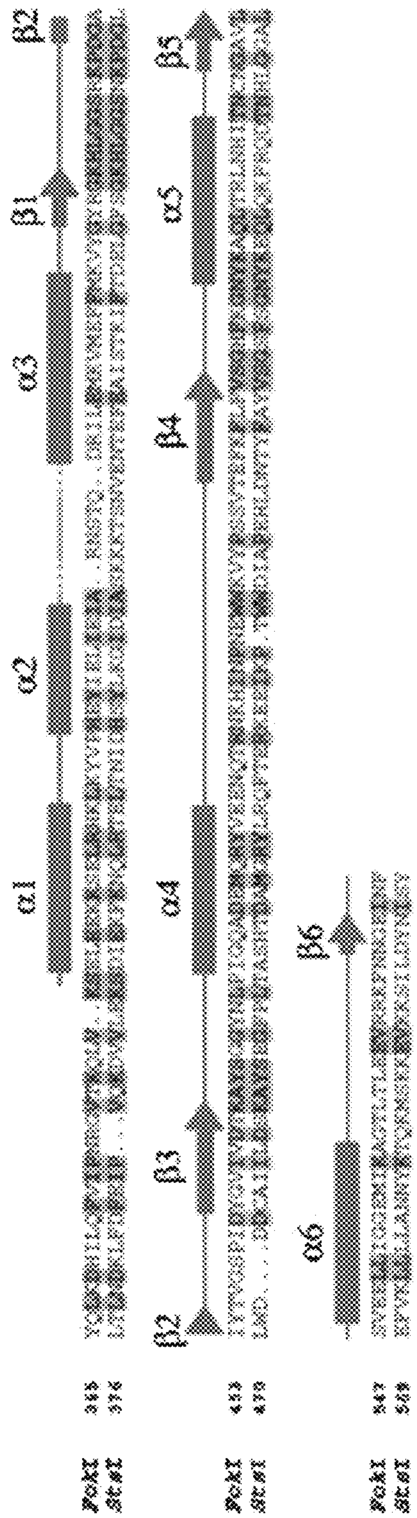
FIG. 6 depicts the aligned amino acid sequences of the C-terminal catalytic domains of FokI and StsI, with secondary structural domains indicated in blue.

In embodiments, the catalytic domains of FokI and StsI comprises the amino acids sequences of FIG. 6, or a sequence having at least about 95%, or at least about 97%, or at least about 98% identity thereto. In embodiments, the catalytic domain comprises one or more amino acid mutations, optionally selected from substitutions, insertions, deletions, and truncations, or combinations thereof.

In embodiments, the nuclease domain is capable of forming a dimer with another nuclease domain.

In embodiments, the gene-editing protein is capable of generating a nick or double-strand break in a target DNA molecule.

In embodiments, the RVD recognizes one base pair in the nucleic acid molecule. In embodiments, the RVD recognizes a C residue in the nucleic acid molecule and is selected from HD, N(null), HA, ND, and HI. In embodiments, the RVD recognizes a G residue in the nucleic acid molecule and is selected from NN, NH, NK, HN, and NA. In embodiments, the RVD recognizes an A residue in the nucleic acid molecule and is selected from NI and NS. In embodiments, the RVD recognizes a T residue in the nucleic acid molecule and is selected from NG, HG, H(null), and IG.

In some embodiments, the RVD recognizing a C residue in the nucleic acid molecule is HD. In some embodiments, the RVD recognizing a C residue in the nucleic acid molecule is N(null). In some embodiments, the RVD recognizing a C residue in the nucleic acid molecule is HA. In some embodiments, the RVD recognizing a C residue in the nucleic acid molecule is ND. In some embodiments, the RVD recognizing a C residue in the nucleic acid molecule is HI. In some embodiments, the RVD recognizing a G residue in the nucleic acid molecule is NN. In some embodiments, the RVD recognizing a G residue in the nucleic acid molecule is NH. In some embodiments, the RVD recognizing a G residue in the nucleic acid molecule is NK. In some embodiments, the RVD recognizing a G residue in the nucleic acid molecule is HN. In some embodiments, the RVD recognizing a G residue in the nucleic acid molecule is NA. In some embodiments, the RVD recognizing an A residue in the nucleic acid molecule is NI. In some embodiments, the RVD recognizing an A residue in the nucleic acid molecule is NS. In some embodiments, the RVD recognizing a T residue in the nucleic acid molecule is NG. In some embodiments, the RVD recognizing a T residue in the nucleic acid molecule is HG. In some embodiments, the RVD recognizing a T residue in the nucleic acid molecule is H(null). In some embodiments, the RVD recognizing a T residue in the nucleic acid molecule is IG.

In embodiments, the repeat sequence is 33 or 34 amino acids long. In embodiments, the repeat sequence is 36-39 amino acids long. In some embodiments, the repeat sequence is 36 amino acids long. In some embodiments, the repeat sequence is 37 amino acids long. In some embodiments, the repeat sequence is 38 amino acids long. In some embodiments, the repeat sequence is 39 amino acids long.

In embodiments, the DNA-binding domain comprises a plurality of repeat sequences and at least one of the repeat sequences comprises the amino acid sequence: LTPvQVVAIAwxyz (SEQ ID NO: 12), wherein: v is Q, D or E, w is S or N, x is I, H, N, or I, y is D, A, I, N, H, K, S, G or null, and z is GGRPALE (SEQ ID NO: 1), GGKQALE (SEQ ID NO: 2), GGKQALETVQRLLPVLCQDHG (SEQ ID NO: 3), GGKQALETVQRLLPVLCQAHG (SEQ ID NO: 4), GKQALETVQRLLPVLCQDHG (SEQ ID NO: 5), GKQALETVQRLLPVLCQAHG (SEQ ID NO: 6), GGKQALETVQRLLPVLCQD (SEQ ID NO: 7) or GGKQALETVQRLLPVLCQA (SEQ ID NO: 8).

In embodiments, at least one of the repeat sequences comprises the amino acid sequence: LTPvQVVAIAwxyzα (SEQ ID NO: 11), wherein: v is Q, D or E, w is S or N, x is I, H, N, or I, y is D, A, I, N, H, K, S, G or null, z is GGRPALE (SEQ ID NO: 1), GGKQALE (SEQ ID NO: 2), GGKQALETVQRLLPVLCQDHG (SEQ ID NO: 3), GGKQALETVQRLLPVLCQAHG (SEQ ID NO: 4), GKQALETVQRLLPVLCQDHG (SEQ ID NO: 5), GKQALETVQRLLPVLCQAHG (SEQ ID NO: 6), GGKQALETVQRLLPVLCQD (SEQ ID NO: 7) or GGKQALETVQRLLPVLCQA (SEQ ID NO: 8), and α is any four consecutive amino acids.

In some embodiments, z is GGRPALE (SEQ ID NO: 1) and α is null. In some embodiments, z is GGKQALE (SEQ ID NO: 2) and α is null. In some embodiments, z is GGKQALETVQRLLPVLCQDHG (SEQ ID NO: 3) and α is null. In some embodiments, z is GGKQALETVQRLLPVLCQAHG (SEQ ID NO: 4) and α is null. In some embodiments, z is GKQALETVQRLLPVLCQDHG (SEQ ID NO: 5) and α is null. In some embodiments, z is GKQALETVQRLLPVLCQAHG (SEQ ID NO: 6) and α is null. In some embodiments, z is GGKQALETVQRLLPVLCQD (SEQ ID NO: 7) and α is null. In some embodiments, z is GGKQALETVQRLLPVLCQA (SEQ ID NO: 8) and α is null.

In some embodiments, z is GGRPALE (SEQ ID NO: 1). In some embodiments, z is GGKQALE (SEQ ID NO: 2). In some embodiments, z is GGKQALETVQRLLPVLCQDHG (SEQ ID NO: 3). In some embodiments, z is GGKQALETVQRLLPVLCQAHG (SEQ ID NO: 4). In some embodiments, z is GKQALETVQRLLPVLCQDHG (SEQ ID NO: 5). In some embodiments, z is GKQALETVQRLLPVLCQAHG (SEQ ID NO: 6). In some embodiments, z is GGKQALETVQRLLPVLCQD (SEQ ID NO: 7). In some embodiments, z is GGKQALETVQRLLPVLCQA (SEQ ID NO: 8).

In embodiments, a comprises at least one glycine (G) residue. In embodiments, a comprises at least one histidine (H) residue. In embodiments, a comprises at least one histidine (H) residue at any one of positions 33, 34, or 35. In embodiments, a comprises at least one aspartic acid (D) residue. In embodiments, a comprises at least one, or two, or three of a glycine (G) residue, a histidine (H) residue, and an aspartic acid (D) residue.

In embodiments, a comprises one or more hydrophilic residues, optionally selected from: a polar and positively charged hydrophilic amino acid, optionally selected from arginine (R) and lysine (K); a polar and neutral of charge hydrophilic amino acid, optionally selected from asparagine (N), glutamine (Q), serine (S), threonine (T), proline (P), and cysteine (C); a polar and negatively charged hydrophilic amino acid, optionally selected from aspartate (D) and glutamate (E), and an aromatic, polar and positively charged hydrophilic amino acid, optionally selected from histidine (H).

In some embodiments, a comprises one or more polar and positively charged hydrophilic amino acids selected from arginine (R) and lysine (K). In some embodiments, a comprises one or more polar and neutral of charge hydrophilic amino acids selected from asparagine (N), glutamine (Q), serine (S), threonine (T), proline (P), and cysteine (C). In some embodiments, a comprises one or more polar and negatively charged hydrophilic amino acids selected from aspartate (D) and glutamate (E). In some embodiments, a comprises one or more aromatic, polar and positively charged hydrophilic amino acids selected from histidine (H).

In embodiments, a comprises one or more hydrophobic residues, optionally selected from: a hydrophobic, aliphatic amino acid, optionally selected from glycine (G), alanine (A), leucine (L), isoleucine (I), methionine (M), and valine (V), and a hydrophobic, aromatic amino acid, optionally selected from phenylalanine (F), tryptophan (W), and tyrosine (Y). In some embodiments, a comprises one or more hydrophobic, aliphatic amino acids selected from glycine (G), alanine (A), leucine (L), isoleucine (I), methionine (M), and valine (V). In some embodiments, a comprises one or more aromatic amino acids selected from phenylalanine (F), tryptophan (W), and tyrosine (Y).

In embodiments, α is selected from GHGG (SEQ ID NO: 38), HGSG (SEQ ID NO: 39), HGGG (SEQ ID NO: 40), GGHD (SEQ ID NO: 41), GAHD (SEQ ID NO: 42), AHDG (SEQ ID NO: 43), PHDG (SEQ ID NO: 44), GPHD (SEQ ID NO: 45), GHGP (SEQ ID NO: 46), PHGG (SEQ ID NO: 47), PHGP (SEQ ID NO: 48), AHGA (SEQ ID NO: 49), LHGA (SEQ ID NO: 50), VHGA (SEQ ID NO: 51), IVHG (SEQ ID NO: 52), IHGM (SEQ ID NO: 53), RHGD (SEQ ID NO: 54), RDHG (SEQ ID NO: 55), RHGE (SEQ ID NO: 56), HRGE (SEQ ID NO: 57), HRGD (SEQ ID NO: 58), GPYE (SEQ ID NO: 59), NHGG (SEQ ID NO: 60), THGG (SEQ ID NO: 61), GTHG (SEQ ID NO: 62), GSGS (SEQ ID NO: 63), GSGG (SEQ ID NO: 64), GGGG (SEQ ID NO: 65), GRGG (SEQ ID NO: 66), and GKGG (SEQ ID NO: 67).

In embodiments, the nucleic acid is a synthetic RNA molecule. In embodiments, the synthetic RNA molecule is mRNA.

In embodiments, the DNA-binding domain comprises about 15, or about, 16, or about 17, or about 18, or about 18.5 repeat sequences.

In aspects, the present invention relates to a cell comprising any of the disclosed compositions.

In some embodiments, the gene-editing protein is tested for activity using a cell-free Amplicon-Cutting assay (cfACA) for rapid screening.

Novel Engineered DNA-Binding Domains

In one aspect, the invention relates to a composition comprising a nucleic acid encoding a gene-editing protein, the gene-editing protein comprising: (a) the DNA-binding domain comprising a plurality of repeat sequences and at least one of the repeat sequences comprises the amino acid sequence: LTPvQVVAIAwxyzα (SEQ ID NO: 11) and is between 36 and 39 amino acids long, wherein: v is Q, D or E, w is S or N, x is I, H, N, or I, y is D, A, I, N, H, K, S, G or null, z is GGRPALE (SEQ ID NO: 1), GGKQALE (SEQ ID NO: 2), GGKQALETVQRLLPVLCQDHG (SEQ ID NO: 3), GGKQALETVQRLLPVLCQAHG (SEQ ID NO: 4), GKQALETVQRLLPVLCQDHG (SEQ ID NO: 5), GKQALETVQRLLPVLCQAHG (SEQ ID NO: 6), GGKQALETVQRLLPVLCQD (SEQ ID NO: 7) or GGKQALETVQRLLPVLCQA (SEQ ID NO: 8), α is four consecutive amino acids, with the proviso that α is not GHGG (SEQ ID NO: 38), HGSG (SEQ ID NO: 39), and HGGG (SEQ ID NO: 40); and (b) the nuclease domain comprising a catalytic domain of a nuclease.

In another aspect, the invention relates to a composition comprising a nucleic acid encoding a gene-editing protein, the gene-editing protein comprising: (a) the DNA-binding domain comprises a plurality of repeat sequences and at least one of the repeat sequences comprises the amino acid sequence of between 36 and 39 amino acids long, of which the four most C-terminal amino acids are selected from GGHD (SEQ ID NO: 41), GAHD (SEQ ID NO: 42), AHDG (SEQ ID NO: 43), PHDG (SEQ ID NO: 44), GPHD (SEQ ID NO: 45), GHGP (SEQ ID NO: 46), PHGG (SEQ ID NO: 47), PHGP (SEQ ID NO: 48), AHGA (SEQ ID NO: 49), LHGA (SEQ ID NO: 50), VHGA (SEQ ID NO: 51), IVHG (SEQ ID NO: 52), IHGM (SEQ ID NO: 53), RHGD (SEQ ID NO: 54), RDHG (SEQ ID NO: 55), RHGE (SEQ ID NO: 56), HRGE (SEQ ID NO: 57), HRGD (SEQ ID NO: 58), GPYE (SEQ ID NO: 59), NHGG (SEQ ID NO: 60), THGG (SEQ ID NO: 61), GTHG (SEQ ID NO: 62), GSGS (SEQ ID NO: 63), GSGG (SEQ ID NO: 64), GGGG (SEQ ID NO: 65), GRGG (SEQ ID NO: 66), and GKGG (SEQ ID NO: 67); and (b) the nuclease domain comprises a catalytic domain of a nuclease.

In some embodiments, z is GGRPALE (SEQ ID NO: 1) and α is null. In some embodiments, z is GGKQALE (SEQ ID NO: 2) and α is null. In some embodiments, z is GGKQALETVQRLLPVLCQDHG (SEQ ID NO: 3) and α is null. In some embodiments, z is GGKQALETVQRLLPVLCQAHG (SEQ ID NO: 4) and α is null. In some embodiments, z is GKQALETVQRLLPVLCQDHG (SEQ ID NO: 5) and α is null. In some embodiments, z is GKQALETVQRLLPVLCQAHG (SEQ ID NO: 6) and α is null. In some embodiments, z is GGKQALETVQRLLPVLCQD (SEQ ID NO: 7) and α is null.

In some embodiments, z is GGKQALETVQRLLPVLCQA (SEQ ID NO: 8) and α is null.

In some embodiments, z is GGRPALE (SEQ ID NO: 1). In some embodiments, z is GGKQALE (SEQ ID NO: 2). In some embodiments, z is GGKQALETVQRLLPVLCQDHG (SEQ ID NO: 3). In some embodiments, z is GGKQALETVQRLLPVLCQAHG (SEQ ID NO: 4). In some embodiments, z is GKQALETVQRLLPVLCQDHG (SEQ ID NO: 5). In some embodiments, z is GKQALETVQRLLPVLCQAHG (SEQ ID NO: 6). In some embodiments, z is GGKQALETVQRLLPVLCQD (SEQ ID NO: 7). In some embodiments, z is GGKQALETVQRLLPVLCQA (SEQ ID NO: 8).

In embodiments, a comprises at least one glycine (G) residue. In embodiments, a comprises at least one histidine (H) residue. In embodiments, a comprises at least one histidine (H) residue at any one of positions 33, 34, or 35. In embodiments, a comprises at least one aspartic acid (D) residue. In embodiments, a comprises at least one, or two, or three of a glycine (G) residue, a histidine (H) residue, and an aspartic acid (D) residue.

In embodiments, a comprises one or more hydrophilic residues, optionally selected from: a polar and positively charged hydrophilic amino acid, optionally selected from arginine (R) and lysine (K); a polar and neutral of charge hydrophilic amino acid, optionally selected from asparagine (N), glutamine (Q), serine (S), threonine (T), proline (P), and cysteine (C); a polar and negatively charged hydrophilic amino acid, optionally selected from aspartate (D) and glutamate (E), and an aromatic, polar and positively charged hydrophilic amino acid, optionally selected from histidine (H).

In some embodiments, a comprises one or more polar and positively charged hydrophilic amino acids selected from arginine (R) and lysine (K). In some embodiments, a comprises one or more polar and neutral of charge hydrophilic amino acids selected from asparagine (N), glutamine (Q), serine (S), threonine (T), proline (P), and cysteine (C). In some embodiments, a comprises one or more polar and negatively charged hydrophilic amino acids selected from aspartate (D) and glutamate (E). In some embodiments, a comprises one or more aromatic, polar and positively charged hydrophilic amino acids selected from histidine (H).

In embodiments, a comprises one or more hydrophobic residues, optionally selected from: a hydrophobic, aliphatic amino acid, optionally selected from glycine (G), alanine (A), leucine (L), isoleucine (I), methionine (M), and valine (V), and a hydrophobic, aromatic amino acid, optionally selected from phenylalanine (F), tryptophan (W), and tyrosine (Y). In some embodiments, a comprises one or more hydrophobic, aliphatic amino acids selected from glycine (G), alanine (A), leucine (L), isoleucine (I), methionine (M), and valine (V). In some embodiments, a comprises one or more aromatic amino acids selected from phenylalanine (F), tryptophan (W), and tyrosine (Y).

In embodiments, the nuclease domain is capable of forming a dimer with another nuclease domain.

In embodiments, the nuclease is selected from FokI, StsI, or a hybrid thereof.

In embodiments, the gene-editing protein is capable of generating a nick or double-strand break in a target DNA molecule.

In embodiments, the nucleic acid is a synthetic RNA molecule. In embodiments, the synthetic RNA molecule is mRNA.

In embodiments, at least one of the repeat sequences contains a region capable of binding to a binding site in a target DNA molecule, the binding site containing a defined sequence of between 1 and 5 bases in length.

In embodiments, the DNA-binding domain comprises about 15, or about, 16, or about 17, or about 18, or about 18.5 repeat sequences.

In some embodiments, certain fragments of an endonuclease cleavage domain are used, including fragments that are truncated at the N-terminus, fragments that are truncated at the C-terminus, fragments that have internal deletions, and fragments that combine N-terminus, C-terminus, and/or internal deletions, which maintain part or all of the catalytic activity of the full endonuclease cleavage domain. Determining whether a fragment can maintain part or all of the catalytic activity of the full domain can be accomplished by, for example, synthesizing a gene-editing protein that contains the fragment according to the methods of the present invention, inducing cells to express the gene-editing protein according to the methods of the present invention, and measuring the efficiency of gene editing. In some embodiments, a measurement of gene-editing efficiency is used to ascertain whether any specific fragment maintains part or all of the catalytic activity of the full endonuclease cleavage domain. Certain embodiments are therefore directed to a biologically active fragment of an endonuclease cleavage domain. In one embodiment, the endonuclease cleavage domain is selected from: FokI, StsI, StsI-HA, StsI-HA2, StsI-UHA, StsI-UHA2, StsI-HF, and StsI-UHF or a natural or engineered variant or biologically active fragment thereof, or a hybrid or chimera thereof.

In some embodiments, certain fragments of a DNA-binding domain or repeat sequence are used, including fragments that are truncated at the N-terminus, fragments that are truncated at the C-terminus, fragments that have internal deletions, and fragments that combine N-terminus, C-terminus, and/or internal deletions, which maintain part or all of the binding activity of the full DNA-binding domain or repeat sequence. Examples of fragments of DNA-binding domains or repeat sequences that can maintain part or all of the binding activity of the full repeat sequence include *Ralstonia solanacearum* TALE-like proteins (RTLs). Determining whether a fragment can maintain part or all of the binding activity of the full DNA-binding domain or repeat sequence can be accomplished by, for example, synthesizing a gene-editing protein that contains the fragment according to the methods of the present invention, inducing cells to express the gene-editing protein according to the methods of the present invention, and measuring the efficiency of gene editing.

In some embodiments, a measurement of gene-editing efficiency is used to ascertain whether any specific fragment can maintain part or all of the binding activity of the full DNA-binding domain or repeat sequence. Certain embodiments are therefore directed to a biologically active fragment of a DNA-binding domain or repeat sequence. In one embodiment, the fragment enables high-specificity recognition of a binding site in a target DNA molecule. In another embodiment, the fragment comprises a sequence that encodes a *Ralstonia solanacearum* TALE-like protein or a biologically active fragment thereof.

Alternative DNA Binding Domains

In some embodiments, alternative DNA binding domains are employed.

For example, the alternative DNA binding domains described herein are, in embodiments, paired with the novel engineered nuclease domains described herein.

For example, the alternative DNA binding domains described herein are, in embodiments, used in the conditional activity: temperature dependence methods described herein For example, the alternative DNA binding domains described herein are, in embodiments, used in the conditional activity: methylation status methods described herein In some embodiments, engineered gene-editing proteins that comprise DNA-binding domains comprising certain novel repeat sequences exhibit lower off-target activity than previously disclosed gene-editing proteins, while maintaining a high level of on-target activity. Certain of these engineered gene-editing proteins can provide several advantages over previously disclosed gene-editing proteins, including, for example, increased flexibility of the linker region connecting repeat sequences, which can result in increased binding efficiency. Certain embodiments are therefore directed to a protein comprising a plurality of repeat sequences. In one embodiment, at least one of the repeat sequences contains the amino-acid sequence: GabG, where "a" and "b" each represent any amino acid. In one embodiment, the protein is a gene-editing protein. In another embodiment, one or more of the repeat sequences are present in a DNA-binding domain. In a further embodiment, "a" and "b" are each independently selected from the group: H and G. In a still further embodiment, "a" and "b" are H and G, respectively. In one embodiment, the amino-acid sequence is present within about 5 amino acids of the C-terminus of the repeat sequence. In another embodiment, the amino-acid sequence is present at the C-terminus of the repeat sequence. In some embodiments, one or more G in the amino-acid sequence GabG is replaced with one or more amino acids other than G, for example A, H or GG. In one embodiment, the repeat sequence has a length of between about 32 and about 40 amino acids or between about 33 and about 39 amino acids or between about 34 and 38 amino acids or between about 35 and about 37 amino acids or about 36 amino acids or greater than about 32 amino acids or greater than about 33 amino acids or greater than about 34 amino acids or greater than about 35 amino acids. Other embodiments are directed to a protein comprising one or more transcription activator-like effector domains. In one embodiment, at least one of the transcription activator-like effector domains comprises a repeat sequence. Other embodiments are directed to a protein comprising a plurality of repeat sequences generated by inserting one or more amino acids between at least two of the repeat sequences of a transcription activator-like effector domain. In one embodiment, one or more amino acids is inserted about 1 or about 2 or about 3 or about 4 or about 5 amino acids from the C-terminus of at least one repeat sequence. Still other embodiments are directed to a protein comprising a plurality of repeat sequences, wherein about every other repeat sequence has a different length than the repeat sequence immediately preceding or following the repeat sequence. In one embodiment, every other repeat sequence is about 36 amino acids long. In another embodiment, every other repeat sequence is 36 amino acids long. Still other embodiments are directed to a protein comprising a plurality of repeat sequences, wherein the plurality of repeat sequences comprises at least two repeat sequences that are each at least 36 amino acids long, and wherein at least two of the repeat sequences that are at least 36 amino acids long are separated by at least one repeat sequence that is less than 36 amino acids long.

Other embodiments are directed to a protein that comprises a DNA-binding domain. In some embodiments, the DNA-binding domain comprises a plurality of repeat sequences. In one embodiment, the plurality of repeat sequences enables high-specificity recognition of a binding site in a target DNA molecule. In another embodiment, at least two of the repeat sequences have at least about 50%, or about 60%, or about 70%, or about 80%, or about 90%, or about 95%, or about 98%, or about 99% homology to each other. In a further embodiment, at least one of the repeat sequences comprises one or more regions capable of binding to a binding site in a target DNA molecule. In a still further embodiment, the binding site comprises a defined sequence of between about 1 to about 5 bases in length. In one embodiment, the DNA-binding domain comprises a zinc finger. In another embodiment, the DNA-binding domain comprises a transcription activator-like effector (TALE). In a further embodiment, the plurality of repeat sequences includes at least one repeat sequence having at least about 50% or about 60% or about 70% or about 80% or about 90% or about 95% or about 98%, or about 99% homology to a TALE. In a still further embodiment, the gene-editing protein comprises a clustered regularly interspaced short palindromic repeat (CRISPR)-associated protein. In one embodiment, the gene-editing protein comprises a nuclear-localization sequence. In another embodiment, the nuclear-localization sequence comprises the amino-acid sequence: PKKKRKV (SEQ ID NO: 76). In one embodiment, the gene-editing protein comprises a mitochondrial-localization sequence. In another embodiment, the mitochondrial-localization sequence comprises the amino-acid sequence: LGRVIPRKIASRASLM (SEQ ID NO: 77). In one embodiment, the gene-editing protein comprises a linker. In another embodiment, the linker connects a DNA-binding domain to a nuclease domain. In a further embodiment, the linker is between about 1 and about 10 amino acids long. In some embodiments, the linker is about 1, about 2, or about 3, or about 4, or about 5, or about 6, or about 7, or about 8, or about 9, or about 10 amino acids long. In one embodiment, the gene-editing protein is capable of generating a nick or a double-strand break in a target DNA molecule.

Certain embodiments are directed to a nucleic acid molecule encoding a non-naturally occurring fusion protein comprising a first region that recognizes a predetermined nucleotide sequence and a second region with endonuclease activity, wherein the first region contains an artificial TAL effector repeat domain comprising one or more repeat units about 36 amino acids in length which differ from each other by no more than seven amino acids, and wherein the repeat domain is engineered for recognition of the predetermined nucleotide sequence. In one embodiment, the first region contains the amino acid sequence: LTPXQWAIAS (SEQ ID NO: 78) where X can be either E or Q. In another embodiment, the amino acid sequence LTPXQWAIAS (SEQ ID NO: 78) of the encoded non-naturally occurring fusion protein is immediately followed by an amino acid sequence selected from: HD, NG, NS, NI, NN, and N. In a further embodiment, the fusion protein comprises restriction endonuclease activity.

In one embodiment, the repeat sequence comprises: LTPvQVVAIAwxyzHG (SEQ ID NO: 13), wherein "v" is D or E, "w" is S or N, "x" is N, H or I, "y" is any amino acid or no amino acid, and "z" is GGRPALE (SEQ ID NO: 1), GGKQALE (SEQ ID NO: 2), GGKQALETVQRLLPVLCQDHG (SEQ ID NO: 3), GGKQALETVQRLLPVLCQAHG (SEQ ID NO: 4), GKQALETVQRLLPVLCQDHG (SEQ ID NO: 5), or GKQALETVQRLLPVLCQAHG (SEQ ID NO: 6). In another embodiment, the repeat sequence comprises: LTPvQVVAIAwxyzHG (SEQ ID NO: 14), wherein "v" is D or E, "w" is S or N, "x" is N, H or I, "y" is selected from: D, A, I, N, H, K, S, and G, and "z" is GGRPALE (SEQ ID NO: 1), GGKQALE (SEQ ID NO: 2), GGKQALETVQRLLPVLCQDHG (SEQ ID NO: 3), GGKQALETVQRLLPVLCQAHG (SEQ ID NO: 4), GKQALETVQRLLPVLCQDHG (SEQ ID NO: 5), or GKQALETVQRLLPVLCQAHG (SEQ ID NO: 6). In yet another embodiment, the repeat sequence comprises: LTPvQVVAIAwxyzHG (SEQ ID NO: 15), wherein "v" is D or E, "w" is S or N, "x" is any amino acid other than N, H and I, "y" is any amino acid or no amino acid, and "z" is GGRPALE (SEQ ID NO: 1), GGKQALE (SEQ ID NO: 2), GGKQALETVQRLLPVLCQDHG (SEQ ID NO: 3), GGKQALETVQRLLPVLCQAHG (SEQ ID NO: 4), GKQALETVQRLLPVLCQDHG (SEQ ID NO: 5), or GKQALETVQRLLPVLCQAHG (SEQ ID NO: 6). In yet another embodiment, the repeat sequence comprises: LTPvQVVAIAIwyzHG (SEQ ID NO: 16), wherein "v" is D or E, "w" is S or N, "y" is any amino acid other than G, and "z" is GGRPALE (SEQ ID NO: 1), GGKQALE (SEQ ID NO: 2), GGKQALETVQRLLPVLCQDHG (SEQ ID NO: 3), GGKQALETVQRLLPVLCQAHG (SEQ ID NO: 4), GKQALETVQRLLPVLCQDHG (SEQ ID NO: 5), or GKQALETVQRLLPVLCQAHG (SEQ ID NO: 6). In yet another embodiment, the repeat sequence comprises: LTPvQVVAIAwIAzHG, wherein "v" is D or E, "w" is S or N, and "z" is GGRPALE (SEQ ID NO: 1), GGKQALE (SEQ ID NO: 2), GGKQALETVQRLLPVLCQDHG (SEQ ID NO: 3), GGKQALETVQRLLPVLCQAHG (SEQ ID NO: 4), GKQALETVQRLLPVLCQDHG (SEQ ID NO: 5), or GKQALETVQRLLPVLCQAHG (SEQ ID NO: 6). In yet another embodiment, the repeat sequence comprises: LTPvQVVAIAwxyzHG (SEQ ID NO: 17), wherein "v" is D or E, "w" is S or N, "x" is S, T or Q, "y" is any amino acid or no amino acid, and "z" is GGRPALE (SEQ ID NO: 1), GGKQALE (SEQ ID NO: 2), GGKQALETVQRLLPVLCQDHG (SEQ ID NO: 3), GGKQALETVQRLLPVLCQAHG (SEQ ID NO: 4), GKQALETVQRLLPVLCQDHG (SEQ ID NO: 5), or GKQALETVQRLLPVLCQAHG (SEQ ID NO: 6). In yet another embodiment, the repeat sequence comprises: LTPvQVVAIAwxyzHG (SEQ ID NO: 18), wherein "v" is D or E, "w" is S or N, "x" is S, T or Q, "y" is selected from: D, A, I, N, H, K, S, and G, and "z" is GGRPALE (SEQ ID NO: 1), GGKQALE (SEQ ID NO: 2), GGKQALETVQRLLPVLCQDHG (SEQ ID NO: 3), GGKQALETVQRLLPVLCQAHG (SEQ ID NO: 4), GKQALETVQRLLPVLCQDHG (SEQ ID NO: 5), or GKQALETVQRLLPVLCQAHG (SEQ ID NO: 6). In yet another embodiment, the repeat sequence comprises: LTPvQVVAIAwx (SEQ ID NO: 19), wherein "v" is D or E, "w" is S or N, and "x" is S, T or Q. In yet another embodiment, the repeat sequence comprises: LTPvQVVAIAwxy (SEQ ID NO: 20), wherein "v" is D or E, "w" is S or N, "x" is S, T or Q, and "y" is selected from: D, A, I, N, H, K, S, and G. In yet another embodiment, the repeat sequence comprises: LTPvQVVAIAwxyzGHGG (SEQ ID NO: 21), wherein "v" is Q, D or E, "w" is S or N, "x" is N, H or I, "y" is any amino acid or no amino acid, and "z" is GGRPALE (SEQ ID NO: 1), GGKQALE (SEQ ID NO: 2), GGKQALETVQRLLPVLCQD (SEQ ID NO: 7), GGKQALETVQRLLPVLCQA (SEQ ID NO: 8), GKQALETVQRLLPVLCQD (SEQ ID NO: 9) or GKQALETVQRLLPVLCQA (SEQ ID NO: 10). In yet another embodiment, the repeat sequence comprises: LTPvQVVAIAwxyzGHGG (SEQ ID NO: 22), wherein "v" is Q, D or E, "w" is S or N, "x" is N, H or I, "y" is selected from: D, A, I, N, H, K, S, and G, and "z" is GGRPALE (SEQ ID NO: 1), GGKQALE (SEQ ID NO: 2), GGKQALETVQRLLPVLCQD (SEQ ID NO: 7), GGKQALETVQRLLPVLCQA (SEQ ID NO: 8), GKQALETVQRLLPVLCQD (SEQ ID NO: 9) or GKQALETVQRLLPVLCQA (SEQ ID NO: 10). In yet another embodiment, the repeat sequence comprises: LTPvQVVAIAwxyzGHGG (SEQ ID NO: 23), wherein "v" is Q, D or E, "w" is S or N, "x" is any amino acid other than N, H and I, "y" is any amino acid or no amino acid, and "z" is GGRPALE (SEQ ID NO: 1), GGKQALE (SEQ ID NO: 2), GGKQALETVQRLLPVLCQD (SEQ ID NO: 7), GGKQALETVQRLLPVLCQA (SEQ ID NO: 8), GKQALETVQRLLPVLCQD (SEQ ID NO: 9) or GKQALETVQRLLPVLCQA (SEQ ID NO: 10). In yet another embodiment, the repeat sequence comprises: LTPvQVVAIAwIyzGHGG (SEQ ID NO: 24), wherein "v" is Q, D or E, "w" is S or N, "y" is any amino acid other than G, and "z" is GGRPALE (SEQ ID NO: 1), GGKQALE (SEQ ID NO: 2), GGKQALETVQRLLPVLCQD (SEQ ID NO: 7), GGKQALETVQRLLPVLCQA (SEQ ID NO: 8), GKQALETVQRLLPVLCQD (SEQ ID NO: 9) or GKQALETVQRLLPVLCQA (SEQ ID NO: 10). In yet another embodiment, the repeat sequence comprises: LTPvVVAIAwIAzGHGG (SEQ ID NO: 25), wherein "v" is Q, D or E, "w" is S or N, and "z" is GGRPALE (SEQ ID NO: 1), GGKQALE (SEQ ID NO: 2), GGKQALETVQRLLPVLCQD (SEQ ID NO: 7), GGKQALETVQRLLPVLCQA (SEQ ID NO: 8), GKQALETVQRLLPVLCQD (SEQ ID NO: 9) or GKQALETVQRLLPVLCQA (SEQ ID NO: 10). In yet another embodiment, the repeat sequence comprises: LTPvQVVAIAwxyzGHGG (SEQ ID NO: 26), wherein "v" is Q, D or E, "w" is S or N, "x" is S, T or Q, "y" is any amino acid or no amino acid, and "z" is GGRPALE (SEQ ID NO: 1), GGKQALE (SEQ ID NO: 2), GGKQALETVQRLLPVLCQD (SEQ ID NO: 7), GGKQALETVQRLLPVLCQA (SEQ ID NO: 8), GKQALETVQRLLPVLCQD (SEQ ID NO: 9) or GKQALETVQRLLPVLCQA (SEQ ID NO: 10). In yet another embodiment, the repeat sequence comprises: LTPvQVVAIAwxyzGHGG (SEQ ID NO: 27), wherein "v" is Q, D or E, "w" is S or N, "x" is S, T or Q, "y" is selected from: D, A, I, N, H, K, S, and G, and "z" is GGRPALE (SEQ ID NO: 1), GGKQALE (SEQ ID NO: 2), GGKQALETVQRLLPVLCQD (SEQ ID NO: 7), GGKQALETVQRLLPVLCQA (SEQ ID NO: 8), GKQALETVQRLLPVLCQD (SEQ ID NO: 9) or GKQALETVQRLLPVLCQA (SEQ ID NO: 10). In yet another embodiment, the repeat sequence comprises: LTPvQVVAIAwx (SEQ ID NO: 19), wherein "v" is Q, D or E, "w" is S or N, and "x" is S, T or Q. In yet another embodiment, the repeat sequence comprises: LTPvQVVAIAwxy (SEQ ID NO: 28), wherein "v" is Q, D or E, "w" is S or N, "x" is S, T or Q, and "y" is selected from: D, A, I, N, H, K, S, and G.

$T_0$-Independent DNA Binding Domains

In some embodiments, alternative DNA binding domains are employed.

For example, the alternative DNA binding domains described herein are, in embodiments, paired with the novel engineered nuclease domains described herein.

For example, the alternative DNA binding domains described herein are, in embodiments, used in the conditional activity: temperature dependence methods described herein For example, the alternative DNA binding domains described herein are, in embodiments, used in the conditional activity: methylation status methods described herein.

In embodiments, the engineered gene-editing proteins do not require a thymine (T) in the zero position of the target site ("$T_0$").

In embodiments, the engineered gene-editing proteins that comprise DNA-binding domains comprise alterations in the in the N-terminal region to remove the $T_0$ requirement.

In embodiments, there is provided a method of gene-editing a cell with one or more of the present gene-editing proteins, optionally with also using a linear DNA repair template, optionally also using conditional activity methods described herein, where the target site lacks a thymine (T) in the zero position.

Wild type N-terminal region is characterized by the sequence: Asp225-IVGVGKQWSGARAL-Glu240 (SEQ ID NO: 29).

In embodiments, there is provided the engineered N-terminal region of Asp225-IVGVGKQKRGARAL-Glu240 (underling showing the change WS→KR; SEQ ID NO: 30).

In embodiments, there is provided an engineered N-terminal region in which KQWS is replaced with one or more amino acids, e.g. about 2-10 amino acids, or about 4-10 amino acids, or about 6-10 amino acids, or about 8-10 amino acids, or about 4 amino acids, or about 6 amino acids, or about 8 amino acids, or about 10 amino acids.

In embodiments, there is provided the engineered N-terminal region of Asp225

```
                              (SEQ ID NO: 31)
IVGVGGSKRGAGSGARAL-Glu244
```

(underling showing the change KQWS→GSKRGAGS; SEQ ID NO: 32).

Figure 16:
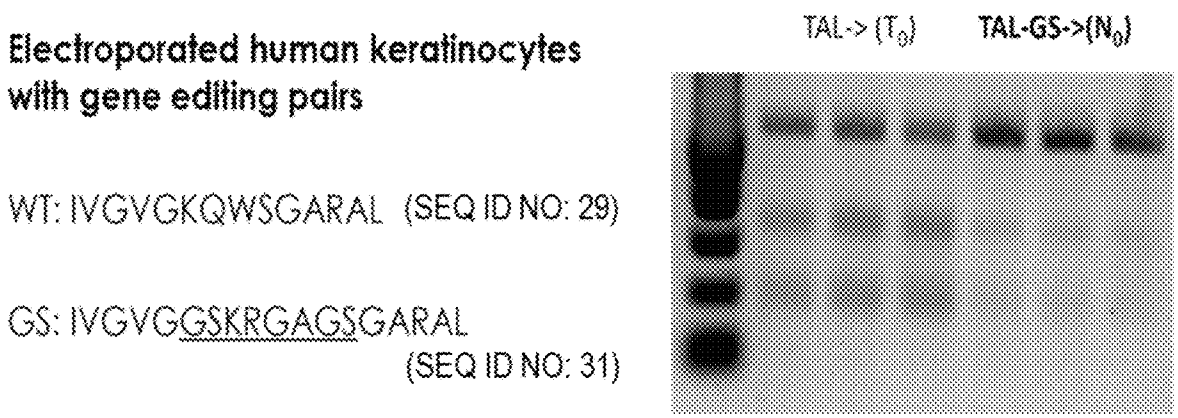
FIG. 16 shows TALEN cutting with engineered $T_0$ constraint removal.

In embodiments, the engineered gene-editing protein comprises the sequence of FIG. 16.

Gene Editing Methods

Certain embodiments are directed to a composition for altering the DNA sequence of a cell comprising a nucleic acid, wherein the nucleic acid encodes a gene-editing protein. Other embodiments are directed to a composition for altering the DNA sequence of a cell comprising a nucleic-acid mixture, wherein the nucleic-acid mixture comprises: a first nucleic acid that encodes a first gene-editing protein, and a second nucleic acid that encodes a second gene-editing protein. In one embodiment, the binding site of the first gene-editing protein and the binding site of the second gene-editing protein are present in the same target DNA molecule. In another embodiment, the binding site of the first gene-editing protein and the binding site of the second gene-editing protein are separated by less than about 50 bases, or less than about 40 bases, or less than about 30 bases or less than about 20 bases, or less than about 10 bases, or between about 10 bases and about 25 bases or about 15 bases. In one embodiment, the nuclease domain of the first gene-editing protein and the nuclease domain of the second gene-editing protein are capable of forming a dimer. In another embodiment, the dimer is capable of generating a nick or double-strand break in a target DNA molecule.

In one embodiment, the composition is a therapeutic composition.

In another embodiment, the composition comprises a repair template. In a further embodiment, the repair template is a single-stranded DNA molecule or a double-stranded DNA molecule. In embodiments, the repair template is a linear DNA molecule as described herein.

Other embodiments are directed to a method for altering the DNA sequence of a cell comprising transfecting the cell with a gene-editing protein or inducing the cell to express a gene-editing protein. Still other embodiments are directed to a method for reducing the expression of a protein of interest in a cell. In one embodiment, the cell is induced to express a gene-editing protein, wherein the gene-editing protein is capable of creating a nick or a double-strand break in a target DNA molecule. In another embodiment, the nick or double-strand break results in inactivation of a gene. Still other embodiments are directed to a method for generating an inactive, reduced-activity or dominant-negative form of a protein. Still other embodiments are directed to a method for repairing one or more mutations in a cell. In one embodiment, the cell is contacted with a repair template. In another embodiment, the repair template is a DNA molecule. In a further embodiment, the repair template does not contain a binding site of the gene-editing protein. In a still further embodiment, the repair template encodes an amino-acid sequence that is encoded by a DNA sequence that comprises a binding site of the gene-editing protein.

In embodiments, the repair template is not in the form of a circular molecule, e.g. a plasmid. In embodiments, the repair template comprises a linear DNA molecule. In embodiments, the linear DNA-based repair template is end-modified.

In embodiments, the end-modification is the addition of one or more biotin groups. In embodiments, the end-modification is the addition of one or more biotin groups to the 5' end of the linear DNA. In embodiments, the DNA is optionally further modified with one or more phosphorothioate bonds.

In embodiments, the end-modification is the addition of one or more polyethylene glycol (PEG) molecules. In embodiments, the end-modification is the addition of one or more PEG molecules connected to a random single-stranded DNA sequence (e.g. of about 5-25 nucleotides, or about 5-20 nucleotides, or about 5-15 nucleotides, or about 5-10 nucleotides, or about 10-25 nucleotides, or about 15-25 nucleotides, or about 20-25 nucleotides, or about 20 nucleotides, or about 21 nucleotides, or about 22 nucleotides, or about 23 nucleotides, or about 24 nucleotides, or about 25 nucleotides). In embodiments the PEG molecules is an 18-atom hexa-ethyleneglycol spacer.

Figure 12:
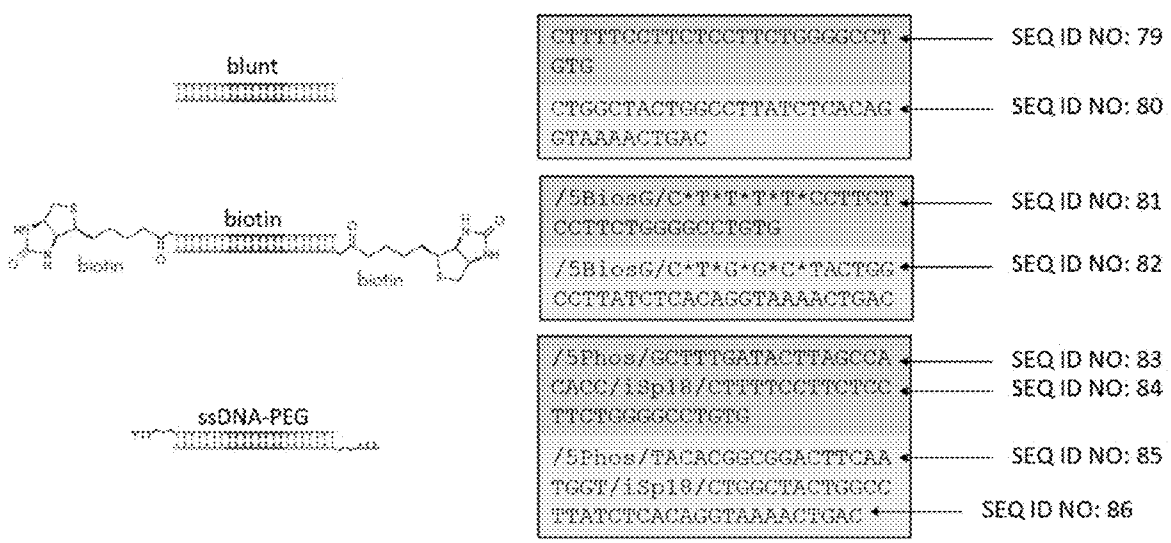
FIG. 12 shows repair template structures used in the end-modified linear DNA donor approach described herein.

In embodiments, the repair template is that of FIG. 12, or a variant thereof.

In embodiments, there is provided a method of gene-editing a cell with one or more of the gene-editing proteins described herein and one or more of the linear DNA templates described herein.

Methods of Treatment

Various aspects and embodiments relate to the treatment of a disease or disorder or compositions useful in the treatment of a disease or disorder.

In one aspect, the invention relates to a method of treating a disease or disorder comprising (a) contacting a cell or tissue with one or more cooling elements to locally reduce temperature; and (b) administering a nucleic acid encoding a gene-editing protein, the gene-editing protein comprising: (i) a DNA-binding domain comprising a plurality of repeat sequences and at least one of the repeat sequences comprises a repeat variable di-residue (RVD) at residue 12 or 13 which targets the DNA-binding domain to a target DNA molecule; and (ii) a nuclease domain comprising a catalytic domain of a nuclease, wherein the nucleic acid molecule is a synthetic RNA molecule. In embodiments, the method further comprises administering one or more of the linear DNA templates described herein.

In embodiments, the cell or tissue is of the integumentary system. In embodiments, the cell or tissue is a skin cell. In embodiments, the skin cell is a fibroblast, a keratinocyte, a melanocyte, or an adipocyte. In some embodiments, the synthetic RNA molecule is a nucleic acid drug. In some embodiments, the nucleic acid drug may alter, modify and/or change the appearance of a member of the integumentary system of a subject such as, but not limited, to skin, hair and nails. Such alteration, modification and/or change may be in the context of treatment methods and/or therapeutic uses as described herein including, by way of non-limiting example, dermatological treatments and cosmetics procedures.

In various embodiments, the agents of the present invention are used in methods the effect the integumentary system of a human. The present compositions and methods may be used to alter a biological and/or physiological process to, for example, reduce skin sagging, increase skin thickness, increase skin volume, reduce the number of wrinkles, the length of wrinkles and/or the depth of wrinkles, increase skin tightness, firmness, tone and/or elasticity, increase skin hydration and ability to retain moisture, water flow and osmotic balance, increase the levels of skin lipids; increase the extracellular matrix and/or adhesion and communication polypeptides; increase skin energy production; utilization and conservation; improve oxygen utilization; improve skin cell life; improve skin cell immunity defense, heat shock stress response, antioxidant defense capacity to neutralize free radicals, and/or toxic defense; improve the protection and recovery from ultraviolet rays; improve skin cell communication and skin cell innervations; improve cell cohesion/adhesion; improve calcium mineral and other mineral metabolism; improve cell turnover; and improve cell circadian rhythms.

Further still, in some embodiments, the present compositions may be used in the treatment, control, or prevention of a disease, disorder and/or condition and/or may alter, modify or change the appearance of a member of the integumentary system of a subject suffering from a disease, disorder and/or condition such as, but not limited to, acne vulgaris, acne aestivalis, acne conglobata, acne cosmetic, acne fulminans, acne keloidalis nuchae, acne mechanica, acne medicamentosa, acne miliaris necrotica, acne necrotica, acne rosacea, actinic keratosis, acne vulgaris, acne aestivalis, acne conglobata, acne cosmetic, acne fulminans, acne keloidalis nuchae, acne mechanica, acne medicamentosa, acne miliaris necrotica, acne necrotica, acne rosacea, acute urticaria, allergic contact dermatitis, alopecia areata, angioedema, athlete's foot, atopic dermatitis, autoeczematization, baby acne, balding, bastomycosis, blackheads, birthmarks and other skin pigmentation problems, boils, bruises, bug bites and stings, burns, cellulitis, chiggers, chloracne, cholinergic or stress uricara, chronic urticara, cold type urticara, confluent and reticulated papillomatosis, corns, cysts, dandruff, dermatitis herpetiformis, dermatographism, dyshidrotic eczema, diaper rash, dry skin, dyshidrosis, ectodermal dysplasia such as, hyprohidrotic ectodermal dysplasia and X-linked hyprohidrotic ectodermal dysplasia, eczema, epidermaodysplasia verruciformis, erythema nodosum, excoriated acne, exercise-induced anaphylasis folliculitis, excess skin oil, folliculitis, freckles, frostbite, fungal nails, hair density, hair growth rate, halogen acne, hair loss, heat rash, hematoma, herpes simplex infections (e.g. non-genital), hidradenitis suppurativa, hives, hyperhidrosis, hyperpigmentation, hypohidrotic ectodermal dysplasia, hypopigmentation, impetigo, ingrown hair, heat type urticara, ingrown toenail, infantile acne or neonatal acne, itch, irritant contact dermatitis, jock itch, keloid, keratosis pilaris, lichen planus, lichen sclerosus, lupus miliaris disseminatus faciei, melasma, moles, molluscum contagiosum, nail growth rate, nail health, neurodermatitis, nummular eczema, occupational acne, oil acne, onychomycosis, physical urticara, pilonidal cyst, *Pityriasis rosea, Pityriasis versicolor*, poison ivy, pomade acne, pseudofolliculitis barbae or acne keloidalis nuchae, psoriasis, psoriatic arthritis, pressure or delayed pressue urticara, puncture wounds such as cuts and scrapes, rash, rare or water type urticara, rhinoplasty, ringworm, rosacea, rothmund-thomson syndrome, sagging of the skin, scabis, scars, seborrhea, seborrheic dermatitis, shingles, skin cancer, skin tag, solar type urticara, spider bite, stretch marks, sunburn, tar acne, tropical acne, thinning of skin, thrush, tinea versicolor, transient acantholytic dermatosis, tycoon's cap or acne necrotica miliaris, uneven skin tone, varicose veins, venous eczema, vibratory angioedema, vitiligo, warts, Weber-Christian disease, wrinkles, x-linked hypohidrotic ectodermal dysplasia, xerotic eczema, yeast infection and general signs of aging.

Other embodiments are directed to a method for delivering a nucleic acid to a cell in vivo comprising applying a nucleic acid to a tissue containing a cell in vivo. In one embodiment, the method further comprises applying a transient electric field in the vicinity of the cell. In another embodiment, the method results in the cell in vivo internalizing the nucleic acid. In yet another embodiment, the nucleic acid comprises synthetic RNA. In a further embodiment, the method further results in the cell internalizing a therapeutically or cosmetically effective amount of the nucleic acid. In one embodiment, the cell is a skin cell. In another embodiment, the cell is a muscle cell. In yet another embodiment, the cell is a dermal fibroblast. In a further embodiment, the cell is a keratinocyte. In a still further embodiment, the cell is a myoblast. In some embodiments, the nucleic acid comprises a protein of interest. In one embodiment, the protein of interest is a fluorescent protein. In another embodiment, the protein of interest is an extracellular-matrix protein. In yet another embodiment, the protein of interest is a member of the group: elastin, collagen, laminin, fibronectin, vitronectin, lysyl oxidase, elastin binding protein, a growth factor, fibroblast growth factor, transforming growth factor beta, granulocyte colony-stimulating factor, a matrix metalloproteinase, an actin, fibrillin, microfibril-associated glycoprotein, a lysyl-oxidase-like protein, platelet-derived growth factor, a lipase, an uncoupling protein, thermogenin, filaggrin, a fibroblast growth factor, an antibody, and a protein involved with pigment production. In some embodiments, the method further comprises delivering the nucleic acid to the epidermis. In other embodiments, the method further comprises delivering the nucleic acid to the dermis. In still other embodiments, the method further comprises delivering the nucleic acid below the dermis. In one embodiment, the delivering is by injection. In another embodiment, the delivering is by injection using a micro-needle array. In yet another embodiment, the delivering is by topical administration. In a further embodiment, the delivering comprises disruption or removal of a part of the tissue. In a still further embodiment, the delivering comprises disruption or removal of the stratum corneum. In some embodiments, the nucleic acid is present in solution. In one embodiment, the solution comprises a growth factor. In another embodiment, the growth factor is a member of the group: a fibroblast growth factor and a transforming growth factor. In yet another embodiment, the growth factor is a member of the group: basis fibroblast growth factor and transforming growth factor beta. In other embodiments, the solution comprises cholesterol.

In another embodiment, the method further comprises contacting the cell with one or more nucleic acid molecules. In yet another embodiment, at least one of the one or more nucleic acid molecules encodes a protein of interest. In a further embodiment, the method results in the cell expressing the protein of interest. In a still further embodiment, the method results in the cell expressing a therapeutically or cosmetically effective amount of the protein of interest.

In another embodiment, the cell is contacted with a nucleic acid molecule. In yet another embodiment, the method results in the cell internalizing the nucleic acid molecule. In a further embodiment, the method results in the cell internalizing a therapeutically or cosmetically effective amount of the nucleic acid molecule. In one embodiment, the nucleic acid encodes a protein of interest. In one embodiment, the nucleic acid molecule comprises a member of the group: a dsDNA molecule, a ssDNA molecule, a RNA molecule, a dsRNA molecule, a ssRNA molecule, a plasmid, an oligonucleotide, a synthetic RNA molecule, a miRNA molecule, an mRNA molecule, and an siRNA molecule. In various embodiments, the RNA comprises one or more non-canonical nucleotides.

In some embodiments, the present invention relates to one or more administration techniques described in U.S. Pat. Nos. 5,711,964; 5,891,468; 6,316,260; 6,413,544; 6,770,291; and 7,390,780, the entire contents of which are hereby incorporated by reference in their entireties.

In another aspect, the invention relates to a method of treating a disease or disorder comprising (a) providing a nucleic acid encoding a gene-editing protein, the gene-editing protein comprising: (i) a DNA-binding domain comprising a plurality of repeat sequences and at least one of the repeat sequences comprises a repeat variable di-residue (RVD) at residue 12 or 13 which targets the DNA-binding domain to a target DNA molecule; and (ii) a nuclease domain comprising a catalytic domain of a nuclease, wherein the nucleic acid molecule is a synthetic RNA molecule; (b) transfecting the cell with the one or more synthetic RNA molecules to yield a nick or double-strand break in a target DNA molecule in the cell, wherein the transfecting occurs at about 30° C. to about 35° C. (e.g., without limitation, about 33° C.); and (c) administering the transfected cell to a subject in need thereof.

In embodiments, the catalytic domain is from FokI, StsI, or a hybrid thereof.

In embodiments, the nuclease domain is capable of forming a dimer with another nuclease domain.

In embodiments, the gene-editing protein is capable of generating a nick or double-strand break in a target DNA molecule.

In embodiments, the RVD recognizes one base pair in the nucleic acid molecule. In embodiments, the RVD recognizes a C residue in the nucleic acid molecule and is selected from HD, N(null), HA, ND, and HI. In embodiments, the RVD recognizes a G residue in the nucleic acid molecule and is selected from NN, NH, NK, HN, and NA. In embodiments, the RVD recognizes an A residue in the nucleic acid molecule and is selected from NI and NS. In embodiments, the RVD recognizes a T residue in the nucleic acid molecule and is selected from NG, HG, H(null), and IG.

In some embodiments, the RVD recognizing a C residue in the nucleic acid molecule is HD. In some embodiments, the RVD recognizing a C residue in the nucleic acid molecule is N(null). In some embodiments, the RVD recognizing a C residue in the nucleic acid molecule is HA. In some embodiments, the RVD recognizing a C residue in the nucleic acid molecule is ND. In some embodiments, the RVD recognizing a C residue in the nucleic acid molecule is HI. In some embodiments, the RVD recognizing a G residue in the nucleic acid molecule is NN. In some embodiments, the RVD recognizing a G residue in the nucleic acid molecule is NH. In some embodiments, the RVD recognizing a G residue in the nucleic acid molecule is NK. In some embodiments, the RVD recognizing a G residue in the nucleic acid molecule is HN. In some embodiments, the RVD recognizing a G residue in the nucleic acid molecule is NA. In some embodiments, the RVD recognizing an A residue in the nucleic acid molecule is NI. In some embodiments, the RVD recognizing an A residue in the nucleic acid molecule is NS. In some embodiments, the RVD recognizing a T residue in the nucleic acid molecule is NG. In some embodiments, the RVD recognizing a T residue in the nucleic acid molecule is HG. In some embodiments, the RVD recognizing a T residue in the nucleic acid molecule is H(null). In some embodiments, the RVD recognizing a T residue in the nucleic acid molecule is IG.

In embodiments, the repeat sequence is 33 or 34 amino acids long. In embodiments, the repeat sequence is 36-39 amino acids long. In some embodiments, the repeat sequence is 36 amino acids long. In some embodiments, the repeat sequence is 37 amino acids long. In some embodiments, the repeat sequence is 38 amino acids long. In some embodiments, the repeat sequence is 39 amino acids long.

In embodiments, the DNA-binding domain comprises a plurality of repeat sequences and at least one of the repeat sequences comprises the amino acid sequence: LTPvQVVAIAwxyz (SEQ ID NO: 12), wherein: v is Q, D or E, w is S or N, x is I, H, N, or I, y is D, A, I, N, H, K, S, G or null, and z is GGRPALE (SEQ ID NO: 1), GGKQALE (SEQ ID NO: 2), GGKQALETVQRLLPVLCQDHG (SEQ ID NO: 3), GGKQALETVQRLLPVLCQAHG (SEQ ID NO: 4), GKQALETVQRLLPVLCQDHG (SEQ ID NO: 5), GKQALETVQRLLPVLCQAHG (SEQ ID NO: 6), GGKQALETVQRLLPVLCQD (SEQ ID NO: 7) or GGKQALETVQRLLPVLCQA (SEQ ID NO: 8).

In embodiments, at least one of the repeat sequences comprises the amino acid sequence: LTPvQVVAIAwxyz$\alpha$ (SEQ ID NO: 11), wherein: v is Q, D or E, w is S or N, x is I, H, N, or I, y is D, A, I, N, H, K, S, G or null, z is GGRPALE (SEQ ID NO: 1), GGKQALE (SEQ ID NO: 2), GGKQALETVQRLLPVLCQDHG (SEQ ID NO: 3), GGKQALETVQRLLPVLCQAHG (SEQ ID NO: 4), GKQALETVQRLLPVLCQDHG (SEQ ID NO: 5), GKQALETVQRLLPVLCQAHG (SEQ ID NO: 6), GGKQALETVQRLLPVLCQD (SEQ ID NO: 7) or GGKQALETVQRLLPVLCQA (SEQ ID NO: 8), and $\alpha$ is any four consecutive amino acids.

In some embodiments, z is GGRPALE (SEQ ID NO: 1) and $\alpha$ is null. In some embodiments, z is GGKQALE (SEQ ID NO: 2) and $\alpha$ is null. In some embodiments, z is GGKQALETVQRLLPVLCQDHG (SEQ ID NO: 3) and $\alpha$ is null. In some embodiments, z is GGKQALETVQRLLPVLCQAHG (SEQ ID NO: 4) and $\alpha$ is null. In some embodiments, z is GKQALETVQRLLPVLCQDHG (SEQ ID NO: 5) and $\alpha$ is null. In some embodiments, z is GKQALETVQRLLPVLCQAHG (SEQ ID NO: 6) and $\alpha$ is null. In some embodiments, z is GGKQALETVQRLLPVLCQD (SEQ ID NO: 7) and $\alpha$ is null. In some embodiments, z is GGKQALETVQRLLPVLCQA (SEQ ID NO: 8) and $\alpha$ is null.

In some embodiments, z is GGRPALE (SEQ ID NO: 1). In some embodiments, z is GGKQALE (SEQ ID NO: 2). In some embodiments, z is GGKQALETVQRLLPVLCQDHG (SEQ ID NO: 3). In some embodiments, z is GGKQALETVQRLLPVLCQAHG (SEQ ID NO: 4). In some embodiments, z is GKQALETVQRLLPVLCQDHG (SEQ ID NO: 5). In some embodiments, z is GKQALETVQRLLPVLCQAHG (SEQ ID NO: 6). In some embodiments, z is GGKQALETVQRLLPVLCQD (SEQ ID NO: 7). In some embodiments, z is GGKQALETVQRLLPVLCQA (SEQ ID NO: 8).

In embodiments, a comprises at least one glycine (G) residue. In embodiments, a comprises at least one histidine (H) residue. In embodiments, a comprises at least one histidine (H) residue at any one of positions 33, 34, or 35. In embodiments, a comprises at least one aspartic acid (D) residue. In embodiments, a comprises at least one, or two, or three of a glycine (G) residue, a histidine (H) residue, and an aspartic acid (D) residue.

In embodiments, a comprises one or more hydrophilic residues, optionally selected from: a polar and positively charged hydrophilic amino acid, optionally selected from arginine (R) and lysine (K); a polar and neutral of charge hydrophilic amino acid, optionally selected from asparagine (N), glutamine (Q), serine (S), threonine (T), proline (P), and cysteine (C); a polar and negatively charged hydrophilic amino acid, optionally selected from aspartate (D) and glutamate (E), and an aromatic, polar and positively charged hydrophilic amino acid, optionally selected from histidine (H).

In some embodiments, a comprises one or more polar and positively charged hydrophilic amino acids selected from arginine (R) and lysine (K). In some embodiments, a comprises one or more polar and neutral of charge hydrophilic amino acids selected from asparagine (N), glutamine (Q), serine (S), threonine (T), proline (P), and cysteine (C). In some embodiments, a comprises one or more polar and negatively charged hydrophilic amino acids selected from aspartate (D) and glutamate (E). In some embodiments, a comprises one or more aromatic, polar and positively charged hydrophilic amino acids selected from histidine (H).

In embodiments, a comprises one or more hydrophobic residues, optionally selected from: a hydrophobic, aliphatic amino acid, optionally selected from glycine (G), alanine (A), leucine (L), isoleucine (I), methionine (M), and valine (V), and a hydrophobic, aromatic amino acid, optionally selected from phenylalanine (F), tryptophan (W), and tyrosine (Y).

In some embodiments, a comprises one or more hydrophobic, aliphatic amino acids selected from glycine (G), alanine (A), leucine (L), isoleucine (I), methionine (M), and valine (V). In some embodiments, a comprises one or more aromatic amino acids selected from phenylalanine (F), tryptophan (W), and tyrosine (Y).

In embodiments, $\alpha$ is selected from GHGG (SEQ ID NO: 38), HGSG (SEQ ID NO: 39), HGGG (SEQ ID NO: 40), GGHD (SEQ ID NO: 41), GAHD (SEQ ID NO: 42), AHDG (SEQ ID NO: 43), PHDG (SEQ ID NO: 44), GPHD (SEQ ID NO: 45), GHGP (SEQ ID NO: 46), PHGG (SEQ ID NO: 47), PHGP (SEQ ID NO: 48), AHGA (SEQ ID NO: 49), LHGA (SEQ ID NO: 50), VHGA (SEQ ID NO: 51), IVHG (SEQ ID NO: 52), IHGM (SEQ ID NO: 53), RHGD (SEQ ID NO: 54), RDHG (SEQ ID NO: 55), RHGE (SEQ ID NO: 56), HRGE (SEQ ID NO: 57), HRGD (SEQ ID NO: 58), GPYE (SEQ ID NO: 59), NHGG (SEQ ID NO: 60), THGG (SEQ ID NO: 61), GTHG (SEQ ID NO: 62), GSGS (SEQ ID NO: 63), GSGG (SEQ ID NO: 64), GGGG (SEQ ID NO: 65), GRGG (SEQ ID NO: 66), and GKGG (SEQ ID NO: 67).

In embodiments, the nucleic acid is a synthetic RNA molecule. In embodiments, the synthetic RNA molecule is mRNA.

In embodiments, the DNA-binding domain comprises about 15, or about, 16, or about 17, or about 18, or about 18.5 repeat sequences.

Further, some aspects of the methods described herein find use in various medical treatments, including, by way of illustration, treating a disease, disorder and/or condition of the integumentary system or altering, modifying and/or changing the integumentary system (e.g. cosmetically).

In one aspect, the invention provides methods and compositions for treating diseases and conditions in humans, including, but not limited to, prophylactic treatments, treatments for rare diseases, including, but not limited to, dermatologic rare diseases, and treatments for use in medical dermatology and aesthetic medicine. In another aspect, the invention provides cosmetics comprising nucleic acids. Still further aspects relate to methods and compositions for altering pigmentation, for example, for the treatment of pigmentation disorders. Still further aspects relate to methods and compositions for enhancing healing, including, but not limited to, healing in response to a wound or surgery.

In various embodiments, a variety of cancers are treated, controlled or prevented with the present compositions (e.g., colorectal cancer, gallbladder cancer, lung cancer, pancreatic cancer, and stomach cancer). In some embodiments, skin cancer is treated with the present compositions. For instance, the skin cancer is one or more of actinic keratosis, basal cell carcinoma, melanoma, Kaposi's sarcoma, and squamous cell carcinoma. In some embodiments, the present compositions are used adjuvant to complete circumferential peripheral and deep margin assessment, Mohs surgery, radiation (e.g. external beam radiotherapy or brachytherapy), chemotherapy (including but not limited to topical chemotherapy, e.g. with imiquimod or 5-fluorouracil), and cryotherapy. The present compositions also find use in the treatment of various stages of cancers, including skin cancers (e.g. basal cell cancer (BCC), squamous cell cancer (SCC), and melanoma), such as a stage of the American Joint Committee on Cancer (AJCC) TNM system (e.g. one or more of TX, T0, Tis, T1, T1a, T1b, T2, T2A, T2B, T3, T3a, T3b, T4, T4a, T4b, NX, N0, N1, N2, N3, M0, M1a, M1b, M1c) and/or a staging system (e.g. Stage 0, Stage IA, Stage IB, Stage IIA, Stage IIB, Stage IIC, Stage IIIA, Stage IIIB, Stage IIIC, Stage IV).

Illustrative cancers and/or tumors of the present invention include, but are not limited to, a basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (such as that associated with brain tumors), and Meigs' syndrome.

In various embodiments, one or more rare diseases are treated, controlled or prevented with the present compositions, including, by way of illustration, Erythropoietic Protoporphyria, Hailey-Hailey Disease, Epidermolysis Bullosa (EB), Xeroderma Pigmentosum, Ehlers-Danlos Syndrome, Cutis Laxa, Protein C & Protein S Deficiency, Alport Syndrome, Striate Palmoplantar Keratoderma, Lethal Acantholytic EB, Pseudoxanthoma Elasticum (PXE), Ichthyosis Vulgaris, Pemphigus Vulgaris, and Basal Cell Nevus Syndrome.

In various embodiments, the present compositions are used to treat, control or prevent one or more inflammatory diseases or conditions, such as inflammation, acute inflammation, chronic inflammation, respiratory disease, atherosclerosis, restenosis, asthma, allergic rhinitis, atopic dermatitis, septic shock, rheumatoid arthritis, inflammatory bowel disease, inflammatory pelvic disease, pain, ocular inflammatory disease, celiac disease, Leigh Syndrome, Glycerol Kinase Deficiency, Familial eosinophilia (FE), autosomal recessive spastic ataxia, laryngeal inflammatory disease; Tuberculosis, Chronic cholecystitis, Bronchiectasis, Silicosis and other pneumoconioses.

In various embodiments, the present compositions are used to treat, control or prevent one or more autoimmune diseases or conditions, such as multiple sclerosis, diabetes mellitus, lupus, celiac disease, Crohn's disease, ulcerative colitis, Guillain-Barre syndrome, scleroderms, Goodpasture's syndrome, Wegener's granulomatosis, autoimmune epilepsy, Rasmussen's encephalitis, Primary biliary sclerosis, Sclerosing cholangitis, Autoimmune hepatitis, Addison's disease, Hashimoto's thyroiditis, Fibromyalgia, Menier's syndrome; transplantation rejection (e.g., prevention of allograft rejection) pernicious anemia, rheumatoid arthritis, systemic lupus erythematosus, dermatomyositis, Sjogren's syndrome, lupus erythematosus, multiple sclerosis, myasthenia gravis, Reiter's syndrome, Grave's disease, and other autoimmune diseases.

In various embodiments, the present compositions are used to treat, control or prevent one or more neurologic diseases, including ADHD, AIDS-Neurological Complications, Absence of the Septum Pellucidum, Acquired Epileptiform Aphasia, Acute Disseminated Encephalomyelitis, Adrenoleukodystrophy, Agenesis of the Corpus Callosum, Agnosia, Aicardi Syndrome, Alexander Disease, Alpers' Disease, Alternating Hemiplegia, Alzheimer's Disease, Amyotrophic Lateral Sclerosis, Anencephaly, Aneurysm, Angelman Syndrome, Angiomatosis, Anoxia, Aphasia, Apraxia, Arachnoid Cysts, Arachnoiditis, Arnold-Chiari Malformation, Arteriovenous Malformation, Aspartame, Asperger Syndrome, Ataxia Telangiectasia, Ataxia, Attention Deficit-Hyperactivity Disorder, Autism, Autonomic Dysfunction, Back Pain, Barth Syndrome, Batten Disease, Behcet's Disease, Bell's Palsy, Benign Essential Blepharospasm, Benign Focal Amyotrophy, Benign Intracranial Hypertension, Bernhardt-Roth Syndrome, Binswanger's Disease, Blepharospasm, Bloch-Sulzberger Syndrome, Brachial Plexus Birth Injuries, Brachial Plexus Injuries, Bradbury-Eggleston Syndrome, Brain Aneurysm, Brain Injury, Brain and Spinal Tumors, Brown-Sequard Syndrome, Bulbospinal Muscular Atrophy, Canavan Disease, Carpal Tunnel Syndrome, Causalgia, Cavernomas, Cavernous Angioma, Cavernous Malformation, Central Cervical Cord Syndrome, Central Cord Syndrome, Central Pain Syndrome, Cephalic Disorders, Cerebellar Degeneration, Cerebellar Hypoplasia, Cerebral Aneurysm, Cerebral Arteriosclerosis, Cerebral Atrophy, Cerebral Beriberi, Cerebral Gigantism, Cerebral Hypoxia, Cerebral Palsy, Cerebro-Oculo-Facio-Skeletal Syndrome, Charcot-Marie-Tooth Disorder, Chiari Malformation, Chorea, Choreoacanthocytosis, Chronic Inflammatory Demyelinating Polyneuropathy (CIDP), Chronic Orthostatic Intolerance, Chronic Pain, Cockayne Syndrome Type II, Coffin Lowry Syndrome, Coma, including Persistent Vegetative State, Complex Regional Pain Syndrome, Congenital Facial Diplegia, Congenital Myasthenia, Congenital Myopathy, Congenital Vascular Cavernous Malformations, Corticobasal Degeneration, Cranial Arteritis, Craniosynostosis, Creutzfeldt-Jakob Disease, Cumulative Trauma Disorders, Cushing's Syndrome, Cytomegalic Inclusion Body Disease (CIBD), Cytomegalovirus Infection, Dancing Eyes-Dancing Feet Syndrome, Dandy-Walker Syndrome, Dawson Disease, De Morsier's Syndrome, Dejerine-Klumpke Palsy, Dementia-Multi-Infarct, Dementia-Subcortical, Dementia With Lewy Bodies, Dermatomyositis, Developmental Dyspraxia, Devic's Syndrome, Diabetic Neuropathy, Diffuse Sclerosis, Dravet's Syndrome, Dysautonomia, Dysgraphia, Dyslexia, Dysphagia, Dyspraxia, Dystonias, Early Infantile Epileptic Encephalopathy, Empty Sella Syndrome, Encephalitis Lethargica, Encephalitis and Meningitis, Encephaloceles, Encephalopathy, Encephalotrigeminal Angiomatosis, Epilepsy, Erb's Palsy, Erb-Duchenne and Dejerine-Klumpke Palsies, Fabry's Disease, Fahr's Syndrome, Fainting, Familial Dysautonomia, Familial Hemangioma, Familial Idiopathic Basal Ganglia Calcification, Familial Spastic Paralysis, Febrile Seizures (e.g., GEFS and GEFS plus), Fisher Syndrome, Floppy Infant Syndrome, Friedreich's Ataxia, Gaucher's Disease, Gerstmann's Syndrome, Gerstmann-Straussler-Scheinker Disease, Giant Cell Arteritis, Giant Cell Inclusion Disease, Globoid Cell Leukodystrophy, Glossopharyngeal Neuralgia, Guillain-Barre Syndrome, HTLV-1 Associated Myelopathy, Hallervorden-Spatz Disease, Head Injury, Headache, Hemicrania Continua, Hemifacial Spasm, Hemiplegia Alterans, Hereditary Neuropathies, Hereditary Spastic Paraplegia, Heredopathia Atactica Polyneuritiformis, Herpes Zoster Oticus, Herpes Zoster, Hirayama Syndrome, Holoprosencephaly, Huntington's Disease, Hydranencephaly, Hydrocephalus-Normal Pressure, Hydrocephalus, Hydromyelia, Hypercortisolism, Hypersomnia, Hypertonia, Hypotonia, Hypoxia, Immune-Mediated Encephalomyelitis, Inclusion Body Myositis, Incontinentia Pigmenti, Infantile Hypotonia, Infantile Phytanic Acid Storage Disease, Infantile Refsum Disease, Infantile Spasms, Inflammatory Myopathy, Intestinal Lipodystrophy, Intracranial Cysts, Intracranial Hypertension, Isaac's Syndrome, Joubert Syndrome, Kearns-Sayre Syndrome, Kennedy's Disease, Kinsbourne syndrome, Kleine-Levin syndrome, Klippel Feil Syndrome, Klippel-Trenaunay Syndrome (KTS), Klüver-Bucy Syndrome, Korsakoffs Amnesic Syndrome, Krabbe Disease, Kugelberg-Welander Disease, Kuru, Lambert-Eaton Myasthenic Syndrome, Landau-Kleffner Syndrome, Lateral Femoral Cutaneous Nerve Entrapment, Lateral Medullary Syndrome, Learning Disabilities, Leigh's Disease, Lennox-Gastaut Syndrome, Lesch-Nyhan Syndrome, Leukodystrophy, Levine-Critchley Syndrome, Lewy Body Dementia, Lissencephaly, Locked-In Syndrome, Lou Gehrig's Disease, Lupus-Neurological Sequelae, Lyme Disease-Neurological Complications, Machado-Joseph Disease, Macrencephaly, Megalencephaly, Melkersson-Rosenthal Syndrome, Meningitis, Menkes Disease, Meralgia Paresthetica, Metachromatic Leukodystrophy, Microcephaly, Migraine, Miller Fisher Syndrome, Mini-Strokes, Mitochondrial Myopathies, Mobius Syndrome, Monomelic Amyotrophy, Motor Neuron Diseases, Moyamoya Disease, Mucolipidoses, Mucopolysaccharidoses, Multi-Infarct Dementia, Multifocal Motor Neuropathy, Multiple Sclerosis, Multiple System Atrophy with Orthostatic Hypotension, Multiple System Atrophy, Muscular Dystrophy, Myasthenia-Congenital, Myasthenia Gravis, Myelinoclastic Diffuse Sclerosis, Myoclonic Encephalopathy of Infants, Myoclonus, Myopathy-Congenital, Myopathy-Thyrotoxic, Myopathy, Myotonia Congenita, Myotonia, Narcolepsy, Neuroacanthocytosis, Neurodegeneration with Brain Iron Accumulation, Neurofibromatosis, Neuroleptic Malignant Syndrome, Neurological Complications of AIDS, Neurological Manifestations of Pompe Disease, Neuromyelitis Optica, Neuromyotonia, Neuronal Ceroid Lipofuscinosis, Neuronal Migration Disorders, Neuropathy-Hereditary, Neurosarcoidosis, Neurotoxicity, Nevus Cavernosus, Niemann-Pick Disease, O'Sullivan-McLeod Syndrome, Occipital Neuralgia, Occult Spinal Dysraphism Sequence, Ohtahara Syndrome, Olivopontocerebellar Atrophy, Opsoclonus Myoclonus, Orthostatic Hypotension, Overuse Syndrome, Pain—Chronic, Paraneoplastic Syndromes, Paresthesia, Parkinson's Disease, Parnyotonia Congenita, Paroxysmal Choreoathetosis, Paroxysmal Hemicrania, Parry-Romberg, Pelizaeus-Merzbacher Disease, Pena Shokeir II Syndrome, Perineural Cysts, Periodic Paralyses, Peripheral Neuropathy, Periventricular Leukomalacia, Persistent Vegetative State, Pervasive Developmental Disorders, Phytanic Acid Storage Disease, Pick's Disease, Piriformis Syndrome, Pituitary Tumors, Polymyositis, Pompe Disease, Porencephaly, Post-Polio Syndrome, Postherpetic Neuralgia, Postinfectious Encephalomyelitis, Postural Hypotension, Postural Orthostatic Tachycardia Syndrome, Postural Tachycardia Syndrome, Primary Lateral Sclerosis, Prion Diseases, Progressive Hemifacial Atrophy, Progressive Locomotor Ataxia, Progressive Multifocal Leukoencephalopathy, Progressive Sclerosing Poliodystrophy, Progressive Supranuclear Palsy, Pseudotumor Cerebri, Pyridoxine Dependent and Pyridoxine Responsive Siezure Disorders, Ramsay Hunt Syndrome Type I, Ramsay Hunt Syndrome Type II, Rasmussen's Encephalitis and other autoimmune epilepsies, Reflex Sympathetic Dystrophy Syndrome, Refsum Disease—Infantile, Refsum Disease, Repetitive Motion Disorders, Repetitive Stress Injuries, Restless Legs Syndrome, Retrovirus-Associated Myelopathy, Rett Syndrome, Reye's Syndrome, Riley-Day Syndrome, SUNCT Headache, Sacral Nerve Root Cysts, Saint Vitus Dance, Salivary Gland Disease, Sandhoff Disease, Schilder's Disease, Schizencephaly, Seizure Disorders, Septo-Optic Dysplasia, Severe Myoclonic Epilepsy of Infancy (SMEI), Shaken Baby Syndrome, Shingles, Shy-Drager Syndrome, Sjogren's Syndrome, Sleep Apnea, Sleeping Sickness, Soto's Syndrome, Spasticity, Spina Bifida, Spinal Cord Infarction, Spinal Cord Injury, Spinal Cord Tumors, Spinal Muscular Atrophy, Spinocerebellar Atrophy, Steele-Richardson-Olszewski Syndrome, Stiff-Person Syndrome, Striatonigral Degeneration, Stroke, Sturge-Weber Syndrome, Subacute Sclerosing Panencephalitis, Subcortical Arteriosclerotic Encephalopathy, Swallowing Disorders, Sydenham Chorea, Syncope, Syphilitic Spinal Sclerosis, Syringohydromyelia, Syringomyelia, Systemic Lupus Erythematosus, Tabes Dorsalis, Tardive Dyskinesia, Tarlov Cysts, Tay-Sachs Disease, Temporal Arteritis, Tethered Spinal Cord Syndrome, Thomsen Disease, Thoracic Outlet Syndrome, Thyrotoxic Myopathy, Tic Douloureux, Todd's Paralysis, Tourette Syndrome, Transient Ischemic Attack, Transmissible Spongiform Encephalopathies, Transverse Myelitis, Traumatic Brain Injury, Tremor, Trigeminal Neuralgia, Tropical Spastic Paraparesis, Tuberous Sclerosis, Vascular Erectile Tumor, Vasculitis including Temporal Arteritis, Von Economo's Disease, Von Hippel-Lindau disease (VHL), Von Recklinghausen's Disease, Wallenberg's Syndrome, Werdnig-Hoffman Disease, Wernicke-Korsakoff Syndrome, West Syndrome, Whipple's Disease, Williams Syndrome, Wilson's Disease, X-Linked Spinal and Bulbar Muscular Atrophy, and Zellweger Syndrome.

In various embodiments, the present compositions are used to treat one or more respiratory diseases, such as asthma, chronic obstructive pulmonary disease (COPD), bronchiectasis, allergic rhinitis, sinusitis, pulmonary vasoconstriction, inflammation, allergies, impeded respiration, respiratory distress syndrome, cystic fibrosis, pulmonary hypertension, pulmonary vasoconstriction, emphysema, Hantavirus pulmonary syndrome (HPS), Loeffler's syndrome, Goodpasture's syndrome, Pleurisy, pneumonitis, pulmonary edema, pulmonary fibrosis, Sarcoidosis, complications associated with respiratory syncitial virus infection, and other respiratory diseases.

In various embodiments, the present compositions are used to treat, control or prevent cardiovascular disease, such as a disease or condition affecting the heart and vasculature, including but not limited to, coronary heart disease (CHD), cerebrovascular disease (CVD), aortic stenosis, peripheral vascular disease, atherosclerosis, arteriosclerosis, myocardial infarction (heart attack), cerebrovascular diseases (stroke), transient ischaemic attacks (TIA), angina (stable and unstable), atrial fibrillation, arrhythmia, vavular disease, and/or congestive heart failure.

In various embodiments, the present compositions are used to treat, control or prevent one or more metabolic-related disorders. In various embodiments, the present invention is useful for the treatment, controlling or prevention of diabetes, including Type 1 and Type 2 diabetes and diabetes associated with obesity. The compositions and methods of the present invention are useful for the treatment or prevention of diabetes-related disorders, including without limitation diabetic nephropathy, hyperglycemia, impaired glucose tolerance, insulin resistance, obesity, lipid disorders, dyslipidemia, hyperlipidemia, hypertriglyceridemia, hypercholesterolemia, low HDL levels, high LDL levels, atherosclerosis and its sequelae, vascular restenosis, irritable bowel syndrome, inflammatory bowel disease, including Crohn's disease and ulcerative colitis, other inflammatory conditions, pancreatitis, abdominal obesity, neurodegenerative disease, retinopathy, neoplastic conditions, adipose cell tumors, adipose cell carcinomas, such as liposarcoma, prostate cancer and other cancers, including gastric, breast, bladder and colon cancers, angiogenesis, Alzheimer's disease, psoriasis, high blood pressure, Metabolic Syndrome (e.g. a person has three or more of the following disorders: abdominal obesity, hypertriglyceridemia, low HDL cholesterol, high blood pressure, and high fasting plasma glucose), ovarian hyperandrogenism (polycystic ovary syndrome), and other disorders where insulin resistance is a component, such as sleep apnea. The compositions and methods of the present invention are useful for the treatment, control, or prevention of obesity, including genetic or environmental, and obesity-related disorders. The obesity-related disorders herein are associated with, caused by, or result from obesity. Examples of obesity-related disorders include obesity, diabetes, overeating, binge eating, and bulimia, hypertension, elevated plasma insulin concentrations and insulin resistance, dyslipidemia, hyperlipidemia, endometrial, breast, prostate, kidney and colon cancer, osteoarthritis, obstructive sleep apnea, gallstones, heart disease, abnormal heart rhythms and arrythmias, myocardial infarction, congestive heart failure, coronary heart disease, sudden death, stroke, polycystic ovary disease, craniopharyngioma, Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia. Further examples of obesity-related disorders are Metabolic Syndrome, insulin resistance syndrome, reproductive hormone abnormalities, sexual and reproductive dysfunction, such as impaired fertility, infertility, hypogonadism in males and hirsutism in females, fetal defects associated with maternal obesity, gastrointestinal motility disorders, such as obesity-related gastro-esophageal reflux, respiratory disorders, such as obesity-hypoventilation syndrome (Pickwickian syndrome), breathlessness, cardiovascular disorders, inflammation, such as systemic inflammation of the vasculature, arteriosclerosis, hypercholesterolemia, lower back pain, gallbladder disease, hyperuricemia, gout, and kidney cancer, and increased anesthetic risk. The compositions and methods of the present invention are also useful to treat Alzheimer's disease.

Nucleic acids, including liposomal formulations containing nucleic acids, when delivered in vivo, can accumulate in the liver and/or spleen. It has now been discovered that nucleic acids encoding proteins can modulate protein expression in the liver and spleen, and that nucleic acids used in this manner can constitute potent therapeutics for the treatment of liver and spleen diseases. Certain embodiments are therefore directed to a method for treating liver and/or spleen disease by delivering to a patient a nucleic acid encoding a protein of interest. Other embodiments are directed to a therapeutic composition comprising a nucleic acid encoding a protein of interest, for the treatment of liver and/or spleen disease. Diseases and conditions of the liver and/or spleen that can be treated include, but are not limited to: hepatitis, alcohol-induced liver disease, drug-induced liver disease, Epstein Barr virus infection, adenovirus infection, cytomegalovirus infection, toxoplasmosis, Rocky Mountain spotted fever, non-alcoholic fatty liver disease, hemochromatosis, Wilson's Disease, Gilbert's Disease, and cancer of the liver and/or spleen.

In some embodiments, the present compositions and methods relate to the treatment of type 1 diabetes, heart disease, including ischemic and dilated cardiomyopathy, macular degeneration, Parkinson's disease, cystic fibrosis, sickle-cell anemia, thalassemia, Fanconi anemia, severe combined immunodeficiency, hereditary sensory neuropathy, xeroderma pigmentosum, Huntington's disease, muscular dystrophy, amyotrophic lateral sclerosis, Alzheimer's disease, cancer, and infectious diseases including hepatitis and HIV/AIDS.

In various embodiments, the nucleic acid drug is administered is a manner that it effects one or more of keratinocytes and fibroblasts (e.g. causes these cells to express one or more therapeutic proteins). For example, present methods allow for methods in which a patient's cells are used to generate a therapeutic protein and the levels of such protein are tailored by synthetic RNA dosing.

In a specific embodiment, the synthetic RNA targets a soluble protein. In some embodiments, the synthetic RNA targets a protein of one or more of the following families of proteins: transforming growth factor (TGF) beta, bone morphogenetic proteins (BMPs), Fibroblast growth factors (FGFs), vascular endothelial growth factors (VEGFs), and interleukins.

In some embodiments, the nucleic acid drug is used for treatment to prevent loss of and/or increase bone mass in metabolic bone diseases. General methods for treatment to prevent loss of and/or increase bone mass in metabolic bone diseases using osteogenic proteins are disclosed in U.S. Pat. No. 5,674,844, the entire contents of which are hereby incorporated by reference. Further the present compositions and methods find use in replacing or repairing bone or cartilage at injury sites such as bone breaks, bone fractures, and cartilage tears, periodontal tissue regeneration (e.g. general methods for periodontal tissue regeneration using osteogenic proteins are disclosed in U.S. Pat. No. 5,733,878, the entire contents of which are hereby incorporated by reference), liver regeneration, including following a partial hepatectomy (see, e.g., U.S. Pat. No. 5,849,686, the entire contents of which are hereby incorporated by reference), treatment of chronic renal failure (see, e.g., U.S. Pat. No. 6,861,404, the entire contents of which are hereby incorporated by reference), enhancing functional recovery following central nervous system ischemia or trauma (see, e.g. U.S. Pat. No. 6,407,060, the entire contents of which are hereby incorporated by reference), inducing dendritic growth (see, e.g., U.S. Pat. No. 6,949,505, the entire contents of which are hereby incorporated by reference), inducing neural cell adhesion (see, e.g., U.S. Pat. No. 6,800,603, the entire contents of which are hereby incorporated by reference), and treatment and prevention of Parkinson's disease (see, e.g., U.S. Pat. No. 6,506,729, the entire contents of which are hereby incorporated by reference). As another example, the present compositions and methods, including when targeting one or more BMPs, can be used to induce dentinogenesis. To date, the unpredictable response of dental pulp tissue to injury is a basic clinical problem in dentistry. Using standard dental surgical procedures, small areas (e.g., 2 mm) of dental pulps can be surgically exposed by removing the enamel and dentin immediately above the pulp (by drilling) of sample teeth, performing a partial amputation of the coronal pulp tissue, inducing hemostasis, application of the pulp treatment, and sealing and filling the cavity by standard procedures.

In various embodiments, the present invention relates to targeting a VEGF family member to treat diseases and conditions associated with angiogenesis, including but not limited to, solid tumor cancers, hemangiomas, rheumatoid arthritis, osteoarthritis, septic arthritis, asthma, atherosclerosis, idiopathic pulmonary fibrosis, vascular restenosis, arteriovenous malformations, meningiomas, neovascular glaucoma, psoriasis, Kaposi's Syndrome, angiofibroma, hemophilic joints, hypertrophic scars, Osler-Weber syndrome, pyogenic granuloma, retrolental fibroplasias, scleroderma, trachoma, von Hippel-Lindau disease, vascular adhesion pathologies, synovitis, dermatitis, neurological degenerative diseases, preeclampsia, unexplained female infertility, endometriosis, unexplained male infertility, pterygium, wounds, sores, skin ulcers, gastric ulcers, and duodenal ulcers. In various embodiments, the present invention relates to targeting a VEGF family member to treat angiogenesis-associated eye diseases, including without limitation any eye disease associated with abnormal intraocular neovascularization, including but not limited to retinopathy of prematurity, diabetic retinopathy, retinal vein occlusion, and age-related macular degeneration, as well diabetic macular edema and retinal vein occlusion. In an embodiment, the present compositions and methods relate to the treatment of wet age-related macular degeneration.

In a specific embodiment, the synthetic RNA targets a member of the interleukin family. The interleukins represent a large group of cytokines with diverse functions and were first characterized by expression in leukocytes and have since been shown to be expressed in a wide variety of cells, for example macrophages, TH-1 and TH-2 cells, T-lymphocytes, monocytes and bone marrow stroma. Broadly, the function of the immune system depends in a large part on the expression and function of the interleukins. In some embodiments, the target is one or more of interleukins 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 35 and 36, and, within each species of interleukin, various isotypes and/or interleukin receptors (e.g., IL-1R, IL-2R, IL-3R, IL-4R, IL-5R, IL-6R, IL-7R, IL-8R, IL-9R, IL-10R, IL-11R, IL-12R, IL-13R, IL-14R, IL-15R, IL-16R, IL-17R, IL-18R, IL-19R, IL-20R, IL-21R, IL-22R, IL-23R, IL-24R, IL-25R, IL-26, IL-27R, IL-28R, IL-29R, IL-30R, IL-31R, IL-32R, IL-33R, IL-34R, IL-35R, and IL-36R). In a specific embodiment, both IL-15 and IL-15R (e.g., IL-15RA) are targeted. Without wishing to be bound by theory, it is believed that the targeting of both interleukin (e.g., IL-15) and its cognitive interleukin receptor (e.g., IL-15RA) results in synergistic beneficial effects. In various embodiments, the present invention relates to targeting a member of the interleukin family to treat cancer, inflammatory, respiratory, autoimmune, cardiovascular, neurological, metabolic, and/or proliferative diseases, disorders, and/or conditions in a subject or organism, as described herein. In a specific embodiment, the present invention relates to targeting a member of the interleukin family to treat cancer. In a specific embodiment, the present invention relates to targeting a member of the interleukin family to treat rheumatoid arthritis.

In some embodiments, the present invention also relates to the following protein targets, e.g. in the treatment of disease: growth hormone (GH) e.g. human and bovine growth hormone, growth hormone-releasing hormones; interferon including α-, β-, or γ-interferons, etc., interleukin-I; interleukin-II; erythropoietin including α- and β-erythropoietin (EPO), granulocyte colony stimulating factor (GCSF), granulocyte macrophage colony stimulating factor (GM-CSF), anti-agiogenic proteins (e.g., angiostatin, endostatin) PACAP polypeptide (pituitary adenylate cyclase activating polypeptide), vasoactive intestinal peptide (VIP), thyrotrophin releasing hormone (TRH), corticotropin releasing hormone (CRH), vasopressin, arginine vasopressin (AVP), angiotensin, calcitonin, atrial naturetic factor, somatostatin, adrenocorticotropin, gonadotropin releasing hormone, oxytocin, insulin, somatotropin, plasminogen tissue activator, coagulation factors including coagulation factors VIII and IX, glucosylceramidase, sargramostim, lenograstin, filgrastin, dornase-α, molgramostim, PEG-L-asparaginase, PEG-adenosine deaminase, hirudin, eptacog-α (human blood coagulation factor Vila) nerve growth factors, transforming growth factor, epidermal growth factor, basic fibroblast growth factor, VEGF; heparin including low molecular weight heparin, calcitonin; antigens; monoclonal antibodies; vancomycin; desferrioxamine (DFO); parathyroid hormone, an immunogen or antigen, and an antibody such as a monoclonal antibody.

In some embodiments, the present methods allow for effective additional therapeutic agent (e.g. those described herein) activity and/or targeting to a cell and/or tissue of interest. For example, the present synthetic RNA can lead to increased expression of one or more targeting molecules that direct an additional therapeutic to the location of therapy. For example, the additional therapeutic agent may have a binding partner that the synthetic RNA encodes. For example, the synthetic RNA may induce the expression of an antigen that directs the therapeutic activity of an antibody that may be used in combination (e.g. herceptin, rituxan, campath, gemtuzumab, herceptin, panorex, rituximab, bexxar, edrecolomab, alemtuzumab, mylotrag, IMC-C225, smartin 195, and mitomomab). In some embodiments, the synthetic RNA can be injected directly into one or more of the tumors described herein and home the therapeutic antibody to the tumor.

In some embodiments, the present methods allow for effective additional therapeutic agent generation, especially when the additional therapeutic agent is a prodrug, for example, to produce an active form of the drug. In some embodiments, the synthetic RNA can be injected directly into one or more of the tumors described herein and home the prodrug to the tumor. For instance, the synthetic RNA may encode an enzyme that catalyzes the localized conversion of a nontoxic, systemically delivered agent into a potent chemotherapeutic agent.

In some embodiments, the nucleic acid drugs at the doses and regimens described herein may be used in combination with one or more additional agents (aka adjuvant therapy or combination agent). In some embodiments, the nucleic acid drugs at the doses and regimens described herein may be used in a human patient undergoing treatment with one or more additional agents. In some embodiments, the nucleic acid drug is used as an adjuvant or neoadjuvant to any of the additional agents described herein. In some embodiments, the invention pertains to co-administration and/or co-formulation. Any of the compositions described herein may be co-formulated and/or co-administered. In some embodiments, any nucleic acid drug described herein acts synergistically when co-administered with another agent and may be administered at doses that are lower than the doses commonly employed when such agents are used as monotherapy.

In some embodiments, any nucleic acid drug described herein may include derivatives that are modified, i.e., by the covalent attachment of any type of molecule to the composition such that covalent attachment does not prevent the activity of the composition. For example, but not by way of limitation, derivatives include composition that have been modified by, inter alia, glycosylation, lipidation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, metabolic synthesis of tunicamycin, etc. Additionally, the derivative can contain one or more non-classical amino acids. In various embodiments, one or more additional agents (aka adjuvant therapy or combination agent) may be conjugated to any nucleic acid drug described herein.

Contacting a cell with a steroid can suppress the innate immune response to foreign nucleic acids, and can increase the efficiency of nucleic acid delivery and translation. Certain embodiments are therefore directed to contacting a cell with a steroid. Other embodiments are directed to administering a steroid to a patient. Illustrative steroids include corticosteroid steroids. In some embodiments, the steroid is one or more of cortisone, hydrocortisone, prednisone, prednisolone, dexamethasone, triamcinolone, and betamethasone. In one embodiment, the steroid is hydrocortisone. In another embodiment, the steroid is dexamethasone.

Other embodiments are directed to administering to a patient a member of the group: an antibiotic, an antimycotic, and an RNAse inhibitor.

In various embodiments, the present invention contemplates the targeting of a protein having about 60% (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99%) sequence identity with any of the protein sequences disclosed herein.

Synthetic RNA Molecules

In some embodiments, a synthetic RNA molecule encodes a gene-editing protein. In embodiments, the synthetic RNA molecule is mRNA. In embodiments, the synthetic RNA molecule is in vitro transcribed.

In some embodiments, non-canonical nucleotides are incorporated into synthetic RNA to increase the efficiency with which the synthetic RNA can be translated into protein, and can decrease the toxicity of the synthetic RNA. In embodiments, the synthetic RNA molecule comprises one or more non-canonical nucleotides. In some embodiments, the nucleic acid comprises one or more non-canonical nucleotide members of the 5-methylcytidine de-methylation pathway. In some embodiments, the nucleic acid comprises at least one of: 5-methylcytidine, 5-hydroxymethylcytidine, 5-formylcytidine, and 5-carboxycytidine or a derivative thereof. In some embodiments, the nucleic acid comprises at least one of: pseudouridine, 5-methylpseudouridine, 5-methyluridine, 5-methylcytidine, 5-hydroxymethylcytidine, N4-methylcytidine, N4-acetylcytidine, and 7-deazaguanosine or a derivative thereof.

In some embodiments, the one or more non-canonical nucleotides are selected from: 5-methyluridine and 5-methylcytidine, 5-methyluridine and 7-deazaguanosine, 5-methylcytidine and 7-deazaguanosine, 5-methyluridine, 5-methylcytidine, and 7-deazaguanosine, and 5-methyluridine, 5-hydroxymethylcytidine, and 7-deazaguanosine. In some embodiments, the synthetic RNA molecule comprises at least two of: 5-methyluridine, 5-methylcytidine, 5-hydroxymethylcytidine, and 7-deazaguanosine or one or more derivatives thereof. In some embodiments, the synthetic RNA molecule comprises at least three of: 5-methyluridine, 5-methylcytidine, 5-hydroxymethylcytidine, and 7-deazaguanosine or one or more derivatives thereof. In embodiments, the mRNA comprises one or more non-canonical nucleotides selected from 2-thiouridine, 5-azauridine, pseudouridine, 4-thiouridine, 5-methyluridine, 5-methylpseudouridine, 5-aminouridine, 5-aminopseudouridine, 5-hydroxyuridine, 5-hydroxypseudouridine, 5-methoxyuridine, 5-methoxypseudouridine, 5-ethoxyuridine, 5-ethoxypseudouridine, 5-hydroxymethyluridine, 5-hydroxymethylpseudouridine, 5-carboxyuridine, 5-carboxypseudouridine, 5-formyluridine, 5-formylpseudouridine, 5-methyl-5-azauridine, 5-amino-5-azauridine, 5-hydroxy-5-azauridine, 5-methylpseudouridine, 5-aminopseudouridine, 5-hydroxypseudouridine, 4-thio-5-azauridine, 4-thiopseudouridine, 4-thio-5-methyluridine, 4-thio-5-aminouridine, 4-thio-5-hydroxyuridine, 4-thio-5-methyl-5-azauridine, 4-thio-5-amino-5-azauridine, 4-thio-5-hydroxy-5-azauridine, 4-thio-5-methylpseudouridine, 4-thio-5-aminopseudouridine, 4-thio-5-hydroxypseudouridine, 2-thiocytidine, 5-azacytidine, pseudoisocytidine, N4-methylcytidine, N4-aminocytidine, N4-hydroxycytidine, 5-methylcytidine, 5-aminocytidine, 5-hydroxycytidine, 5-methoxycytidine, 5-ethoxycytidine, 5-hydroxymethylcytidine, 5-carboxycytidine, 5-formylcytydine, 5-methyl-5-azacytidine, 5-amino-5-azacytidine, 5-hydroxy-5-azacytidine, 5-methylpseudoisocytidine, 5-aminopseudoisocytidine, 5-hydroxypseudoisocytidine, N4-methyl-5-azacytidine, N4-methylpseudoisocytidine, 2-thio-5-azacytidine, 2-thiopseudoisocytidine, 2-thio-N4-methylcytidine, 2-thio-N4-aminocytidine, 2-thio-N4-hydroxycytidine, 2-thio-5-methylcytidine, 2-thio-5-aminocytidine, 2-thio-5-hydroxycytidine, 2-thio-5-methyl-5-azacytidine, 2-thio-5-amino-5-azacytidine, 2-thio-5-hydroxy-5-azacytidine, 2-thio-5-methylpseudoisocytidine, 2-thio-5-aminopseudoisocytidine, 2-thio-5-hydroxypseudoisocytidine, 2-thio-N4-methyl-5-azacytidine, 2-thio-N4-methylpseudoisocytidine, N4-methyl-5-methylcytidine, N4-methyl-5-aminocytidine, N4-methyl-5-hydroxycytidine, N4-methyl-5-methyl-5-azacytidine, N4-methyl-5-amino-5-azacytidine, N4-methyl-5-hydroxy-5-azacytidine, N4-methyl methylpseudoisocytidine, N4-methyl-5-aminopseudoisocytidine, N4-methyl-5-hydroxypseudoisocytidine, N4-amino azacytidine, N4-aminopseudoisocytidine, N4-amino-5-methylcytidine, N4-amino-5-aminocytidine, N4-amino hydroxycytidine, N4-amino-5-methyl-5-azacytidine, N4-amino-5-amino-5-azacytidine, N4-amino-5-hydroxy azacytidine, N4-amino-5-methylpseudoisocytidine, N4-amino-5-aminopseudoisocytidine, N4-amino hydroxypseudoisocytidine, N4-hydroxy-5-azacytidine, N4-hydroxypseudoisocytidine, N4-hydroxy-5-methylcytidine, N4-hydroxy-5-aminocytidine, N4-hydroxy-5-hydroxycytidine, N4-hydroxy-5-methyl-5-azacytidine, N4-hydroxy-5-amino-5-azacytidine, N4-hydroxy-5-hydroxy-5-azacytidine, N4-hydroxy-5-methylpseudoisocytidine, N4-hydroxy-5-aminopseudoisocytidine, N4-hydroxy-5-hydroxypseudoisocytidine, 2-thio-N4-methyl-5-methylcytidine, 2-thio-N4-methyl-5-aminocytidine, 2-thio-N4-methyl-5-hydroxycytidine, 2-thio-N4-methyl-5-methyl-5-azacytidine, 2-thio-N4-methyl-5-amino-5-azacytidine, 2-thio-N4-methyl-5-hydroxy-5-azacytidine, 2-thio-N4-methyl-5-methylpseudoisocytidine, 2-thio-N4-methyl-5-aminopseudoisocytidine, 2-thio-N4-methyl-5-hydroxypseudoisocytidine, 2-thio-N4-amino-5-azacytidine, 2-thio-N4-aminopseudoisocytidine, 2-thio-N4-amino-5-methylcytidine, 2-thio-N4-amino-5-aminocytidine, 2-thio-N4-amino-5-hydroxycytidine, 2-thio-N4-amino-5-methyl-5-azacytidine, 2-thio-N4-amino-5-amino-5-azacytidine, 2-thio-N4-amino-5-hydroxy-5-azacytidine, 2-thio-N4-amino-5-methylpseudoisocytidine, 2-thio-N4-amino-5-aminopseudoisocytidine, 2-thio-N4-amino-5-hydroxypseudoisocytidine, 2-thio-N4-hydroxy-5-azacytidine, 2-thio-N4-hydroxypseudoisocytidine, 2-thio-N4-hydroxy-5-methylcytidine, N4-hydroxy-5-aminocytidine, 2-thio-N4-hydroxy-5-hydroxycytidine, 2-thio-N4-hydroxy-5-methyl-5-azacytidine, 2-thio-N4-hydroxy-5-amino-5-azacytidine, 2-thio-N4-hydroxy-5-hydroxy-5-azacytidine, 2-thio-N4-hydroxy-5-methylpseudoisocytidine, 2-thio-N4-hydroxy-5-aminopseudoisocytidine, 2-thio-N4-hydroxy-5-hydroxypseudoisocytidine, N6-methyladenosine, N6-aminoadenosine, N6-hydroxyadenosine, 7-deazaadenosine, 8-azaadenosine, N6-methyl-7-deazaadenosine, N6-methyl-8-azaadenosine, 7-deaza-8-azaadenosine, N6-methyl-7-deaza-8-azaadenosine, N6-amino-7-deazaadenosine, N6-amino-8-azaadenosine, N6-amino-7-deaza-8-azaadenosine, N6-hydroxyadenosine, N6-hydroxy-7-deazaadenosine, N6-hydroxy-8-azaadenosine, N6-hydroxy-7-deaza-8-azaadenosine, 6-thioguanosine, 7-deazaguanosine, 8-azaguanosine, 6-thio-7-deazaguanosine, 6-thio-8-azaguanosine, 7-deaza-8-azaguanosine, and 6-thio-7-deaza-8-azaguanosine.

In embodiments, at least 50%, at least 60%, at least 70%, at least 80%, at least 90%, or 100% of the non-canonical nucleotides comprises one or more of 5-hydroxycytidine, 5-methylcytidine, 5-hydroxymethylcytidine, 5-carboxycytidine, 5-formylcytidine, 5-methoxycytidine, pseudouridine, 5-hydroxyuridine, 5-methyluridine, 5-hydroxymethyluridine, 5-carboxyuridine, 5-formyluridine, 5-methoxyuridine, 5-hydroxypseudouridine, 5-methylpseudouridine, 5-hydroxymethylpseudouridine, 5-carboxypseudouridine, 5-formylpseudouridine, and 5-methoxypseudouridine.

In some embodiments, the synthetic RNA molecule comprises at least one of: one or more uridine residues, one or more cytidine residues, and one or more guanosine residues, and comprising one or more non-canonical nucleotides. In one embodiment, between about 20% and about 80% of the uridine residues are 5-methyluridine residues. In another embodiment, between about 30% and about 50% of the uridine residues are 5-methyluridine residues. In a further embodiment, about 40% of the uridine residues are 5-methyluridine residues. In one embodiment, between about 60% and about 80% of the cytidine residues are 5-methylcytidine residues. In another embodiment, between about 80% and about 100% of the cytidine residues are 5-methylcytidine residues. In a further embodiment, about 100% of the cytidine residues are 5-methylcytidine residues. In a still further embodiment, between about 20% and about 100% of the cytidine residues are 5-hydroxymethylcytidine residues. In one embodiment, between about 20% and about 80% of the guanosine residues are 7-deazaguanosine residues. In another embodiment, between about 40% and about 60% of the guanosine residues are 7-deazaguanosine residues. In a further embodiment, about 50% of the guanosine residues are 7-deazaguanosine residues. In one embodiment, between about 20% and about 80% or between about 30% and about 60% or about 40% of the cytidine residues are N4-methylcytidine and/or N4-acetylcytidine residues. In another embodiment, each cytidine residue is a 5-methylcytidine residue. In a further embodiment, about 100% of the cytidine residues are 5-methylcytidine residues and/or 5-hydroxymethylcytidine residues and/or N4-methylcytidine residues and/or N4-acetylcytidine residues and/or one or more derivatives thereof. In a still further embodiment, about 40% of the uridine residues are 5-methyluridine residues, between about 20% and about 100% of the cytidine residues are N4-methylcytidine and/or N4-acetylcytidine residues, and about 50% of the guanosine residues are 7-deazaguanosine residues. In one embodiment, about 40% of the uridine residues are 5-methyluridine residues and about 100% of the cytidine residues are 5-methylcytidine residues. In another embodiment, about 40% of the uridine residues are 5-methyluridine residues and about 50% of the guanosine residues are 7-deazaguanosine residues. In a further embodiment, about 100% of the cytidine residues are 5-methylcytidine residues and about 50% of the guanosine residues are 7-deazaguanosine residues. In one embodiment, about 40% of the uridine residues are 5-methyluridine residues, about 100% of the cytidine residues are 5-methylcytidine residues, and about 50% of the guanosine residues are 7-deazaguanosine residues. In another embodiment, about 40% of the uridine residues are 5-methyluridine residues, between about 20% and about 100% of the cytidine residues are 5-hydroxymethylcytidine residues, and about 50% of the guanosine residues are 7-deazaguanosine residues. In some embodiments, less than 100% of the cytidine residues are 5-methylcytidine residues. In other embodiments, less than 100% of the cytidine residues are 5-hydroxymethylcytidine residues. In one embodiment, each uridine residue in the synthetic RNA molecule is a pseudouridine residue or a 5-methylpseudouridine residue. In another embodiment, about 100% of the uridine residues are pseudouridine residues and/or 5-methylpseudouridine residues. In a further embodiment, about 100% of the uridine residues are pseudouridine residues and/or 5-methylpseudouridine residues, about 100% of the cytidine residues are 5-methylcytidine residues, and about 50% of the guanosine residues are 7-deazaguanosine residues.

Other non-canonical nucleotides that can be used in place of or in combination with 5-methyluridine include, but are not limited to: pseudouridine and 5-methylpseudouridine (a.k.a. "1-methylpseudouridine", a.k.a. "N1-methylpseudouridine") or one or more derivatives thereof. Other non-canonical nucleotides that can be used in place of or in combination with 5-methylcytidine and/or 5-hydroxymethylcytidine include, but are not limited to: pseudoisocytidine, 5-methylpseudoisocytidine, 5-hydroxymethylcytidine, 5-formylcytidine, 5-carboxycytidine, N4-methylcytidine, N4-acetylcytidine or one or more derivatives thereof. In certain embodiments, for example, when performing only a single transfection or when the cells being transfected are not particularly sensitive to transfection-associated toxicity or innate-immune signaling, the fractions of non-canonical nucleotides can be reduced. Reducing the fraction of non-canonical nucleotides can be beneficial, in part, because reducing the fraction of non-canonical nucleotides can reduce the cost of the nucleic acid. In certain situations, for example, when minimal immunogenicity of the nucleic acid is desired, the fractions of non-canonical nucleotides can be increased.

In embodiments, the synthetic RNA molecule comprises a 5' cap structure. In embodiments, the synthetic RNA molecule comprises a 5'-UTR comprising a Kozak consensus sequence. In embodiments, the synthetic RNA molecule comprises a 5'-UTR comprising a sequence that increases RNA stability in vivo. In embodiments, the synthetic RNA molecule comprises a 3'-UTR comprising a sequence that increases RNA stability in vivo. In embodiments, the 5'-UTR comprises an alpha-globin or beta-globin 5'-UTR sequence. In embodiments, the 3'-UTR comprises an alpha-globin or beta-globin 3'-UTR sequence. In embodiments, the synthetic RNA molecule comprises a 3' poly(A) tail.

Certain embodiments are directed to a nucleic acid comprising a 5'-cap structure selected from Cap 0, Cap 1, Cap 2, and Cap 3 or a derivative thereof. In one embodiment, the nucleic acid comprises one or more UTRs. In another embodiment, the one or more UTRs increase the stability of the nucleic acid. In a further embodiment, the one or more UTRs comprise an alpha-globin or beta-globin 5'-UTR. In a still further embodiment, the one or more UTRs comprise an alpha-globin or beta-globin 3'-UTR. In a still further embodiment, the synthetic RNA molecule comprises an alpha-globin or beta-globin 5'-UTR and an alpha-globin or beta-globin 3'-UTR. In one embodiment, the 5'-UTR comprises a Kozak sequence that is substantially similar to the Kozak consensus sequence. In another embodiment, the nucleic acid comprises a 3'-poly(A) tail. In a further embodiment, the 3'-poly(A) tail is between about 20 nt and about 250 nt or between about 120 nt and about 150 nt long. In a further embodiment, the 3'-poly(A) tail is about 20 nt, or about 30 nt, or about 40 nt, or about 50 nt, or about 60 nt, or about 70 nt, or about 80 nt, or about 90 nt, or about 100 nt, or about 110 nt, or about 120 nt, or about 130 nt, or about 140 nt, or about 150 nt, or about 160 nt, or about 170 nt, or about 180 nt, or about 190 nt, or about 200 nt, or about 210 nt, or about 220 nt, or about 230 nt, or about 240 nt, or about 250 nt long.

In some embodiments, the synthetic RNA comprises a tail composed of a plurality of adenines with one or more guanines.

Formulations/Administration

In some embodiments, the synthetic RNA molecule is a nucleic acid drug. In various embodiments, the nucleic acid drug is administered in a pharmaceutically acceptable formulation, including a formulation suitable for one or more of injection (e.g. subcutaneous injection, intradermal injection (including to the dermis or epidermis), subdermal injection, intramuscular injection, intraocular injection, intravitreal injection, intra-articular injection, intracardiac injection, intravenous injection, epidural injection, intrathecal injection, intratumoral injection) and topical administration and/or for administration to the integumentary system (e.g. to one or more of the epidermis (optionally selected from the stratum corneum, stratum lucidum, stratum granulosum, stratum spinosum, and stratum germinativum), basement membrane, dermis (optionally selected from the papillary region and the reticular region), subcutis, and conjunctiva) and/or for administration to the eye (e.g., to one or more of the cornea, sclera, iris, lens, corneal limbus, optic nerve, choroid, ciliary body, anterior segment, anterior chamber, and retina).

In various embodiments, the nucleic acid drug is formulated with one or more lipids to enhance uptake of the nucleic acid drug by cells. In other embodiments, the nucleic acid drug is formulated with one or more nanoparticles, optionally lipid or polymeric nanoparticles, to enhance uptake of the nucleic acid drug by cells, to enhance duration of protein expression, or to otherwise enhance the safety and/or efficacy of the nucleic acid drug.

In various embodiments, the nucleic acid drug is administered locally, optionally by one or more of subcutaneous injection, intradermal injection, subdermal injection and intramuscular injection, and the effective dose is administered to a surface area of about 4 $mm^2$ to about 1000 $mm^2$ (e.g. about, or no more than about, 4 $mm^2$, or 5 $mm^2$, or 10

$mm^2$, or 25 $mm^2$, or 50 $mm^2$, or 75 $mm^2$, or 100 $mm^2$, or 125 $mm^2$, or 150 $mm^2$, or 200 $mm^2$, or 500 $mm^2$, or 1000 $mm^2$).

In various embodiments, the nucleic acid drug is administered in a treatment regimen, optionally with an additional agent or adjuvant therapy described herein, and the administration is about weekly to about once every 24 weeks (e.g. about, or not more than about, weekly, or once every 2 weeks, or once every 3 weeks, or once every 4 weeks, or once every 5 weeks, or once every 6 weeks, or once every 7 weeks, or once every 8 weeks, or once every 9 weeks, or once every 9 weeks, or once every 9 weeks, or once every 9 weeks, or once every 10 weeks, or once every 11 weeks, or once every 12 weeks, or once every 13 weeks, or once every 14 weeks, or once every 15 weeks, or once every 20 weeks, or once every 24 weeks). In other embodiments, the nucleic acid drug is administered in a treatment regimen, optionally with an additional agent or adjuvant therapy described herein, and the administration is about daily to about weekly (e.g., about, or not more than about, daily, or once every 2 days, or once every 3 days, or once every 4 days, or once every 5 days, or once every 6 days, or weekly).

The nucleic acid drug described herein can possess a sufficiently basic functional group, which can react with an inorganic or organic acid, or a carboxyl group, which can react with an inorganic or organic base, to form a pharmaceutically acceptable salt. A pharmaceutically acceptable acid addition salt is formed from a pharmaceutically acceptable acid, as is well known in the art. Such salts include the pharmaceutically acceptable salts listed in, for example, *Journal of Pharmaceutical Science,* 66, 2-19 (1977) and *The Handbook of Pharmaceutical Salts; Properties, Selection, and Use*. P. H. Stahl and C. G. Wermuth (eds.), Verlag, Zurich (Switzerland) 2002, which are hereby incorporated by reference in their entirety.

Pharmaceutically acceptable salts include, by way of non-limiting example, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, pamoate, phenylacetate, trifluoroacetate, acrylate, chlorobenzoate, dinitrobenzoate, hydroxybenzoate, methoxybenzoate, methyl benzoate, o-acetoxybenzoate, naphthalene-2-benzoate, isobutyrate, phenylbutyrate, α-hydroxybutyrate, butyne-1,4-dicarboxylate, hexyne-1,4-dicarboxylate, caprate, caprylate, cinnamate, glycollate, heptanoate, hippurate, malate, hydroxymaleate, malonate, mandelate, mesylate, nicotinate, phthalate, teraphthalate, propiolate, propionate, phenylpropionate, sebacate, suberate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, xylenesulfonate, and tartarate salts.

The term "pharmaceutically acceptable salt" also refers to a salt of the compositions of the present invention having an acidic functional group, such as a carboxylic acid functional group, and a base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or tri-alkylamines, dicyclohexylamine; tributyl amine; pyridine; N-methyl, N-ethylamine; diethylamine; triethylamine; mono-, bis-, or tris-(2-0H-lower alkylamines), such as mono-; bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as N,N-dimethyl-N-(2-hydroxyethyl)amine or tri-(2-hydroxyethyl) amine; N-methyl-D-glucamine; and amino acids such as arginine, lysine, and the like.

In some embodiments, the compositions described herein are in the form of a pharmaceutically acceptable salt.

In various embodiments, the present invention pertains to pharmaceutical compositions comprising the nucleic acid drug described herein and a pharmaceutically acceptable carrier or excipient. In some embodiments, the present invention pertains to pharmaceutical compositions comprising the present nucleic acid drug. In a further embodiment, the present invention pertains to pharmaceutical compositions comprising a combination of the nucleic acid drug and any other therapeutic agents described herein. Any pharmaceutical compositions described herein can be administered to a subject as a component of a composition that comprises a pharmaceutically acceptable carrier or vehicle. Such compositions can optionally comprise a suitable amount of a pharmaceutically acceptable excipient so as to provide the form for proper administration.

In various embodiments, pharmaceutical excipients can be liquids, such as water and oils, including those of petroleum, animal, vegetable, or synthetic origin, such as peanut oil, soybean oil, mineral oil, sesame oil and the like. The pharmaceutical excipients can be, for example, saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Water is a useful excipient when any agent described herein is administered intravenously. Saline solutions and aqueous dextrose and glycerol solutions can also be employed as liquid excipients, specifically for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Any agent described herein, if desired, can also comprise minor amounts of wetting or emulsifying agents, or pH buffering agents. Other examples of suitable pharmaceutical excipients are described in *Remington's Pharmaceutical Sciences* 1447-1676 (Alfonso R. Gennaro eds., 19th ed. 1995), incorporated herein by reference.

The present invention includes the described pharmaceutical compositions (and/or additional therapeutic agents) in various formulations. Any inventive pharmaceutical composition (and/or additional therapeutic agents) described herein can take the form of solutions, suspensions, emulsion, drops, tablets, pills, pellets, capsules, capsules containing liquids, gelatin capsules, powders, sustained-release formulations, suppositories, emulsions, aerosols, sprays, suspensions, lyophilized powder, frozen suspension, desiccated powder, or any other form suitable for use. In one embodiment, the composition is in the form of a capsule. In another embodiment, the composition is in the form of a tablet. In yet another embodiment, the pharmaceutical composition is formulated in the form of a soft-gel capsule. In a further embodiment, the pharmaceutical composition is formulated in the form of a gelatin capsule. In yet another embodiment, the pharmaceutical composition is formulated as a liquid.

Where necessary, the inventive pharmaceutical compositions (and/or additional agents) can also include a solubilizing agent. Also, the agents can be delivered with a suitable vehicle or delivery device as known in the art. Combination therapies outlined herein can be co-delivered in a single delivery vehicle or delivery device.

The formulations comprising the inventive pharmaceutical compositions (and/or additional agents) of the present invention may conveniently be presented in unit dosage forms and may be prepared by any of the methods well known in the art of pharmacy. Such methods generally include the step of bringing the therapeutic agents into association with a carrier, which constitutes one or more accessory ingredients. Typically, the formulations are prepared by uniformly and intimately bringing the therapeutic agent into association with a liquid carrier, a finely divided solid carrier, or both, and then, if necessary, shaping the product into dosage forms of the desired formulation (e.g., wet or dry granulation, powder blends, etc., followed by tableting using conventional methods known in the art).

In various embodiments, any pharmaceutical compositions (and/or additional agents) described herein is formulated in accordance with routine procedures as a composition adapted for a mode of administration described herein.

Lipids/Cell Contacting/Transfection

In aspects, the present invention relates delivery of the present synthetic RNA molecules via a lipid. In embodiments, the lipid is a compound of Formula (I)

(I)

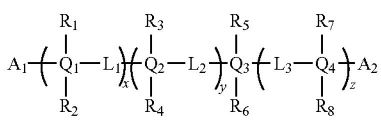

wherein: $Q_1$, $Q_2$, $Q_3$, and $Q_4$ are independently an atom or group capable of adopting a positive charge;

$A_1$ and $A_2$ are independently null, H, or optionally substituted $C_1$-$C_6$ alkyl;

$L_1$, $L_2$, and $L_3$ are independently null, a bond, $(C_1$-$C_{20})$alkanediyl, (halo)$(C_1$-$C_{20})$alkanediyl, (hydroxy)$(C_1$-$C_{20})$alkanediyl, (alkoxy)$(C_1$-$C_{20})$alkanediyl, arylene, heteroarylene, cycloalkanediyl, heterocycle-diyl, or any combination of the aforementioned optionally linked by one or more of an ether, an ester, an anhydride, an amide, a carbamate, a secondary amine, a tertiary amine, a quaternary ammonium, a thioether, a urea, a carbonyl, or an imine;

$R_1$, $R_2$, $R_3$, $R_4$, $R_5$, $R_6$, $R_7$, and $R_8$ are independently null, H, $(C_1$-$C_{60})$alkyl, (halo)$(C_1$-$C_{60})$alkyl, (hydroxy)$(C_1$-$C_{60})$alkyl, (alkoxy)$(C_1$-$C_{60})$alkyl, $(C_2$-$C_{60})$alkenyl, (halo)$(C_2$-$C_{60})$alkenyl, (hydroxy)$(C_2$-$C_{60})$alkenyl, (alkoxy)$(C_2$-$C_{60})$alkenyl, $(C_2$-$C_{60})$alkynyl, (halo)$(C_2$-$C_{60})$alkynyl, (hydroxy)$(C_2$-$C_{60})$alkynyl, (alkoxy)$(C_2$-$C_{60})$alkynyl, wherein at least one of $R_1$, $R_2$, $R_3$, $R_4$, $R_5$, $R_6$, $R_7$, and $R_8$ comprises at least two unsaturated bonds; and x, y, and z are independently 0, 1, 2, 3, 4, 5, 6, 7, 8, 9, 10, 11, 12, 13, 14, or 15.

In embodiments, the lipid is a compound of Formula (II):

(II)

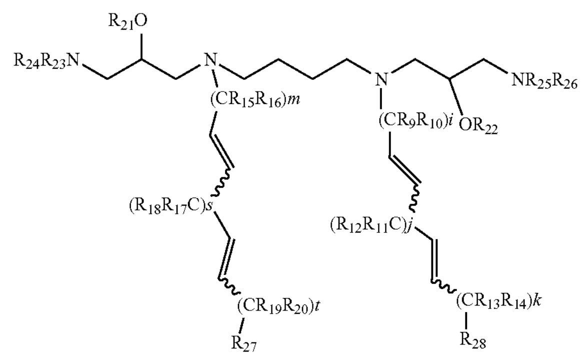

wherein: R9, R10, R11, R12, R13, R14, R15, R16, R17, R18, R19, R20, R21, R22, R23, R24, R25, R26, R27, and R28 are independently H, halo, OH, (C1-C6)alkyl, (halo)(C1-C6)alkyl, (hydroxy)(C1-C6)alkyl, (alkoxy)(C1-C6)alkyl, aryl, heteroaryl, cycloalkyl, or heterocyclo; and i, j, k, m, s, and t are independently 0, 1, 2, 3, 4, 5, 6, 7, 8, 9, 10, 11, 12, 13, 14, or 15.

In embodiments, the lipid is a compound of Formula (III):

(III)

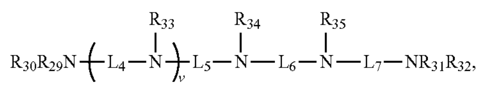

wherein $L_4$, $L_5$, $L_6$, and $L_7$ are independently a bond, $(C_1$-$C_{20})$alkanediyl, (halo)$(C_1$-$C_{20})$alkanediyl, (hydroxy)$(C_1$-$C_{20})$alkanediyl, (alkoxy)$(C_1$-$C_{20})$alkanediyl, arylene, heteroarylene, cycloalkanediyl, heterocycle-diyl, $-(CH_2)_{v1}-C(O)-$, $-((CH_2)_{v1}-O)_{v2}-$, or $-((CH_2)_{v1}-C(O)-O)_{v2}-$;

$R_{29}$, $R_{30}$, $R_{31}$, $R_{32}$, $R_{33}$, $R_{34}$, and $R_{35}$ are independently H, $(C_1$-$C_{60})$alkyl, (halo)$(C_1$-$C_{60})$alkyl, (hydroxy)$(C_1$-$C_{60})$alkyl, (alkoxy)$(C_1$-$C_{60})$alkyl, $(C_2$-$C_{60})$alkenyl, (halo)$(C_2$-$C_{60})$alkenyl, (hydroxy)$(C_2$-$C_{60})$alkenyl, (alkoxy)$(C_2$-$C_{60})$alkenyl, $(C_2$-$C_{60})$alkynyl, (halo)$(C_2$-$C_{60})$alkynyl, (hydroxy)$(C_2$-$C_{60})$alkynyl, (alkoxy)$(C_2$-$C_{60})$alkynyl, wherein at least one of $R_{29}$, $R_{30}$, $R_{31}$, $R_{32}$, $R_{33}$, $R_{34}$, and $R_{35}$ comprises at least two unsaturated bonds;

v, $v_1$ and $v_2$ are independently 0, 1, 2, 3, 4, 5, 6, 7, 8, 9, 10, 11, 12, 13, 14, or 15.

In embodiments, the lipid is a compound of Formula (IV):

(IV)

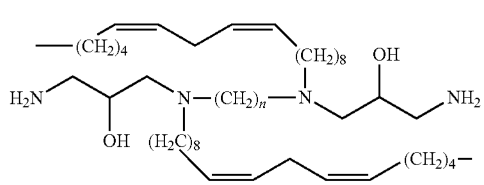

wherein n is 1, 2, 3, 4, 5, 6, 7, 8, 9, 10, 11, 12, 13, 14, or 15.

In embodiments, the lipid is a compound of Formula (V):

(V)

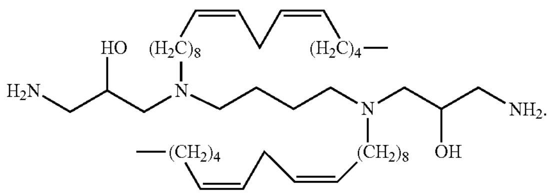

In embodiments, the lipid is a compound of Formula (VI):

(VI)

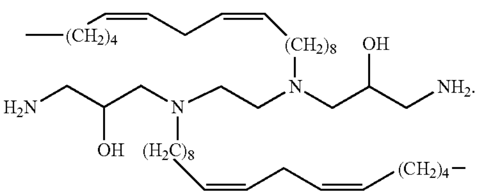

In embodiments, the lipid is a compound of Formula (VII):

(VII)

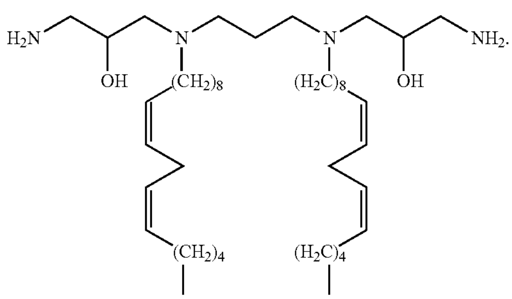

In embodiments, the lipid is a compound of Formula (VIM):

(VIII)

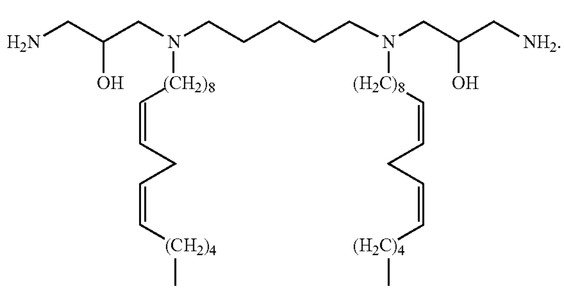

In embodiments, the lipid is a compound of Formula (IX):

(IX)

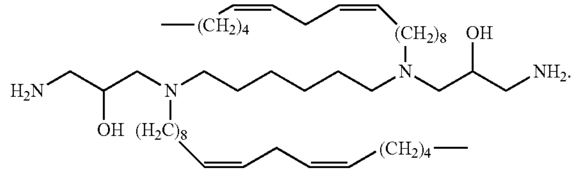

In embodiments, the lipid is a compound of Formula (X):

(X)

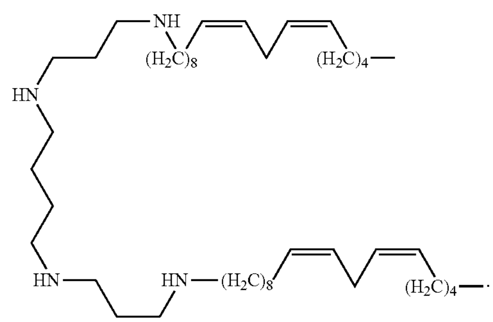

In embodiments, the lipid is a compound of Formula (XI):

(XI)

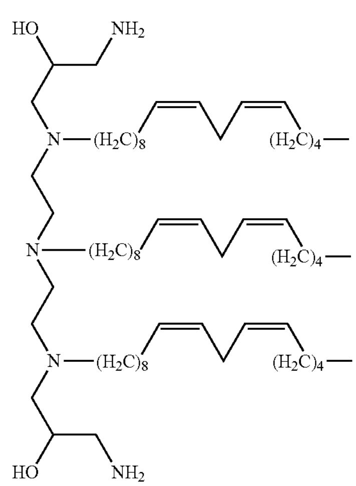

In embodiments, the lipid is a compound of Formula (XII):

(XII)

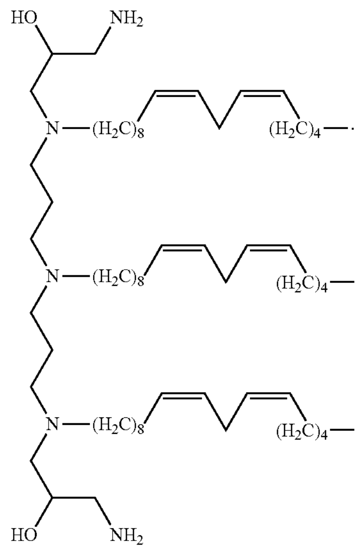

In embodiments, the lipid is a compound of Formula (XIII):

(XIII)

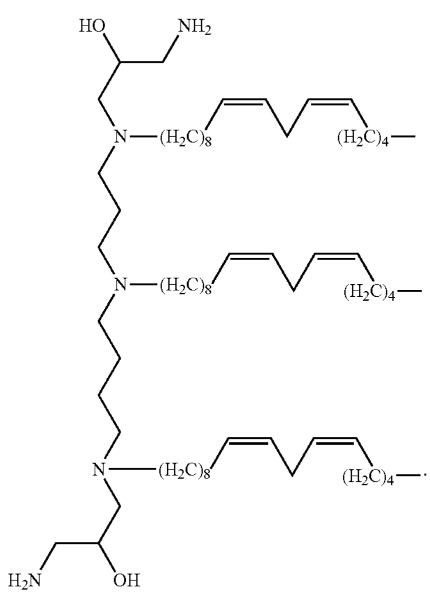

In embodiments, the lipid is a compound of Formula (XIV):

(XIV)

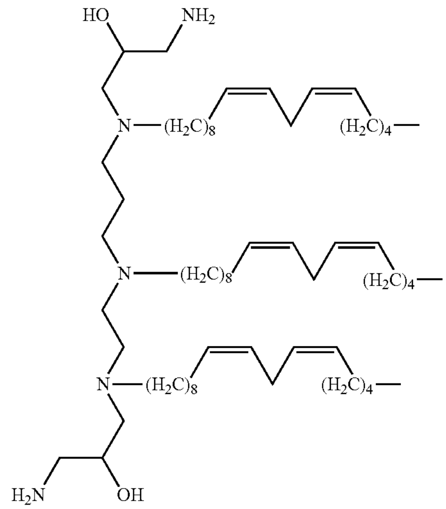

.

In embodiments, the lipid is a compound of Formula (XV):

(XV)

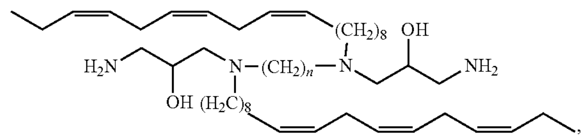

wherein n is 1, 2, 3, 4, 5, 6, 7, 8, 9, 10, 11, 12, 13, 14, or 15.

In embodiments, the lipid is a compound of Formula (XVI):

(XVI)

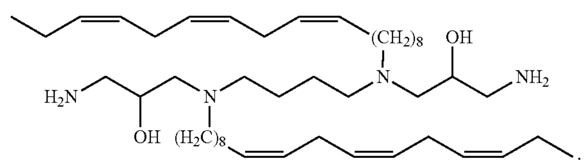

In embodiments, the present compounds (e.g. of Formulae I-XVI) are components of a pharmaceutical composition and/or a lipid aggregate and/or a lipid carrier and/or a lipid nucleic-acid complex and/or a liposome and/or a lipid nanoparticle.

In embodiments, the present compounds (e.g. of Formulae I-XVI) are components of a pharmaceutical composition and/or a lipid aggregate and/or a lipid carrier and/or a lipid nucleic-acid complex and/or a liposome and/or a lipid nanoparticle which does not require an additional or helper lipid. In embodiments, the present compounds (e.g. of Formulae I-XVI) are components of a pharmaceutical composition and/or a lipid aggregate and/or a lipid carrier and/or a lipid nucleic-acid complex and/or a liposome and/or a lipid nanoparticle that further comprises a neutral lipid (e.g. dioleoylphosphatidylethanolamine (DOPE), 1,2-Dioleoyl-sn-glycero-3-phosphocholine (DOPC), or cholesterol) and/or a further cationic lipid (e.g. N-[1-(2,3-dioleoyloxy)propyl]-N,N,N-trimethylammonium chloride (DOTMA), 1,2-bis(oleoyloxy)-3-3-(trimethylammonium) propane (DOTAP), or 1,2-dioleoyl-3-dimethylammonium-propane (DODAP)). This invention is further illustrated by the following non-limiting examples.

EXAMPLES

As used herein, ToRNAdo refers to certain lipids described herein, (see, e.g. U.S. Pat. No. 10,501,404, incorporated herein by reference in it entirety).

As used herein, NoveSlice refers to a gene-editing protein with a DNA binding domain having at least one repeat of LTPEQVVAIAS*RVD*GGKQALETVQRLLPVLCQAGHGG, (SEQ ID NO: 33) unless indicated otherwise.

Example 1. NovelSlice Gene-Editing Protein Creation and Testing

NoveSlice gene-editing proteins were created and tested using the process shown in FIG. 1. In step 1 and 2, the DNA binding domain target sequence was created either through the use of NEB enzymes in Golden Gate Assembly or directly synthesized through second party gene synthesis. In step 3, NEB stable competent *E. coli* (high efficiency; Cat. No. C3040H) were transformed. In step 4, colonies were picked. In step 5, the sequence was verified using GeneWiz Plasmid Sequencing. In step 6, mRNA was synthesized using NEB T7 RNA synthesis (Cat. No. E2040). In optional step 6, the mRNA was subjected to a cell-free Amplicon Cutting Assay (cfACA) utilizing Promega rabbit reticulocyte lysate (Cat. No. L4960). In step 7, synthetic mRNA was transfected using the ThermoFisher Neon Transfection System, ThermoFisher Lipofectamine 3000, or ToRNAdo™ (see, e.g. U.S. Pat. No. 10,501,404, incorporated herein by reference in its entirety). Cells were later extracted using a Promega Maxwell® RSC Cultured Cells DNA Kit (cat. No. AS1620), Qiagen QIAamp DNA Micro or Mini Kit (cat. No. 56304 or 51306), or Zymo Quick-DNA Miniprep Kit (cat. No. D3024). In step 8, the gene-editing protein thus created was tested using one or more of: (a) a T7E1 Mismatch assay—KapaBiosystems HiFi HotStart PCR Kit (cat. No KK2502), followed by NEB T7 Endonuclease I (Cat. No. M0302L), (b) a novel off-target assay; or (c) fragment analysis by GeneWiz.

The process involving steps 1-7 was created to ensure a streamlined workflow meant to efficiently process and test all gene-editing mRNA. The work flow includes target sequence selection and subsequent analysis to determine target specify, off-target effects, insertion rates, and targeting efficiency.

NoveSlice gene-editing proteins were made to include a FLAG-tag which enabled detection both from In-Vivo Translation and In-Vitro Translation (FIG. 2). Gene-editing constructs were checked using RNA titration of both TALENs and NoveSlices following an Immunoprecipitation. Once the samples were Immunoprecipitated, they were run using the FLAG-Tag antibodies on the Biotechne Protein Simple Wes device. FIG. 2 shows successful expression and detection of both a TALEN and NoveSlice gene-editing protein with the same FLAG-tag.

Example 2. DNA Binding Domain Distances in Gene-Editing Protein Dimers

Figure 3A:
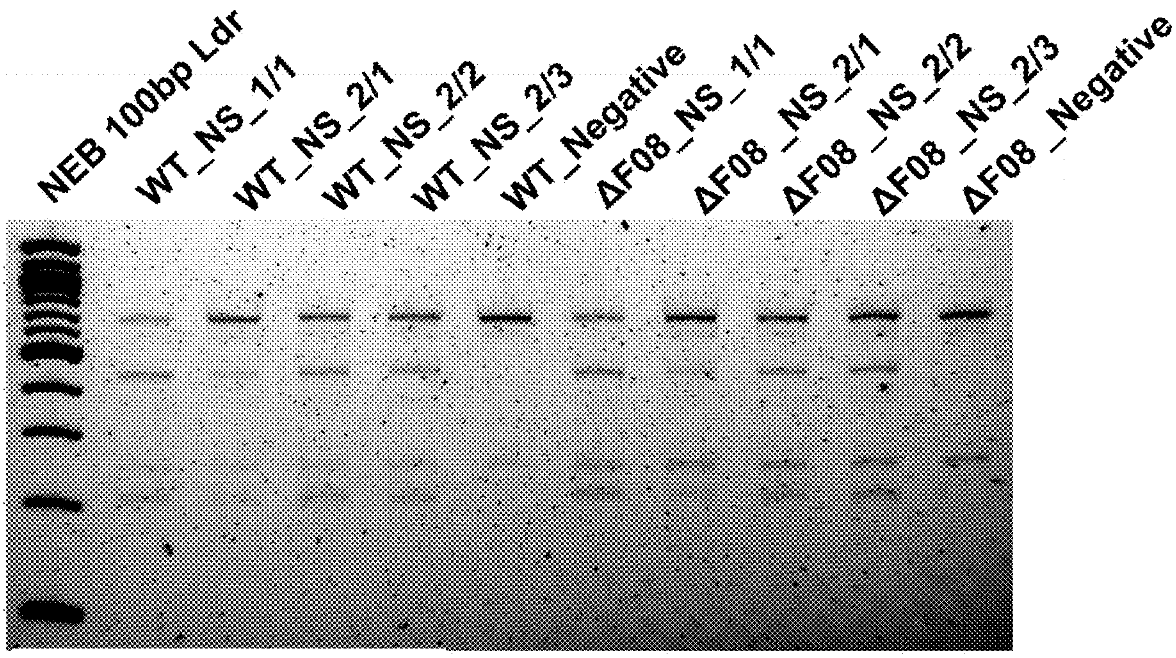
FIG. 3A depicts the use of a Cell-Free Amplicon-Cutting assay (cfACA) as a new rapid way to screen a variety of NoveSlice gene-editing proteins (NS, denoting a NoveSlice gene-editing protein, which are translated from mRNA and are directed to either the wild-type (WT) CFTR gene or a CFTR gene with a ΔF08 mutation.
Figure 3B:
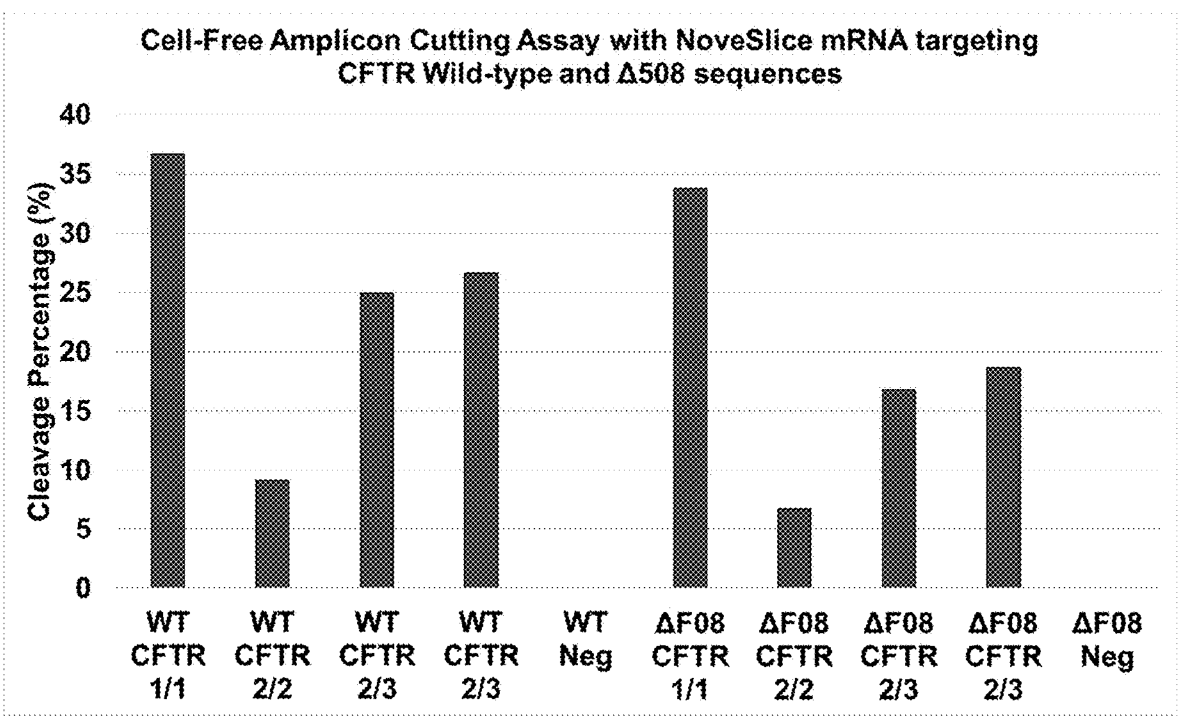
FIG. 3B depicts the cleavage percentage, as determined by ImageJ, of NoveSlice gene-editing proteins targeting either the wild-type (WT) CFTR gene or a CFTR gene with a ΔF08 mutation. NS denotes a NoveSlice gene-editing protein.
Figure 3D:
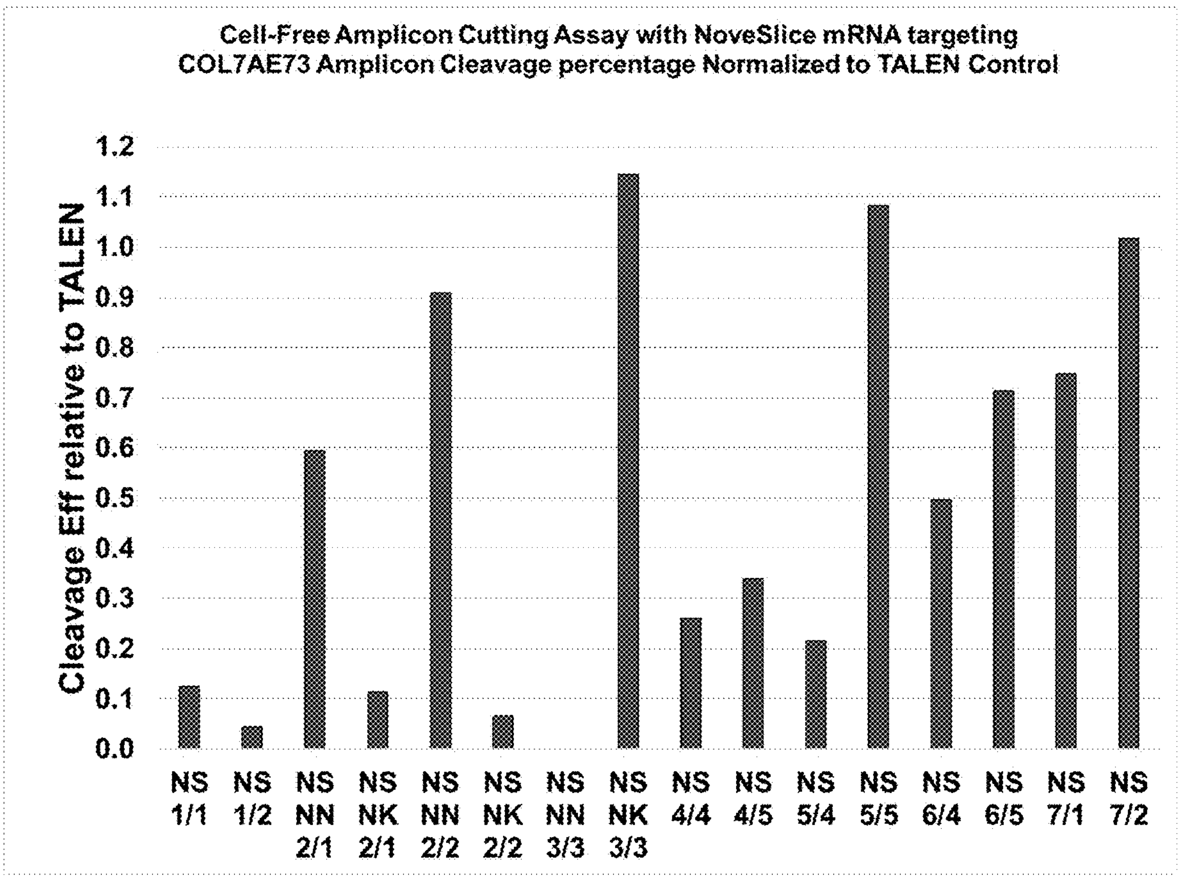
FIG. 3D depicts the cleavage efficiency of a variety of NoveSlice gene-editing proteins, as compared to TALEN, with different DNA sequence targets around the Splice acceptor. NS denotes a NoveSlice gene-editing protein. NN and NK denote amino acid sequences of the repeat variable domain (RVD) in the NoveSlice gene-editing proteins.

A cell-free Amplicon-Cutting assay (cfACA) was used as a new rapid way to screen a variety gene-editing proteins, which were translated from mRNA (FIG. 3A-E). Testing of this system was performed using a variety of different target sites. Nucleic acid constructs were gBlock synthesized from IDT to target the wild-type (WT) and ΔF08 mutation in the CFTR gene (FIG. 3A). Using ImageJ, the cleavage percentage from this assay was calculated to determine how the different pairs targeting the same DNA sequence performed both with and without the deletion (FIG. 3B). A variety of different spacings between the two DNA-binding domains of each gene-editing protein dimer was tested using a targeting splice acceptor for COL7A1E73 (FIG. 3C). ImageJ was used to determine cleavage efficiency, which was then normalized to the positive control, which was a TALEN. The effects on cleavage efficiency of converting all RVDs comprising NN to NK were also tested (FIG. 3D).

Example 3. Conditional Activity: Methylation

Figure 3E:
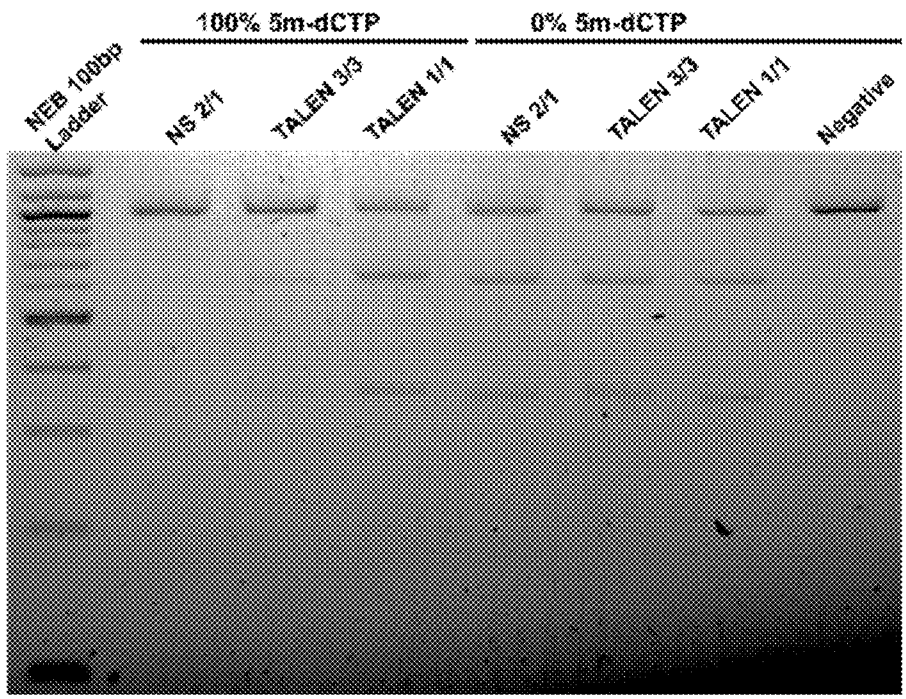
FIG. 3E depicts the effect of methylation on the cleavage efficiency of gene-editing proteins. The 100% 5m-dCTP condition mimics hypermethylation of target DNA, while the 0% 5m-dCTP condition mimics unmethylated target DNA. NS denotes a NoveSlice gene-editing protein.

A cell-free Amplicon-Cutting assay (cfACA) was used to screen a variety gene-editing proteins, which were translated from mRNA as in Example 2. dCTP was replaced by 5m-dCTP to create an amplicon that would mimic hypermethylated DNA in the target region and throughout (FIG. 3E). It was observed that while TALEN gene-editing proteins still cleaved hypermethylated sites (100% 5m-dCTP), indicating that such activity could result in off-target cutting, the NoveSlice gene-editing proteins did not cleave hypermethylated sites, but only cleaved unmethylated sites (0% 5m-dCTP), indicating that such activity probably did not result in off-target cutting.

Example 4. Conditional Activity: Temperature Dependence

Figure 4A:
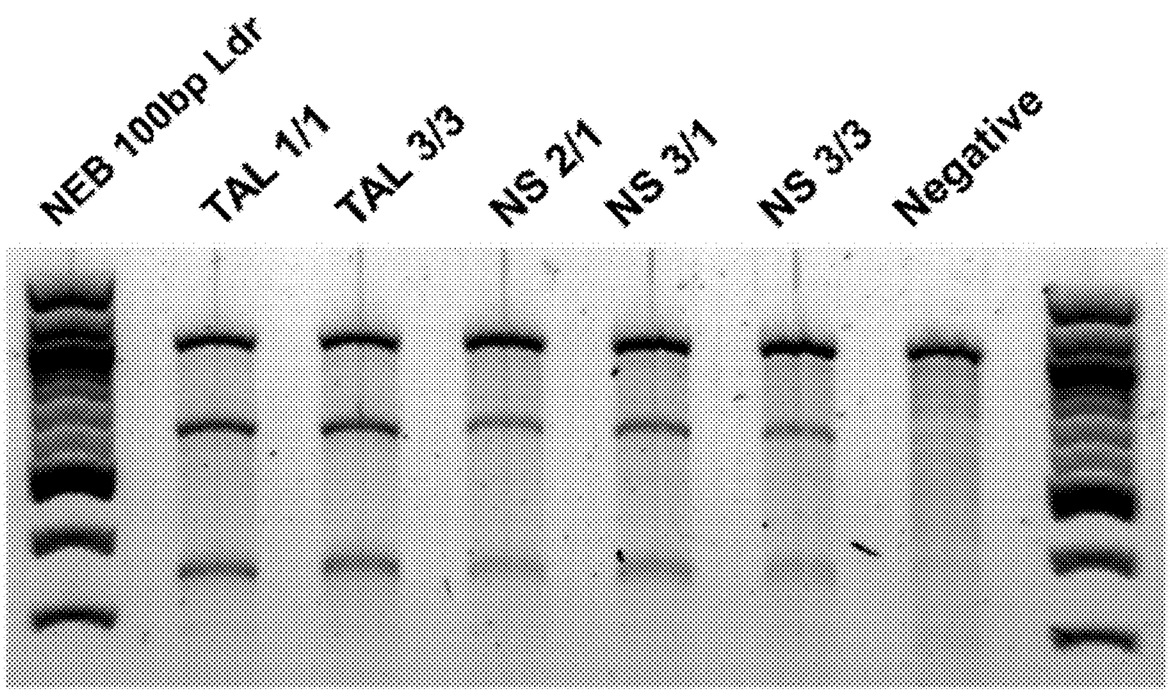
FIG. 4A depicts that gene-editing proteins cleave a target Human AAVS1 site under normal conditions (37° C., 19% $O_2$, and 5% $CO_2$).
Figure 4B:
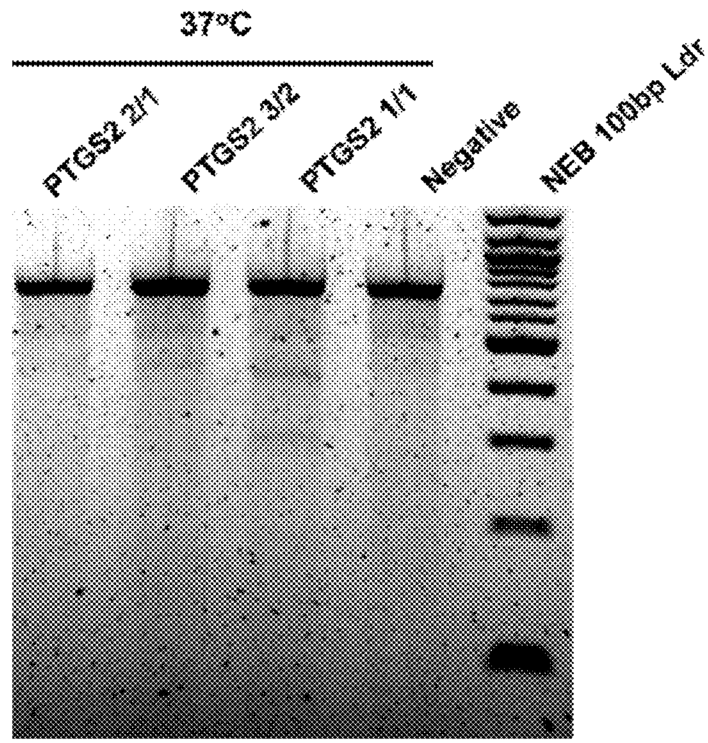
FIGS. 4B and 4C depict the effect of temperature on the cleavage efficiency of gene-editing proteins, where the target is the Human AAVS1 site.
Figure 4C:
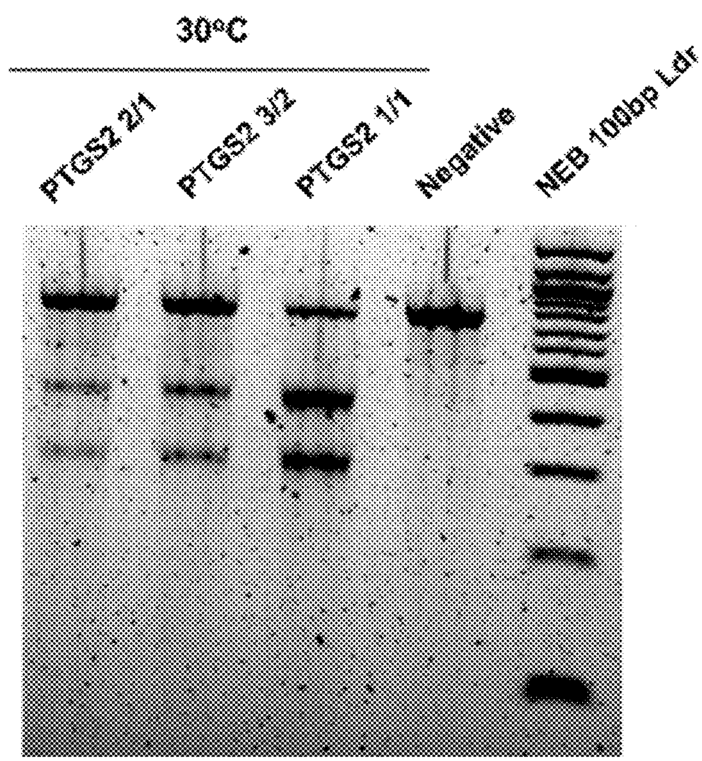

Human neonatal epidermal keratinocytes were transfected using 500 ng mRNA targeting the Human AAVS1 site using ToRNAdo™ (see, e.g. U.S. Pat. No. 10,501,404, incorporated herein by reference in its entirety) under normal condition (37° C., 19% $O_2$, and 5% $CO_2$). The cells were subsequently were harvested 48 hours later. DNA was extracted and Surveyor PCR and T7E1 was performed. The samples performed well under these conditions (FIG. 4A). IPSCs were transfected using 500 ng mRNA, under two different temperature conditions: 37° C., 19% $O_2$, and 5% $CO_2$ (FIG. 4B) and 30° C., 19% $O_2$, and 5% $CO_2$ (FIG. 4C). Cells were treated similarly to the samples assayed in FIG. 4A and imaged on a gel. It was observed that for the AAVS1 target site, low temperature restored function of the gene-editing proteins.

Example 5. Novel Engineered Nuclease Domains (Comprising Catalytic Domains)

Figure 5:
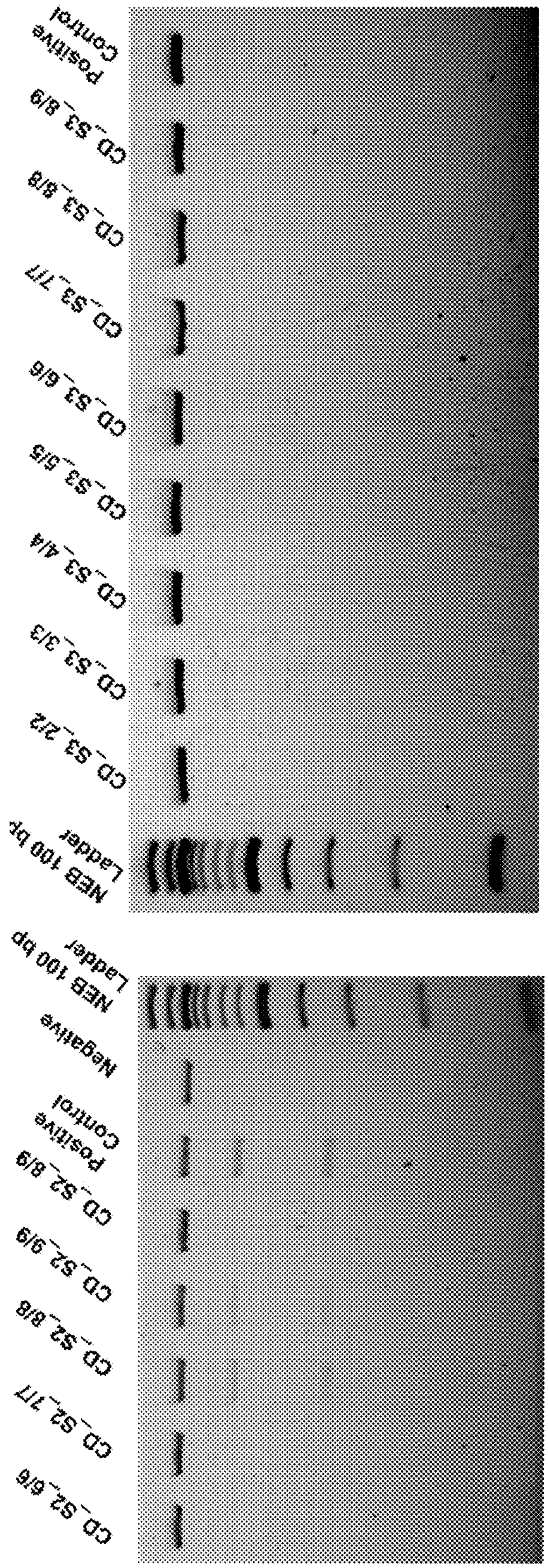
FIG. 5 depicts different NoveSlice gene-editing proteins, each with different catalytic domains (CD).

Various NoveSlice gene-editing proteins were created, with each having different catalytic domains. cfACA experiments were performed as described in Examples 2 and 3 to rapidly screen and test the NoveSlice gene-editing proteins with different catalytic domains (CD) (FIG. 5). Each catalytic domain was constructed by combining one or more secondary structure elements, e.g., α1 and/or β1, from FokI with zero, one, or more secondary structure elements from StsI (FIG. 6).

Example 6 Novel Engineered DNA-Binding Domains

Figure 7B:
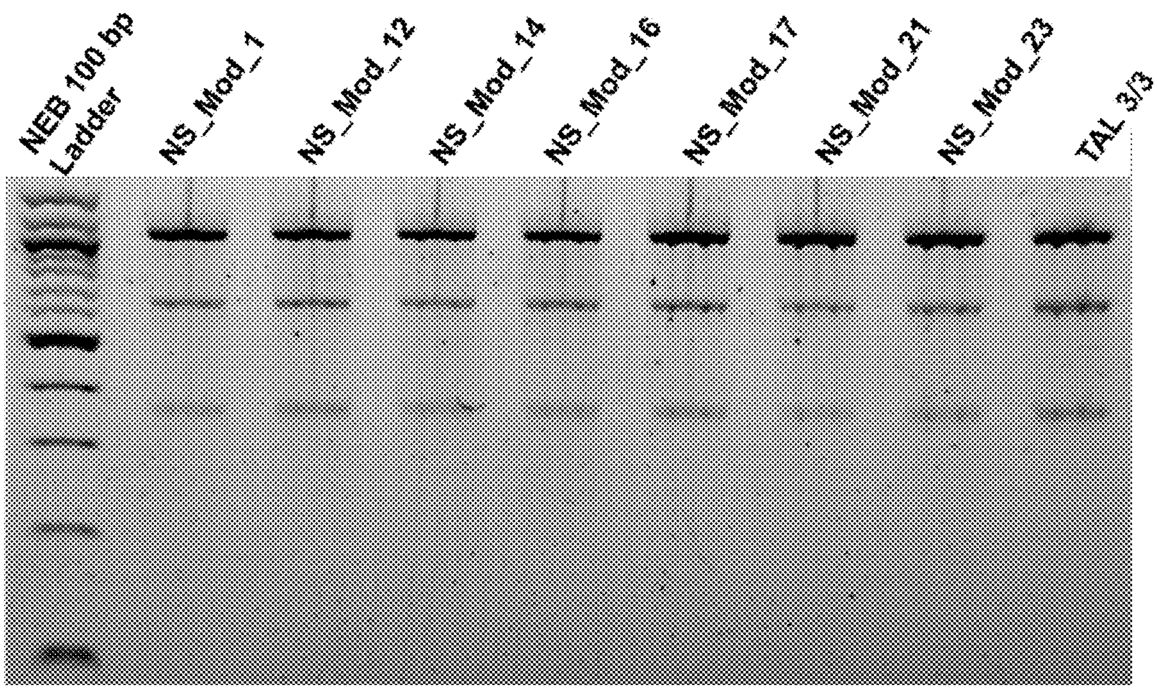
FIG. 7B depicts transfections using Noveslice gene-editing proteins (NS), where the left gene editing protein in each pair contains a modified linker in the second last synthetic DNA Binding Domain (sDBD) position and where the pairs were designed to target the Human AAVS1 site. TAL is a TALEN gene-editing protein control.
Figure 7C:
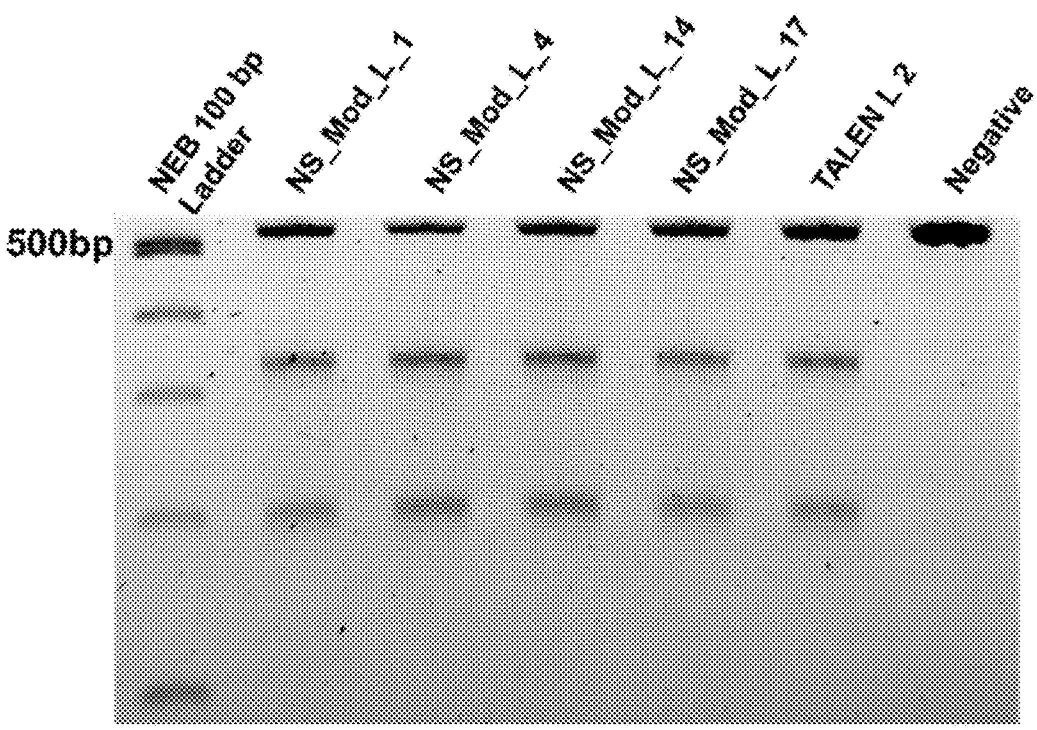
FIG. 7C depicts transfections using Noveslice gene-editing proteins (NS), where the left gene editing protein in each pair contains multiple modified linkers in the synthetic DNA Binding Domain (sDBD) position and where the pairs were designed to target the Human Col7A1E73 site, using a NoveSlice Right hand. TALEN is a TALEN gene-editing protein control.

Different NoveSlice gene-editing proteins were engineered using different linkers in the synthetic DNA Binding Domain (sDBD) (FIG. 7A). The linkers were designed with the aim of increasing protein targeting efficiency and fidelity of the NoveSlice gene-editing proteins. NoveSlice gene-editing protein dimers with the left gene editing protein containing a modified linker in the second last sDBD position were created, where the dimers were designed to target the Human AAVS1 site. Transfections where performed using ToRNAdo™ (see, e.g. U.S. Pat. No. 10,501,404, incorporated herein by reference in its entirety) and 500 ng of mRNA on Neonatal Human Epidermal Keratinocytes. Cells were extracted 48 hours post transfection and a T7E1 was performed (FIG. 7B). IPSC were transfected with NoveSlice gene-editing protein dimers engineered such that the left gene editing protein contained multiple modified linkers in the sDBD position. The target was the Human Col7A1E73 site and used a NoveSlice Right hand. Transfections where performed using Lipofectamine 3000 and 2 ug of mRNA on IPSCs. Cells were extracted 48 hours post transfection and a T7E1 was performed (FIG. 7C).

Figure 8A:
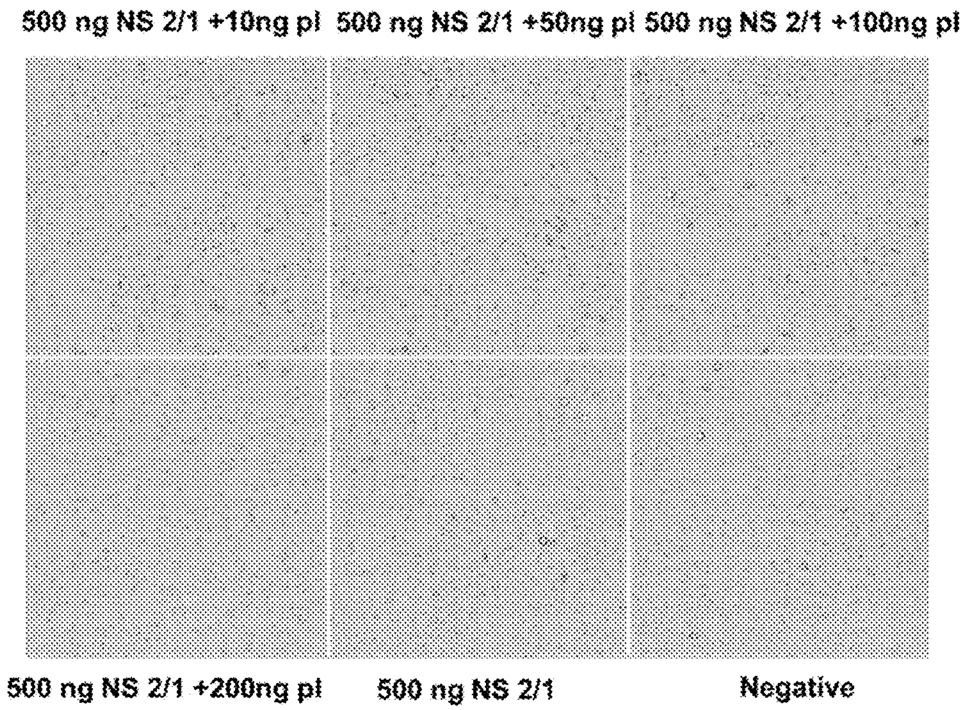
FIGS. 8A-B depict transfections performed on Human neonatal epidermal keratinocytes using various NoveSlice gene-editing proteins (NS). Cells were imaged using Operetta High-Content Imaging System to look at both fluorescent and phase images.
Figure 8B:
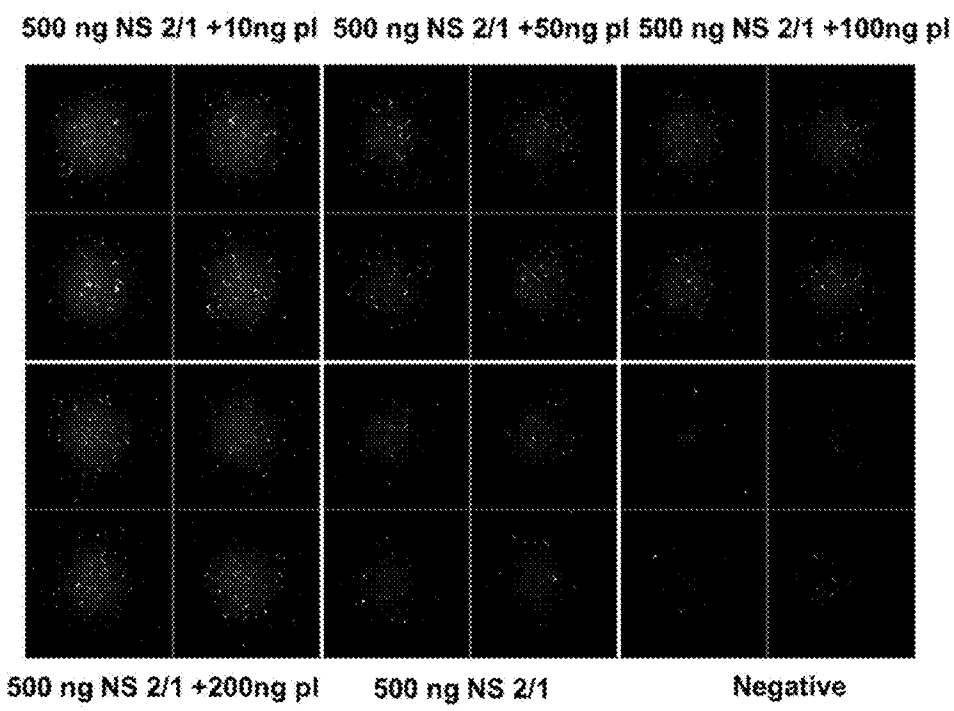
Figure 8C:
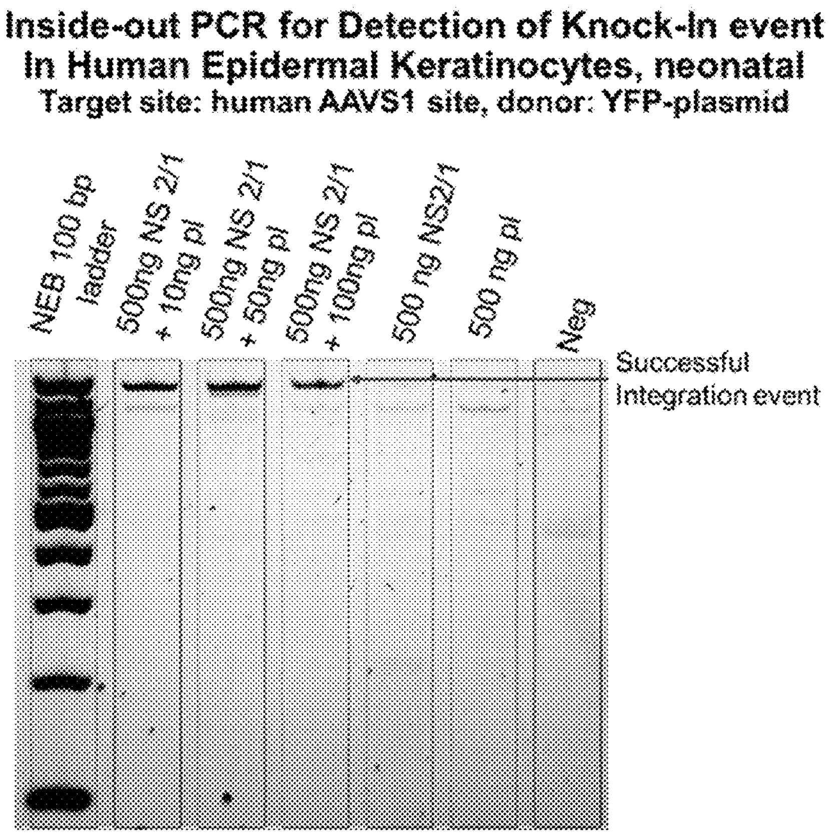
FIG. 8C depicts successful integration into the target human AAVS1 site in human epidermal keratinocytes using various NoveSlice gene-editing proteins (NS). Cells were DNA extracted and an Inside-out PCR was performed to determine if successful integration was achieved.
Figure 8D:
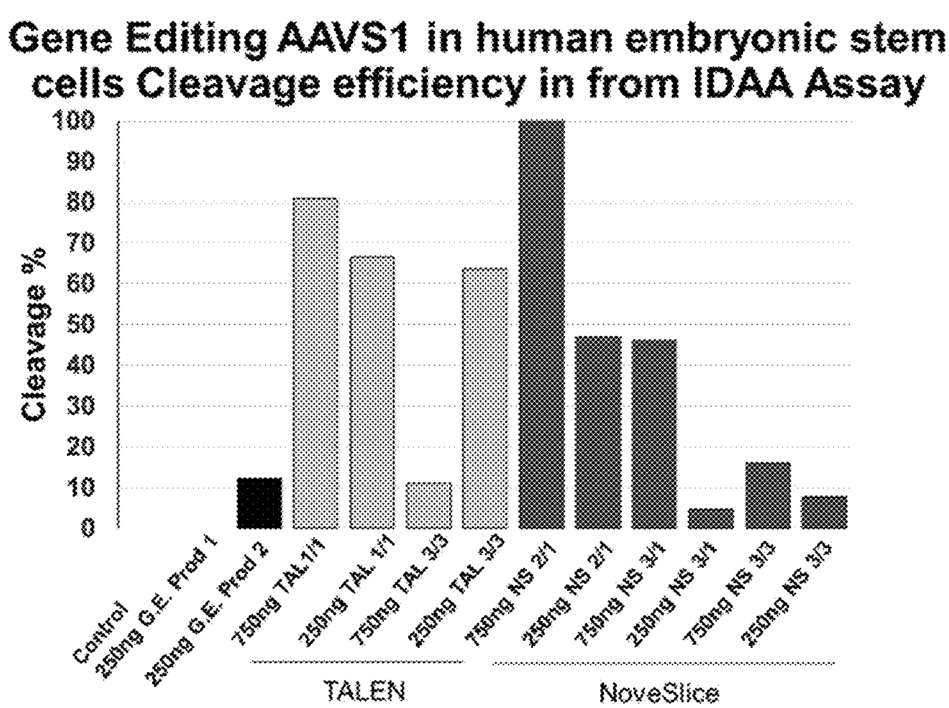
FIG. 8D depicts the cleavage efficiency of various NoveSlice gene-editing proteins (NS) in gene-editing the human AAVS1 target in human embryonic stem cells. Various gene-editing methods were compared to NoveSlice to determine cleavage efficiency using the IDAA Assay based on Yang et al. Fast and sensitive detection of indels induced by precise gene targeting *Nucleic Acids Res*. (2015) 43(9):e59 (the contents of which are incorporated herein in their entirety).

FIGS. 8A-B shows the results of transfections being performed on Human neonatal epidermal keratinocytes. Cells were imaged using Operetta High-Content Imaging System to look at both fluorescent and phase images. FIG. 8C shows that these cells were DNA extracted and an Inside-out PCR was performed to determine if successful integration was achieved. FIG. 8D shows that using the IDAA Assay from Yang Z, Steentoft C, Hauge C, et al. Fast and sensitive detection of indels induced by precise gene targeting. Nucleic Acids Res. 2015; 43(9):e59. doi:10.1093/nar/gkv126 various gene editing methods were compared to the present gene-editing proteins to determine Cleavage Efficiency.

Example 7 Temperature-Dependent Activity

Figure 9:
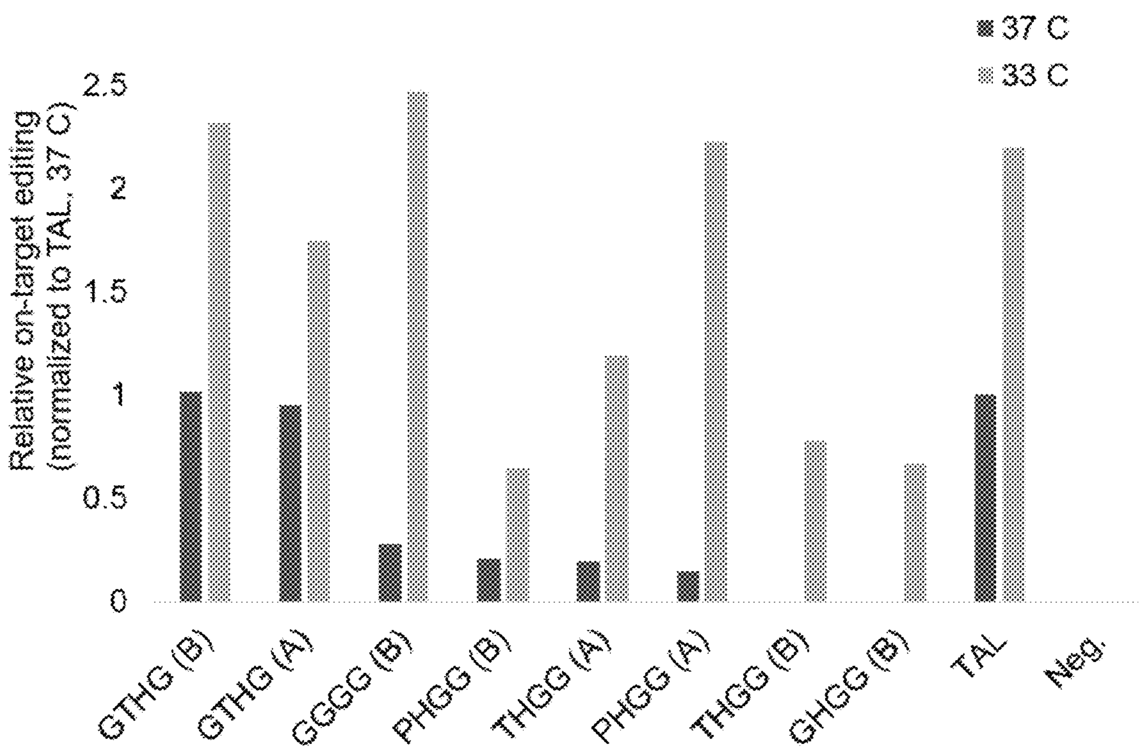
FIG. 9 shows efficiency and temperature-dependence of gene editing at a target locus. RNA was synthesized encoding repeat-array nucleases containing the repeat linker sequences indicated in odd-numbered repeat positions (A) or even-numbered repeat positions (B).

FIG. 9 shows that engineered repeat-array nucleases allow high-efficiency and temperature-dependent editing at target locus. RNA was synthesized encoding repeat-array nucleases containing the repeat linker sequences indicated in odd-numbered repeat positions (A) or even-numbered repeat positions (B). 1 μg of total RNA encoding left- and right-handed nucleases was electroporated into primary human epidermal keratinocytes. Cells were cultured for 48 hours at 37° C., 5% $CO_2$, then genomic DNA was extracted. The target locus (COL7A1 exon 73 splice acceptor) was amplified by PCR and a T7 endonuclease I assay was performed to determine editing efficiency, and normalized to the efficiency of wild-type TALENs at 37° C.

Figure 10A:
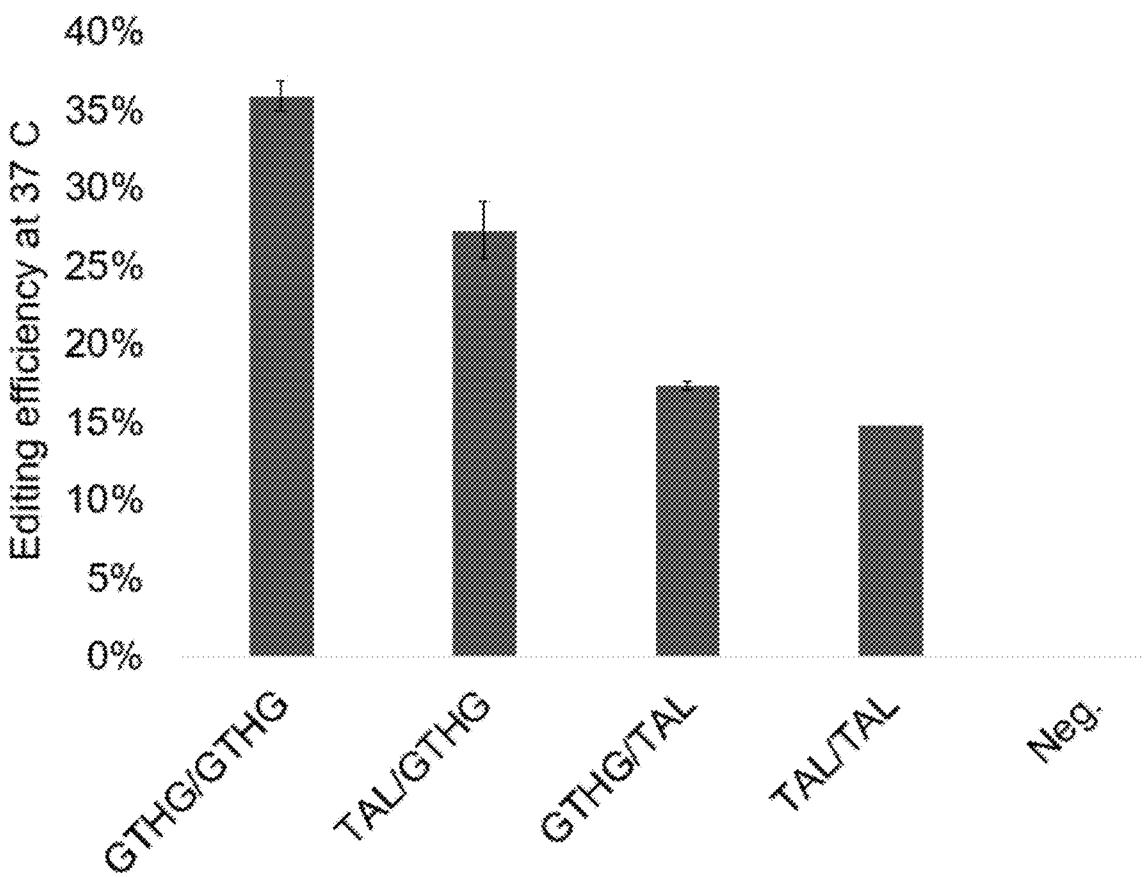
FIG. 10A shows that GTHG (SEQ ID NO: 62) repeat-array nucleases produce more efficient editing at the target locus than TALENs at 37° C.

FIG. 10A shows that GTHG (SEQ ID NO: 62) repeat-array nucleases produce more efficient editing at the target locus than TALENs at 37° C. 1 μg of total RNA encoding left- and right-handed nucleases was electroporated into primary human epidermal keratinocytes. Cells were cultured for 48 hours at 37° C., 5% $CO_2$, then genomic DNA was extracted. The target locus (COL7A1 exon 73 splice acceptor) was amplified by PCR and a T7 endonuclease I assay was performed to determine editing efficiency.

Figure 10B:
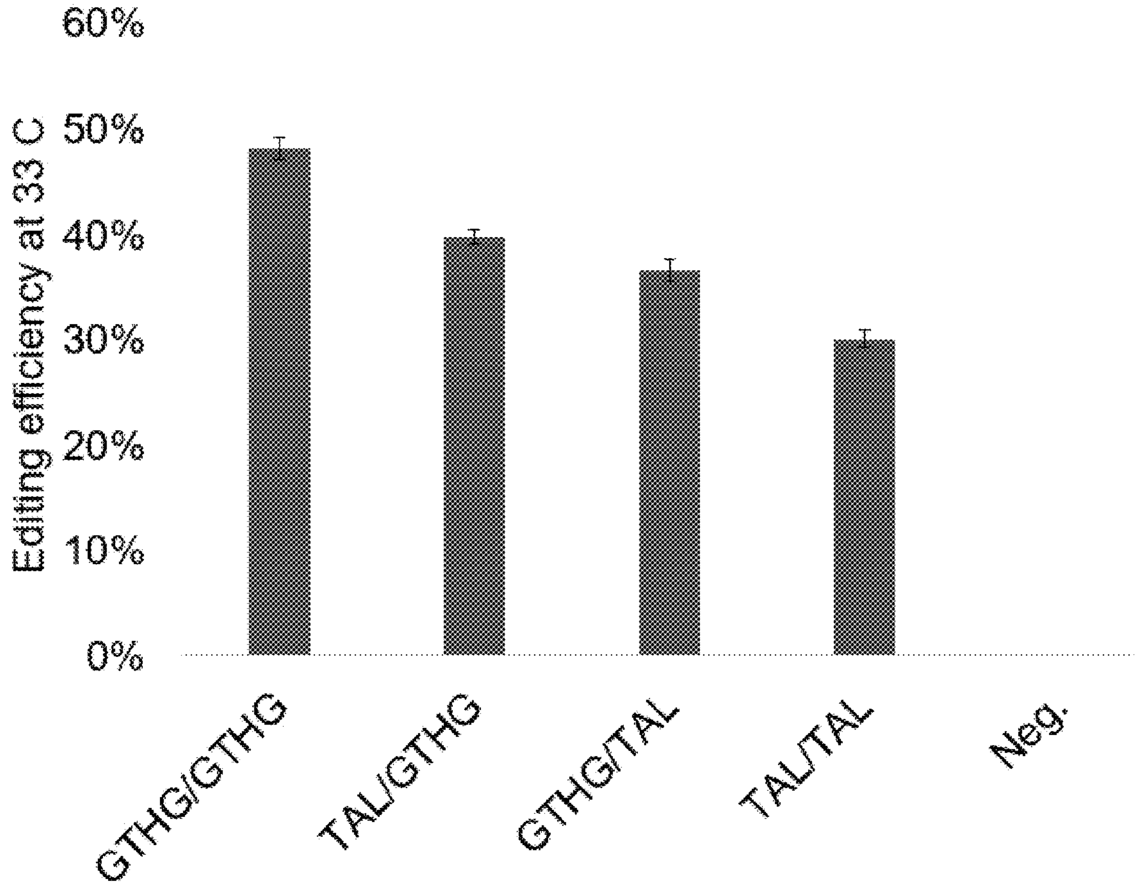
FIG. 10B shows that GTHG (SEQ ID NO: 62) repeat-array nucleases produce more efficient editing at the target locus than TALENs at 33° C.

FIG. 10B shows that GTHG (SEQ ID NO: 62) repeat-array nucleases produce more efficient editing at the target locus than TALENs at 33° C. 1 μg of total RNA encoding left- and right-handed nucleases was electroporated into primary human epidermal keratinocytes. Cells were cultured for 48 hours at 33° C., 5% $CO_2$, then genomic DNA was extracted. The target locus (COL7A1 exon 73 splice acceptor) was amplified by PCR and a T7 endonuclease I assay was performed to determine editing efficiency.

Figure 11:
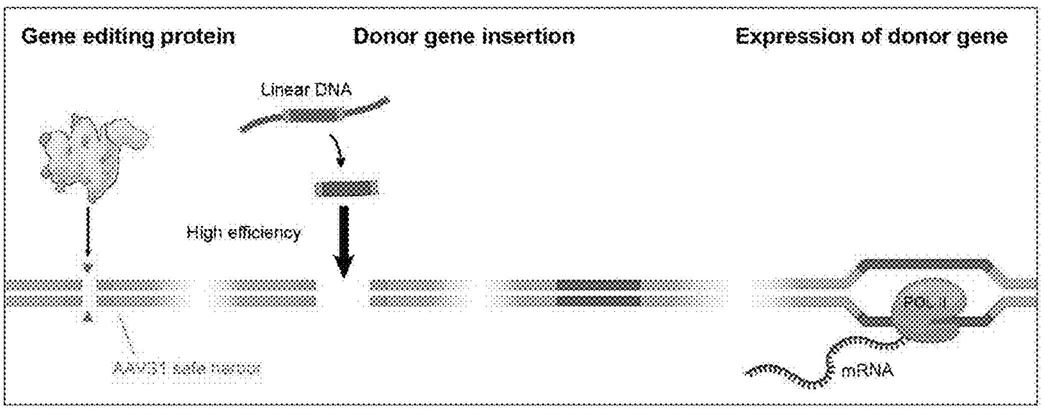
FIG. 11 shows a non-limiting schematic of the end-modified linear DNA donor approach described herein.

Example 8 Knock-In iPS Cell Line Generation Using End-Modified Linear DNA Donors To produce a targeted knock-in, a gene-editing endonuclease is used to create a double strand break (DSB) at a target site in the genome, and a plasmid donor containing a transgene as well as homology arms is inserted at the target site. However, rates of on-target integration using plasmid donors are very low, especially in primary cells and induced pluripotent stem cells (iPSCs). The present Example tested whether the use of end-modified linear DNA donors could result in higher insertion rates and increased target specificity when compared with traditional plasmid donors. See FIG. 11. End-modified linear donors were synthesized using PCR with standard primers, 5'-biotinylated primers, and primers containing a 5' polyethylene glycol (PEG) linker connected to a random 21-nucleotide single-stranded DNA sequence. See FIG. 12. All structures contain 500 nt of homology to AAVS1 on each side, flanking pEf1a-GFP-pA which expresses GFP and PGK-puroR which confers puromycin resistance. Right side shows primer sequences used to generate the corresponding repair template structures. /5BiosG/: 5' biotinylation, *: phosphorothioate bond, /5Phos/: 5' phosphorylation, /iSp18/: 18-atom hexa-ethyleneglycol spacer.

Whether these donors could exhibit lower cytotoxicity, increased persistence in cells, and improved rates of on-target integration was tested. To examine these characteristics, the three donors in knock-in experiments using primary human fibroblasts and iPSCs were compared. End-modified linear donors encoding green fluorescent protein (GFP) and a puromycin resistance gene were synthesized and electroporated into fibroblasts and iPSCs together with mRNA encoding the present gene-editing proteins targeting a sequence within the AAVS1 locus.

Figure 13A:
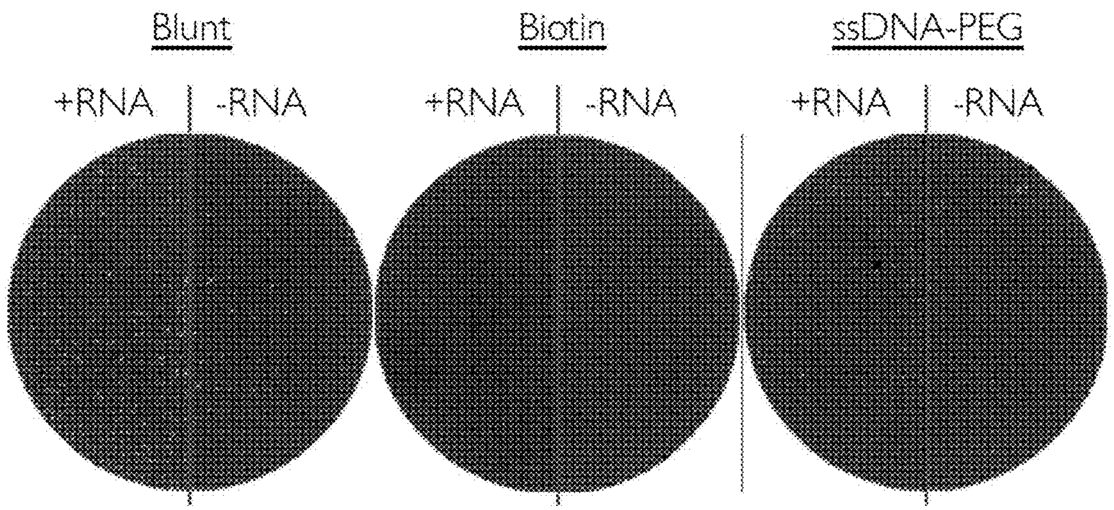
FIG. 13A-B shows primary human fibroblasts after electroporation of the repair template structures described herein.
Figure 13B:
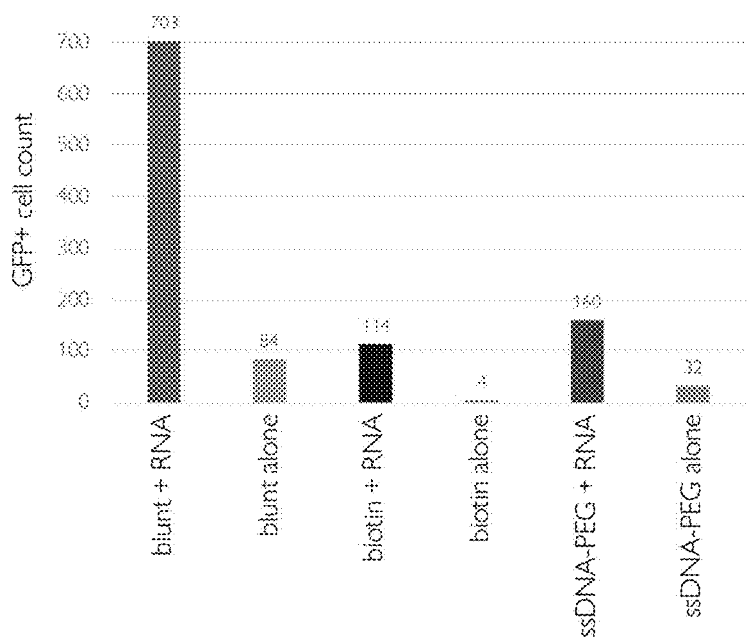

FIG. 13A shows primary human fibroblasts 2 days after electroporation of the repair template structures of FIG. 12 with and without RNA encoding gene-editing proteins targeting the AAVS1 site. The presence of gene-editing RNA increases the number of green cells. FIG. 13B shows green cell count of primary human fibroblasts 7 days after electroporation of the repair template structures of FIG. 12 with and without RNA encoding gene-editing proteins targeting the AAVS1 site. The presence of gene-editing RNA increases the number of green cells.

Figure 14A:
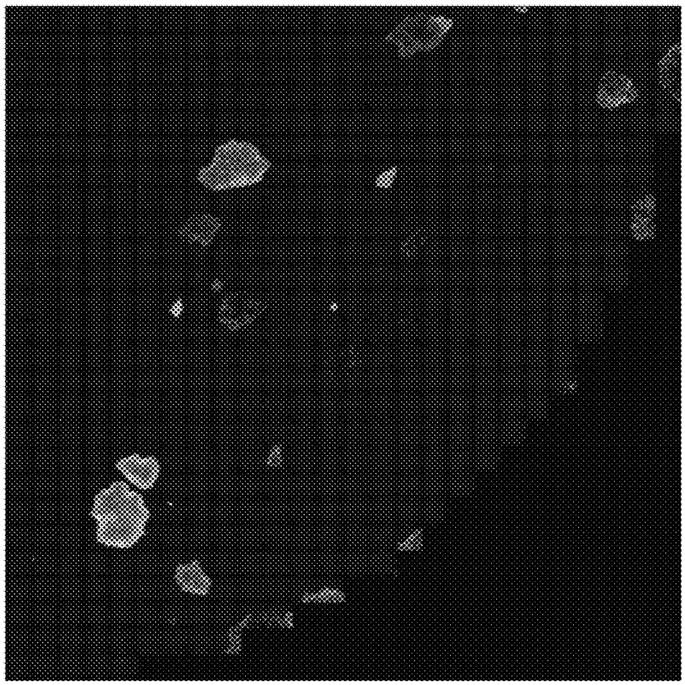
FIG. 14A-B shows induced pluripotent stem cells (iPSCs) after electroporation of the repair template structures described herein.
Figure 14B:
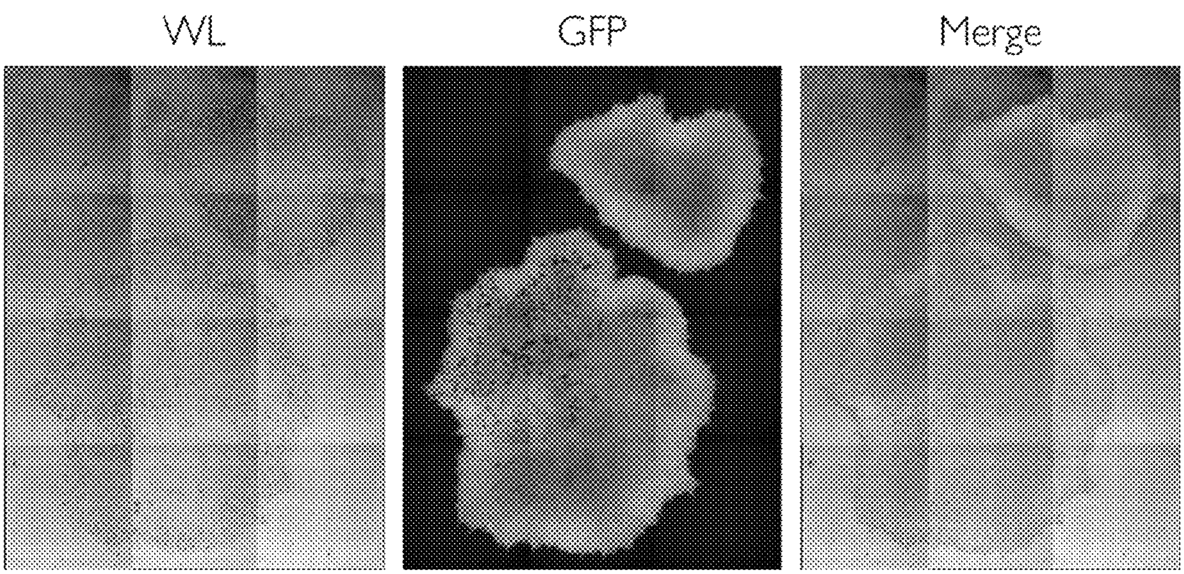

FIG. 14A shows induced pluripotent stem cells (iPSCs) after electroporation of the repair template structures of FIG. 12 and RNA encoding gene-editing proteins targeting the AAVS1 site and puromycin selection. FIG. 14B shows a closeup of individual iPSC colonies in FIG. 14A.

Using GFP expression levels as a marker, the standard PCR donor resulted in the highest insertion rate, followed by the 5' ssPEG donor and the biotinylated donor. All three donors resulted in higher integration rates than a plasmid containing the same sequence. Transfected iPSCs formed colonies of cells with uniform GFP expression that were isolated and propagated as stable knock-in lines.

This Example shows that end-modified linear donors integrate at higher rates than plasmid donors. Use of these donors may therefore represent a preferred approach for the generation of knock-in iPS cell lines.

Example 9 Engineering to Remove to Constraints

Figure 15:
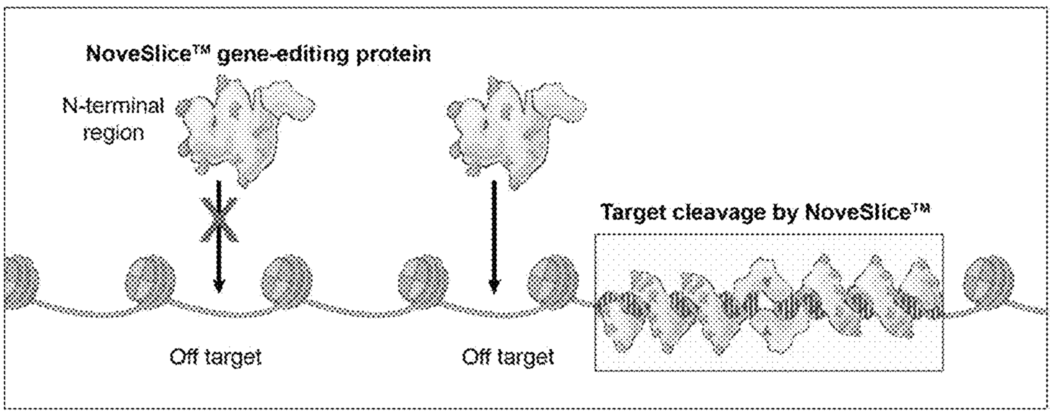
FIG. 15 shows a non-limiting schematic of the $T_0$ constraint removal engineering described herein.

TALENs require a thymine (T) in the zero position of the target site ("To"). The present Example is directed to, inter alia, removing the $T_0$ requirement of TALEN and the present gene-editing proteins through amino-acid substitution of residues in the N-terminal region of the DNA-binding domain. See FIG. 15. Constructs encoding the present gene-editing proteins and TALEN proteins with various N-terminal regions were designed and synthesized using site directed mutagenesis. The gene editing efficiency of these proteins was assayed by mRNA transfection into primary human keratinocytes. After 48 hours the target site was amplified, a region near the COL7A1 exon 73 splice acceptor site, and assessed editing using T7 endonuclease I. From this initial screen, an N-terminal region that had the highest editing efficiency in a target site with an N0 was identified. Surprisingly, when measuring cutting of an N0-containing target site, "off-target" editing by TALENs was observed while there was no editing by the present gene-editing proteins under these same conditions. Thus, the present gene-editing proteins showed a higher degree of specificity when compared to TALENs for this clinically relevant target site.

FIG. 16 shows TALEN cutting using the "GSKRGAGS" (SEQ ID NO: 32) form at a target site that does not begin with T. FIG. 16 shows T7E1 results of TALENs targeting sites in the COL7A1 gene 48 hr after electroporation of primary human keratinocytes with mRNA encoding gene editing proteins. TAL→T0 shows the effect of a TALEN pair designed to target sites beginning with T (TGTACAGCCACCAGCATTCT (SEQ ID NO: 34)/TCCAGGAAAGCCGATGGGGC (SEQ ID NO: 35)) using a WT N-terminus, while TAL-GS→(N0) show targeting of sequences that do not begin with T (GTACAGCCACCAGCATTCTC (SEQ ID NO: 36)/CTCCAGGAAAGCCGATGGGG (SEQ ID NO: 37)) using the "GSKRGAGS" (SEQ ID NO: 32) modification at the N terminus.

These data suggest that the present gene-editing proteins can yield higher specificity than TALENs targeting the same site in primary human cells, and thus could offer an advantage in the development of both ex-vivo and in-vivo gene editing therapies.

Definitions

The following definitions are used in connection with the invention disclosed herein. Unless defined otherwise, all technical and scientific terms used herein have the same meaning as commonly understood to one of skill in the art to which this invention belongs.

The term "in vivo" refers to an event that takes place in a subject's body.

The term "ex vivo" refers to an event which involves treating or performing a procedure on a cell, tissue and/or organ which has been removed from a subject's body. Aptly, the cell, tissue and/or organ may be returned to the subject's body in a method of treatment or surgery.

As used herein, the term "variant" encompasses but is not limited to nucleic acids or proteins which comprise a nucleic acid or amino acid sequence which differs from the nucleic acid or amino acid sequence of a reference by way of one or more substitutions, deletions and/or additions at certain positions. The variant may comprise one or more conservative substitutions. Conservative substitutions may involve, e.g., the substitution of similarly charged or uncharged amino acids.

"Carrier" or "vehicle" as used herein refer to carrier materials suitable for drug administration. Carriers and vehicles useful herein include any such materials known in the art, e.g., any liquid, gel, solvent, liquid diluent, solubilizer, surfactant, lipid or the like, which is nontoxic and which does not interact with other components of the composition in a deleterious manner.

The phrase "pharmaceutically acceptable" refers to those compounds, materials, compositions, and/or dosage forms that are, within the scope of sound medical judgment, suitable for use in contact with the tissues of human beings and animals without excessive toxicity, irritation, allergic response, or other problems or complications commensurate with a reasonable benefit/risk ratio.

The terms "pharmaceutically acceptable carrier" or "pharmaceutically acceptable excipient" are intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in the therapeutic compositions of the invention is contemplated. Additional active pharmaceutical ingredients, such as other drugs, can also be incorporated into the described compositions and methods.

As used herein, "a," "an," or "the" can mean one or more than one.

Further, the term "about" when used in connection with a referenced numeric indication means the referenced numeric indication plus or minus up to 10% of that referenced numeric indication. For example, the language "about 50" covers the range of 45 to 55.

As used herein, the word "include," and its variants, is intended to be non-limiting, such that recitation of items in a list is not to the exclusion of other like items that may also be useful in the compositions and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

The term "H" denotes a single hydrogen atom. This radical may be attached, for example, to an oxygen atom to form a hydroxyl radical.

Where the term "alkyl" is used, either alone or within other terms such as "haloalkyl" or "alkylamino", it embraces linear or branched radicals having one to about twenty carbon atoms, denoted as $C_1$-$C_{20}$ alkyl. Examples of such radicals include methyl, ethyl, n-propyl, isopropyl, n-butyl, isobutyl, sec-butyl, tert-butyl, pentyl, isoamyl, hexyl and the like. The term "alkylenyl," "alkylene," or "alkanediyl," embraces bridging divalent alkyl radicals such as methylenyl or ethylenyl. The term "alkenyl" embraces linear or branched radicals of two to about sixty carbon atoms having at least one carbon-carbon double bond. In some instances, the "alkenyl" radical has two carbon-carbon double bonds that may or may not be conjugated. In some instances, the "alkenyl" radical has more than two carbon-carbon double bonds that independently may or may not be conjugated. In some instances, the "alkenyl" radical has at least one carbon-carbon double bond and at least one carbon-carbon triple bond that may or may not be conjugated. Examples of alkenyl radicals include ethenyl, propenyl, allyl, propenyl, butenyl and 4-methylbutenyl. The terms "alkenyl" embraces radicals having "cis" and "trans" orientations, or alternatively, "E" and "Z" orientations.

The term "alkynyl" denotes linear or branched radicals having at least one carbon-carbon triple bond and having two to about sixty carbon atoms. Examples of such radicals include propargyl, and butynyl, and the like. Alkyl, alkylenyl, alkenyl, and alkynyl radicals may be optionally substituted with one or more functional groups such as halo, hydroxy, nitro, amino, cyano, haloalkyl, aryl, heteroaryl, and heterocyclo and the like.

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals including perhaloalkyl. A monohaloalkyl radical, for example, may have either an iodo, bromo, chloro or fluoro atom within the radical. Dihalo and polyhaloalkyl radicals may have two or more of the same halo atoms or a combination of different halo radicals. Even more preferred are lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl.

The term "hydroxyalkyl" embraces linear or branched alkyl radicals having one to about ten carbon atoms any one of which may be substituted with one or more hydroxyl radicals. Examples of such radicals include hydroxymethyl, hydroxyethyl, hydroxypropyl, hydroxybutyl and hydroxyhexyl.

The term "alkoxy" embraces linear or branched oxy-containing radicals each having alkyl portions of one to about twenty carbon atoms. Examples of such radicals include methoxy, ethoxy, propoxy, butoxy and Pert-butoxy. Even more preferred are lower alkoxy radicals having one to twelve carbon atoms. Alkoxy radicals may be further substituted with one or more halo atoms, such as fluoro, chloro or bromo, to provide "haloalkoxy" radicals. Examples of such radicals include fluoromethoxy, chloromethoxy, trifluoromethoxy, trifluoroethoxy, fluoroethoxy and fluoropropoxy.

The term "aryl", alone or in combination, means a carbocyclic aromatic system containing one or two rings, wherein such rings may be attached together in a fused manner. The term "aryl" embraces aromatic radicals such as phenyl, naphthyl, indenyl, tetrahydronaphthyl, and indanyl. More preferred aryl is phenyl. An "aryl" group may have 1 or more substituents such as alkyl, hydroxyl, halo, haloalkyl, nitro, cyano, alkoxy, and alkylamino, and the like. The term "arylene" embraces bridging divalent aryl radicals, such as benzylene, phenylene, and the like.

The term "heterocyclyl" (or "heterocyclo") embraces saturated, partially saturated and unsaturated heteroatom-containing ring radicals, where the heteroatoms may be selected from nitrogen, sulfur and oxygen. The "heterocyclyl" group may have 1 to 4 substituents such as hydroxyl, Boc, halo, haloalkyl, cyano, lower alkyl, lower aralkyl, oxo, lower alkoxy, amino and lower alkylamino.

Examples of saturated heterocyclic radicals include saturated 3 to 6-membered heteromonocyclic groups containing 1 to 4 nitrogen atoms [e.g., pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g., morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

Examples of unsaturated heterocyclic radicals, also termed "heteroaryl" radicals, include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl]. The term heterocyclyl, (or heterocyclo) also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Preferred heterocyclic radicals include five to ten membered fused or unfused radicals. More preferred examples of heteroaryl radicals include quinolyl, isoquinolyl, imidazolyl, pyridyl, thienyl, thiazolyl, oxazolyl, furyl and pyrazinyl. Other preferred heteroaryl radicals are 5- or 6-membered heteroaryl, containing one or two heteroatoms selected from sulfur, nitrogen and oxygen, selected from thienyl, furyl, pyrrolyl, indazolyl, pyrazolyl, oxazolyl, triazolyl, imidazolyl, pyrazolyl, isoxazolyl, isothiazolyl, pyridyl, piperidinyl and pyrazinyl. Particular examples of non-nitrogen containing heteroaryl include pyranyl, 2-furyl, 3-furyl, 2-thienyl, 3-thienyl, benzofuryl, and benzothienyl, and the like.

Particular examples of partially saturated and saturated heterocyclyl include pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.
The term “heterocyclo” thus encompasses the following ring systems:
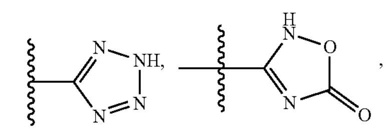
,
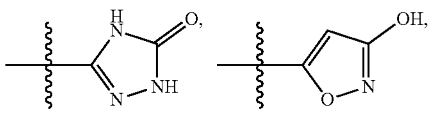
,
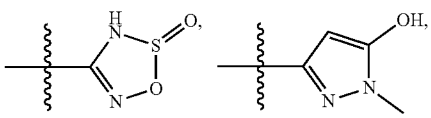
,
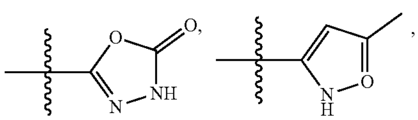
,
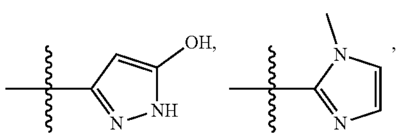
,
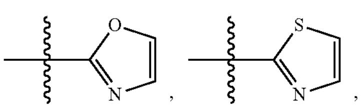
,
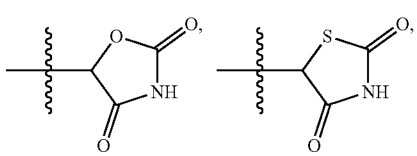
,
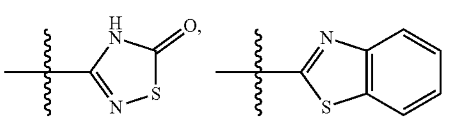
,
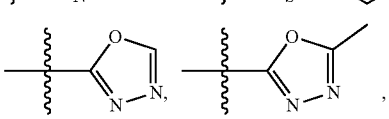
,
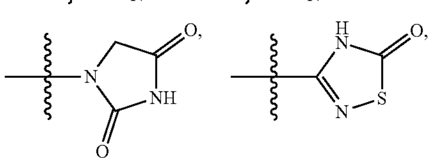
,
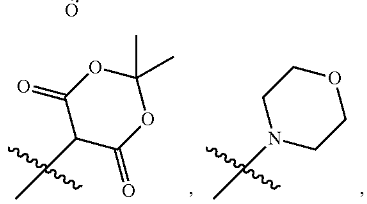
,
-continued
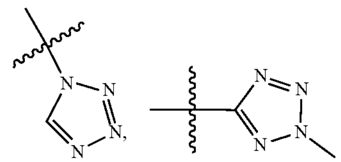
,
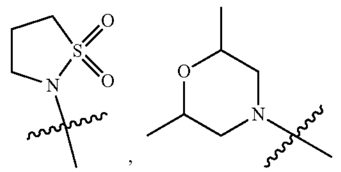
,
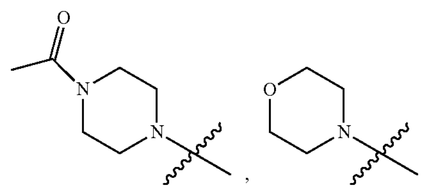
,
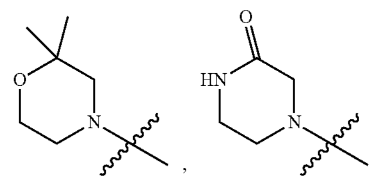
,
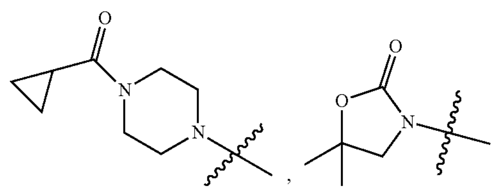
,
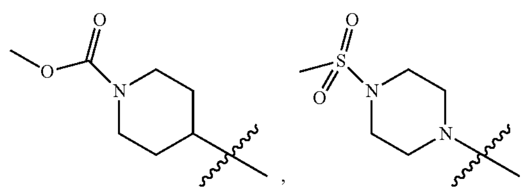
,
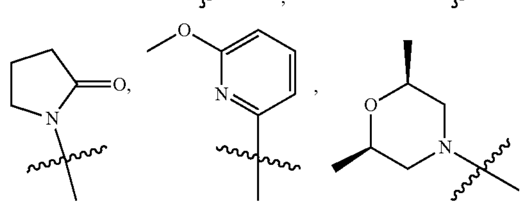
,
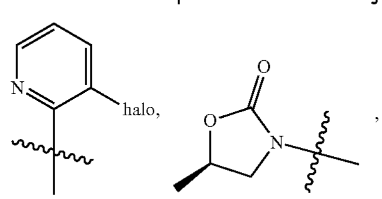
,
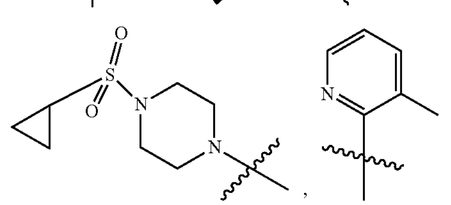
, -continued

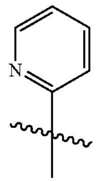,
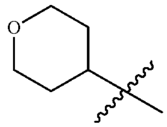,
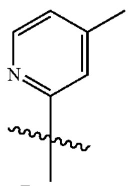,
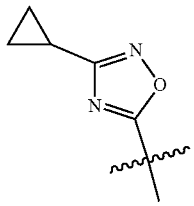,
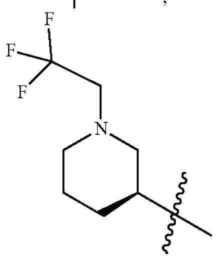,
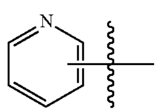,
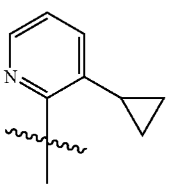,
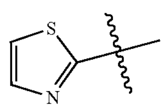,
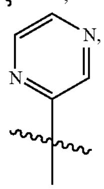
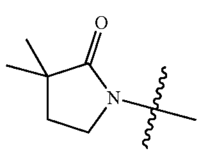,
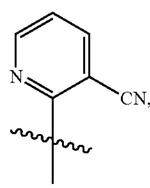
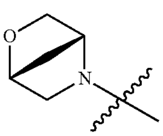,
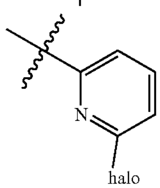,
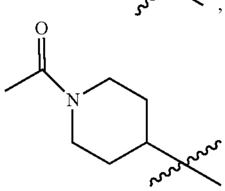,
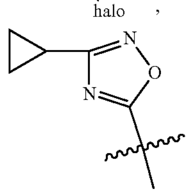,
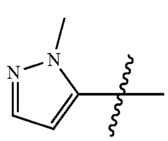,
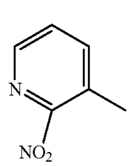,
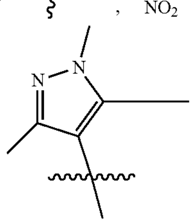, and the like.

The term "carbonyl," whether used alone or with other terms, such as "aminocarbonyl," denotes —(C═O)—.

The terms "heterocyclylalkylenyl" and "heterocyclylalkyl" embrace heterocyclic-substituted alkyl radicals. More preferred heterocyclylalkyl radicals are "5- or 6-membered heteroarylalkyl" radicals having alkyl portions of one to six carbon atoms and a 5- or 6-membered heteroaryl radical. Even more preferred are lower heteroarylalkylenyl radicals having alkyl portions of one to three carbon atoms. Examples include such radicals as pyridylmethyl and thienylmethyl.

The term "cycloalkyl" includes saturated carbocyclic groups. Preferred cycloalkyl groups include $C_3$-$C_6$ rings. More preferred compounds include, cyclopentyl, cyclopropyl, and cyclohexyl.

The term "cycloalkenyl" includes carbocyclic groups having one or more carbon-carbon double bonds including "cycloalkyldienyl" compounds. Preferred cycloalkenyl groups include 03-06 rings. More preferred compounds include, for example, cyclopentenyl, cyclopentadienyl, cyclohexenyl and cycloheptadienyl.

The term "lipid" encompasses, without limitation, a biomolecule that is insoluble in water but soluble in organic solvents, being derived from natural sources, and/or being synthetically produced, and nonnatural analogs and derivatives of such a biomolecule. Examples of lipids include, without limitation, compounds otherwise described as "lipid-like" or "lipidoid", and the compounds of Formulae I-XVI. Other examples of lipids include, without limitation, synthetic molecules that comprise natural lipids, their derivatives, and their analogs, even if said synthetic molecules are themselves water-soluble. Other examples of lipids include, without limitation, molecules comprising one or more $C_5$-$C_{20}$ alkyl groups, sterols, fatty acids, and their analogues and derivatives.

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features herein set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

What is claimed is:

1. A method for gene-editing a cell, the method comprising:

(a) providing a nucleic acid molecule encoding a gene-editing protein, the gene-editing protein comprising:

(i) a DNA-binding domain comprising a plurality of repeat sequences and at least one of the repeat sequences comprising a repeat variable di-residue (RVD) at residue 12 or 13 which targets the DNA-binding domain to a target DNA molecule, wherein at least one of the repeat sequences comprises an amino acid sequence LTPvQVVAIAwxyzα (SEQ ID NO: 11) wherein v is E, w is S, x is I, H, N, or I, y is D, A, I, N, H, K, S, G, or null, z is SEQ ID NO: 8, and a is GTHG (SEQ ID NO: 62); and (ii) a nuclease domain comprising a catalytic domain of a nuclease which is capable of creating a single-strand break or a double-strand break in the target DNA molecule;

wherein the nucleic acid molecule is a synthetic RNA molecule; and (b) contacting the cell with the synthetic RNA molecule to yield a single-strand break or a double-strand break in the target DNA molecule in the cell, wherein the contacting occurs at a temperature from about 30° C. to about 35° C.; and wherein the efficiency of the gene-editing at a temperature from about 30° C. to about 35° C. is greater than the efficiency of the gene-editing at a temperature of about 37° C.

2. The method of claim 1, wherein the contacting comprises transfection of the synthetic RNA molecule into the cell.

3. The method of claim 1, wherein the gene-editing protein is functionally temperature-switchable which allows for conditional gene-editing.

4. The method of claim 1, wherein the contacting occurs in vitro, ex vivo, or in vivo.

5. The method of claim 4, wherein the contacting is in vitro or ex vivo and the method further comprises (c): culturing the cell, thereby obtaining a cultured cell comprising a single-strand break or a double-strand break in the target DNA molecule.

6. The method of claim 5, further comprising (d): administering to a subject in need thereof the cultured cell comprising the single-strand break or the double-strand break in the target DNA molecule, wherein the cultured cell is formulated for therapeutic use and is suitable for administration to the subject in need thereof.

7. The method of claim 4, wherein the contacting occurs in vivo and the method further comprises reducing the temperature of a location of the subject, thereby providing gene-editing in cells at the location of the subject which has a reduced temperature.

8. The method of claim 7, wherein reducing the temperature of the location of the subject comprises applying one or more cooling elements to the location of the subject, optionally wherein the cooling element is a cryocompression device or the cooling element provides whole-body hypothermia.

9. The method of claim 1, wherein the contacting occurs at a temperature of about 30° C. or about 33° C.

10. The method of claim 1, wherein the cell is a skin cell, optionally selected from a fibroblast, a keratinocyte, a melanocyte, or an adipocyte.

11. The method of claim 1, wherein the nuclease domain is capable of forming a dimer with another nuclease domain.

12. The method of claim 1, wherein the catalytic domain is from FokI, StsI, or a hybrid thereof.

13. The method of claim 12, wherein the catalytic domain comprises a hybrid of the catalytic domains of FokI and StsI, the hybrid comprising the α1, α2, α3, α4, α5, α6, β1, β2, β3, β4, β5, and β6 domains of FokI with at least one of the domains of FokI being substituted in whole or in part with the α1, α2, α3, α4, α5, α6, β1, β2, β3, β4, 5, and β6 domains of StsI and optionally comprising at least one mutation.

14. The method of claim 1, wherein the synthetic RNA molecule is mRNA.

15. The method of claim 14, wherein the mRNA comprises one or more non-canonical nucleotides selected from 2-thiouridine, 5-azauridine, pseudouridine, 4-thiouridine, 5-methyluridine, 5-methylpseudouridine, 5-aminouridine, 5-aminopseudouridine, 5-hydroxyuridine, 5-hydroxypseudouridine, 5-methoxyuridine, 5-methoxypseudouridine, 5-ethoxyuridine, 5-ethoxypseudouridine, 5-hydroxymethyluridine, 5-hydroxymethylpseudouridine, 5-carboxyuridine, 5-carboxypseudouridine, 5-formyluridine, 5-formylpseudouridine, 5-methyl-5-azauridine, 5-amino-5-azauridine, 5-hydroxy-5-azauridine, 5-methylpseudouridine, 5-aminopseudouridine, 5-hydroxypseudouridine, 4-thio-5-azauridine, 4-thiopseudouridine, 4-thio-5-methyluridine, 4-thio-5-aminouridine, 4-thio-5-hydroxyuridine, 4-thio-5-methyl-5-azauridine, 4-thio-5-amino-5-azauridine, 4-thio-5-hydroxy-5-azauridine, 4-thio-5-methylpseudouridine, 4-thio-5-aminopseudouridine, 4-thio-5-hydroxypseudouridine, 2-thiocytidine, 5-azacytidine, pseudoisocytidine, N4-methylcytidine, N4-aminocytidine, N4-hydroxycytidine, 5-methylcytidine, 5-aminocytidine, 5-hydroxycytidine, 5-methoxycytidine, 5-ethoxycytidine, 5-hydroxymethylcytidine, 5-carboxycytidine, 5-formylcytydine, 5-methyl-5-azacytidine, 5-amino-5-azacytidine, 5-hydroxy-5-azacytidine, 5-methylpseudoisocytidine, 5-aminopseudoisocytidine, 5-hydroxypseudoisocytidine, N4-methyl-5-azacytidine, N4-methylpseudoisocytidine, 2-thio-5-azacytidine, 2-thiopseudoisocytidine, 2-thio-N4-methylcytidine, 2-thio-N4-aminocytidine, 2-thio-N4-hydroxycytidine, 2-thio-5-methylcytidine, 2-thio-5-aminocytidine, 2-thio-5-hydroxycytidine, 2-thio-5-methyl-5-azacytidine, 2-thio-5-amino-5-azacytidine, 2-thio-5-hydroxy-5-azacytidine, 2-thio-5-methylpseudoisocytidine, 2-thio-5-aminopseudoisocytidine, 2-thio-5-hydroxypseudoisocytidine, 2-thio-N4-methyl-5-azacytidine, 2-thio-N4-methylpseudoisocytidine, N4-methyl-5-methylcytidine, N4-methyl-5-aminocytidine, N4-methyl-5-hydroxycytidine, N4-methyl-5-methyl-5-azacytidine, N4-methyl-5-amino-5-azacytidine, N4-methyl-5-hydroxy-5-azacytidine, N4-methyl-5-methylpseudoisocytidine, N4-methyl-5-aminopseudoisocytidine, N4-methyl-5-hydroxypseudoisocytidine, N4-amino-5-azacytidine, N4-aminopseudoisocytidine, N4-amino-5-methylcytidine, N4-amino-5-aminocytidine, N4-amino-5-hydroxycytidine, N4-amino-5-methyl-5-azacytidine, N4-amino-5-amino-5-azacytidine, N4-amino-5-hydroxy-5-azacytidine, N4-amino-5-methylpseudoisocytidine, N4-amino-5-aminopseudoisocytidine, N4-amino-5-hydroxypseudoisocytidine, N4-hydroxy-5-azacytidine, N4-hydroxypseudoisocytidine, N4-hydroxy-5-methylcytidine, N4-hydroxy-5-aminocytidine, N4-hydroxy-5-hydroxycytidine, N4-hydroxy-5-methyl-5-azacytidine, N4-hydroxy-5-amino-5-azacytidine, N4-hydroxy-5-hydroxy-5-azacytidine, N4-hydroxy-5-methylpseudoisocytidine, N4-hydroxy-5-aminopseudoisocytidine, N4-hydroxy-5-hydroxypseudoisocytidine, 2-thio-N4-methyl-5-methylcytidine, 2-thio-N4-methyl-5-aminocytidine, 2-thio-N4-methyl-5-hydroxycytidine, 2-thio-N4-methyl-5-methyl-5-azacytidine, 2-thio-N4-methyl-5-amino-5-azacytidine, 2-thio-N4-methyl-5-hydroxy-5-2-thio-N4-methyl-5-azacytidine, 2-thio-N4-methyl-5-methylpseudoisocytidine, aminopseudoisocytidine, 2-thio-N4-methyl-5-hydroxypseudoisocytidine, 2-thio-N4-amino-5-azacytidine, 2-thio-N4-aminopseudoisocytidine, 2-thio-N4-amino-5-methylcytidine, 2-thio-N4-amino-5-aminocytidine, 2-thio-N4-amino-5-hydroxycytidine, 2-thio-N4-amino-5-methyl-5-azacytidine, 2-thio-N4-amino-5-amino-5-azacytidine, 2-thio-N4-amino-5-hydroxy-5-azacytidine, 2-thio-N4-amino-5-methylpseudoisocytidine, 2-thio-N4-amino-5-aminopseudoisocytidine, 2-thio-N4-amino-5-hydroxypseudoisocytidine, 2-thio-N4-hydroxy-5-azacytidine, 2-thio-N4-hydroxypseudoisocytidine, 2-thio-N4-hydroxy-5-methylcytidine, N4-hydroxy-5-aminocytidine, 2-thio-N4-hydroxy-5-hydroxycytidine, 2-thio-N4-hydroxy-5-methyl-5-azacytidine, 2-thio-N4-hydroxy-5-amino-5-azacytidine, 2-thio-N4-hydroxy-5-hydroxy-5-azacytidine, 2-thio-N4-hydroxy-5-methylpseudoisocytidine, 2-thio-N4-hydroxy-5-aminopseudoisocytidine, 2-thio-N4-hydroxy-5-hydroxypseudoisocytidine, N6-methyladenosine, N6-aminoadenosine, N6-hydroxyadenosine, 7-deazaadenosine, 8-azaadenosine, N6-methyl-7-deazaadenosine, N6-methyl-8-azaadenosine, 7-deaza-8-azaadenosine, N6-methyl-7-deaza-8-azaadenosine, N6-amino-7-deazaadenosine, N6-amino-8-azaadenosine, N6-amino-7-deaza-8-azaadenosine, N6-hydroxyadenosine, N6-hydroxy-7-deazaadenosine, N6-hydroxy-8-azaadenosine, N6-hydroxy-7-deaza-8-azaadenosine, 6-thioguanosine, 7-deazaguanosine, 8-azaguanosine, 6-thio-7-deazaguanosine, 6-thio-8-azaguanosine, 7-deaza-8-azaguanosine, and 6-thio-7-deaza-8-azaguanosine.

16. The method of claim 1, wherein the synthetic RNA molecule comprises a 5' cap structure, a 5'-UTR comprising a Kozak consensus sequence, a 5'-UTR comprising a sequence that increases RNA stability in vivo, a 3'-UTR comprising a sequence that increases RNA stability in vivo, and/or a 3' poly(A) tail or a tail comprising a plurality of adenines with one or more guanines.

17. The method of claim 16, wherein the synthetic RNA molecule comprises a 3' poly(A) tail or a tail comprising a plurality of adenines with one or more guanines.

18. The method of claim 17, wherein the synthetic RNA molecule comprises a tail comprising a plurality of adenines with one or more guanines.

19. The method of claim 1, wherein the DNA-binding domain comprises about 15 repeat sequences, about 16 repeat sequences, about 17 repeat sequences, about 18 repeat sequences, or about 18.5 repeat sequences.

20. The method of claim 1, wherein the method further comprises contacting the cell with a linear DNA repair template.

21. The method of claim 1, wherein x is N.

22. The method of claim 1, wherein y is N.

* * * * *